US008710104B2

(12) United States Patent  (10) Patent No.: US 8,710,104 B2
White et al.  (45) Date of Patent: Apr. 29, 2014

(54) CATECHOLIC BUTANES AND USE THEREOF FOR CANCER THERAPY

(75) Inventors: Thomas F. White, San Francisco, CA (US); Edward F. Schnipper, Redwood City, CA (US); Dan Hoth, San Francisco, CA (US)

(73) Assignee: Triact Therapeutics, Inc., San Francisco, CA (US)

( * ) Notice: Subject to any disclaimer, the term of this patent is extended or adjusted under 35 U.S.C. 154(b) by 90 days.

(21) Appl. No.: 12/614,283

(22) Filed: Nov. 6, 2009

(65) Prior Publication Data
US 2010/0256232 A1 Oct. 7, 2010

Related U.S. Application Data

(60) Provisional application No. 61/112,621, filed on Nov. 7, 2008.

(51) Int. Cl.
*A61K 31/05* (2006.01)
(52) U.S. Cl.
CPC ..................................... *A61K 31/05* (2013.01)
USPC .......................................... 514/734; 514/721
(58) Field of Classification Search
CPC ................................ A61K 31/05; C07C 43/20
USPC .................................................. 514/721, 724
See application file for complete search history.

(56) References Cited

U.S. PATENT DOCUMENTS

| | | | |
|---|---|---|---|
| 4,683,202 A | 7/1987 | Mullis | |
| 4,843,155 A | 6/1989 | Chomczynski | |
| 4,868,103 A | 9/1989 | Stavrianopoulos et al. | |
| 4,946,778 A | 8/1990 | Ladner et al. | |
| 5,008,294 A | 4/1991 | Neiss et al. | |
| 5,541,232 A * | 7/1996 | Howell et al. ............... | 514/731 |
| 5,624,803 A | 4/1997 | Noonberg et al. | |
| 5,631,169 A | 5/1997 | Lakowicz et al. | |
| 5,650,415 A | 7/1997 | Tang et al. | |
| 5,656,643 A | 8/1997 | Spada et al. | |
| 5,747,498 A | 5/1998 | Schnur et al. | |
| 5,789,427 A | 8/1998 | Chen et al. | |
| 5,854,033 A | 12/1998 | Lizardi | |
| 5,981,732 A | 11/1999 | Cowsert | |
| 6,046,321 A | 4/2000 | Cowsert | |
| 6,107,091 A | 8/2000 | Cowsert | |
| 6,180,603 B1 | 1/2001 | Frey, II | |
| 6,291,524 B1 | 9/2001 | Huang et al. | |
| 6,365,354 B1 | 4/2002 | Bennett et al. | |
| 6,410,323 B1 | 6/2002 | Roberts et al. | |
| 6,417,234 B1 | 7/2002 | Huang et al. | |
| 6,437,105 B1 | 8/2002 | Priebe et al. | |
| 6,506,559 B1 | 1/2003 | Fire et al. | |
| 6,566,131 B1 | 5/2003 | Cowsert | |
| 6,566,135 B1 | 5/2003 | Watt | |
| 6,573,099 B2 | 6/2003 | Graham | |
| 2004/0005593 A1 | 1/2004 | Lorens | |
| 2004/0018191 A1 | 1/2004 | Wang et al. | |
| 2004/0175756 A1 | 9/2004 | Kolkman et al. | |
| 2005/0037421 A1 | 2/2005 | Honda et al. | |
| 2005/0048512 A1 | 3/2005 | Kolkman et al. | |
| 2005/0048647 A1 | 3/2005 | Taira et al. | |
| 2005/0053973 A1 | 3/2005 | Kolkman et al. | |
| 2005/0060771 A1 | 3/2005 | Farmer | |
| 2005/0089932 A1 | 4/2005 | Kolkman et al. | |
| 2005/0136063 A1 | 6/2005 | Wang et al. | |
| 2005/0164301 A1 | 7/2005 | Kolkman et al. | |
| 2005/0221384 A1 | 10/2005 | Kolkman et al. | |
| 2006/0141029 A1 | 6/2006 | Heller et al. | |
| 2006/0151574 A1 | 7/2006 | Herget et al. | |
| 2007/0065858 A1 | 3/2007 | Haley | |
| 2007/0099847 A1 | 5/2007 | Goldfine et al. | |
| 2008/0096967 A1 | 4/2008 | Lopez et al. | |
| 2008/0113874 A1 | 5/2008 | Bunn | |
| 2008/0207532 A1 | 8/2008 | Huang et al. | |

FOREIGN PATENT DOCUMENTS

| | | |
|---|---|---|
| DE | 19629652 | 1/1998 |
| EP | 520722 | 12/1992 |
| EP | 566226 | 10/1993 |
| EP | 682027 | 11/1995 |
| EP | 787772 | 8/1997 |
| EP | 837063 | 4/1998 |
| EP | 0404097 | 6/2009 |
| JP | 2-49731 A | 3/1990 |
| JP | 07-133280 | 5/1995 |
| JP | 7-238037 A | 9/1995 |
| JP | 8-337510 A | 12/1996 |
| WO | WO-92-20642 A1 | 11/1992 |
| WO | WO-93-11161 A1 | 6/1993 |
| WO | WO-95-09847 A1 | 4/1995 |
| WO | WO-95-19774 A1 | 7/1995 |
| WO | WO-95-19970 A1 | 7/1995 |
| WO | WO-96-30347 A1 | 10/1996 |
| WO | WO-96-31510 A1 | 10/1996 |

(Continued)

OTHER PUBLICATIONS

Camp et al. (Clin Cancer Res 11:397-405, 2005).*

(Continued)

*Primary Examiner* — Bong-Sook Baek
(74) *Attorney, Agent, or Firm* — Wilson, Sonsini, Goodrich & Rosati

(57) ABSTRACT

The present application relates to compositions and methods for treating a proliferative disorder by administering to a subject a pharmaceutical composition of a dual kinase inhibitor. Catecholic butanes cane serve as dual kinase inhibitors for purposes of methods described herein. Subjects can be further treated by co-administering an EGFR inhibitor. The present application also relates to analyzing a sample with respect to levels of IGF-1R and EGFR and comparing levels of IGF-1R and EGFR to a control. Patients can be selected for treatment with a catecholic butane based on the assessment; optionally, patients can be further treated with an EGFR inhibitor, an IGF-1R inhibitor, or both.

6 Claims, 6 Drawing Sheets

(56) References Cited

FOREIGN PATENT DOCUMENTS

| | | |
|---|---|---|
| WO | WO-96-33980 A1 | 10/1996 |
| WO | WO-96-37201 | 11/1996 |
| WO | WO-97-02266 A1 | 1/1997 |
| WO | WO-97-13771 A1 | 4/1997 |
| WO | WO-97-19065 A1 | 5/1997 |
| WO | WO-97-27199 A1 | 7/1997 |
| WO | WO-97-30034 A1 | 8/1997 |
| WO | WO-97-30044 A1 | 8/1997 |
| WO | WO-97-32880 A1 | 9/1997 |
| WO | WO-97-32881 A1 | 9/1997 |
| WO | WO-97-34895 A1 | 9/1997 |
| WO | WO-97-38983 A1 | 10/1997 |
| WO | WO-97-38994 A1 | 10/1997 |
| WO | WO-97-49688 A1 | 12/1997 |
| WO | WO-98-02434 A1 | 1/1998 |
| WO | WO-98-02437 A1 | 1/1998 |
| WO | WO-98-02438 A1 | 1/1998 |
| WO | WO-98-07726 A1 | 2/1998 |
| WO | WO-98-14449 A1 | 4/1998 |
| WO | WO-98-14451 A1 | 4/1998 |
| WO | WO-98-17662 A1 | 4/1998 |
| WO | WO-98-33787 A1 | 8/1998 |
| WO | WO-99-07701 A1 | 2/1999 |
| WO | WO-99-32619 A1 | 7/1999 |
| WO | WO-99-35132 A1 | 7/1999 |
| WO | WO-99-35146 A1 | 7/1999 |
| WO | WO-00-17203 A1 | 3/2000 |
| WO | WO-00-35455 A1 | 6/2000 |
| WO | WO-00-71129 A1 | 11/2000 |
| WO | WO-01-36646 A1 | 5/2001 |
| WO | WO-01-68836 A2 | 9/2001 |
| WO | WO-02-092599 A1 | 11/2002 |
| WO | WO-02-102804 A1 | 12/2002 |
| WO | WO-02-102805 A1 | 12/2002 |
| WO | WO-03-018021 A1 | 3/2003 |
| WO | WO-03-018022 A1 | 3/2003 |
| WO | WO-03-024967 A2 | 3/2003 |
| WO | WO-03-035614 A2 | 5/2003 |
| WO | WO-03-035615 A2 | 5/2003 |
| WO | WO-03-035616 A2 | 5/2003 |
| WO | WO-03-035619 A2 | 5/2003 |
| WO | WO-03-048133 A1 | 6/2003 |
| WO | WO-03-068265 A1 | 8/2003 |
| WO | WO-2005-037836 A2 | 4/2005 |
| WO | WO-2006-041902 A2 | 4/2006 |
| WO | WO-97-28161 A1 | 8/2007 |
| WO | WO-2008-089388 A2 | 7/2008 |

OTHER PUBLICATIONS

Vippagunta et al, "Crystalline Solids", Advanced Drug Delivery Reviews, vol. 48, pp. 3-26 (2001).*
Gavezzotti, "Are Crystal Structures Predictable?", Accounts of Chemical Research, vol. 27, pp. 309-314 (1994).*
Trisha Gura (Science, 278: 1041-1042, 1997).*
Morgillo et al. (Clin Cancer Res 13(9):2795-2803, May 1, 2007).*
Albert et al., "Pteridine Studies,. Part XXXIX. Pteridines Unsubstituted in teh 4-Position; a New Synthesis from Pyrazines, via 3,4-Dihydropteridines," J. Chem. Soc. 11:1540-1547 (1970).
Avrameas, "Peroxidase labelled antibody and Fab conjugates with enhanced intracellular penetration," Immunochemistry 8:1175-1179 (1975).
Barany, "Genetic disease detection and DNA amplification using cloned thermostable ligase," PNSA USA 88:189-193 (1991).
Baserga, "The IGF-1 Receptor in Cancer Research," Exp. Cell. Res. 253:1-6 (1999).
Berge et al., J. Pharm. Sci. 66:1-19 (1977).
Bird et al., Science 242:423-426 (1988).
Boston-Howes et al., "Nordihydroguaiaretic acid increases glutamate uptake in vitro and in vivo: Therapeutic implications for amyotrophic lateral sclerosis," Exp. Neurol. 213(1):229-237 (2008).
Brem, H. and Gabikian, P. "Biodegradable polymer implants to treat brain tumors," J. Controlled Release 74:63-67 (2001).
Brummelkamp et al., "A System for Stable Expression of Short Interfering RNAs in Mammalian Cells," Science 296:550-553 (2002).
Camirand and Pollak, "Co-targeting IGF-1R and c-kit: synergistic inhibition of proliferation and induction of apoptosis in H209 small cell lung cancer cells," Brit. J. Cancer 90:1825-1829 (2004).
Cole et al., "The EBV-Hybridoma Technique and Its Application to Human Lung Cancer," Monoclonal Antibodies and Cancer Therapy, Alan R. Liss Inc. 1985, pp. 77-96.
Cote et al., "Generation of human monoclonal antibodies reactive with cellular antigens," PNSA USA 80:2026-2030 (1983).
Doctor's Guide, Sep. 28, 1998, pp. 1-3.
Domin et al., "Preferential inhibition of platelet-derived growth factor-stimulated DNA synthesis and protein tyrosine phosphorylation by nordihydroguaiaretic acid," J. Biol. Chem. 269(11):8260-8267 (1994).
Elbashir et al., "Duplexes of 21-nucleotide RNAs mediate RNA interference in cultured mammalian cells," Nature 411:494-498 (2001).
Engvall, "Enzyme-linked immunosorbent assay (ELISA) Quantitative assay of immunoglobulin G," Immunochemistry 8:871-874 (1971).
Fleming, "Pharmacokinetics of the Carmustine Implant," Clin. Pharmacokinet. 41:403-419 (2002).
Fu et al., "New polymeric carriers for controlled drug delivery following inhalation or injection," Biomaterials 23:4425-4433 (2002).
Garcia-Echeverria et al., "In vivo antitumor activity of NVP-AEW541-A novel, potent, and selective inhibitor of the IGF-1R kinase," Cancer Cell 5:231-239 (2004).
Goldstein et al., Biological Efficacy of a Chimeric Antibody to the Epidermal Growth Factor Receptor in a Human Tumor Xenograft Model,: Clin. Cancer Res. 1:1311-1318 (1995).
Guatelli et al., "Isothermal, in vitro amplification of nucleic acids by a multienzyme reaction modeled after retroviral replication," PNAS USA 87:1874-1878 (1990).
Gura, "Systems for Identifying New Drugs Are Often Faulty," Science 278(5340):1041-1042 (1997) (Abstract).
Hage, "Recent advances in chromatographic and electgrophoretic methods for the study of drug-protein interactions," Chromatogr. B. Biomed Sci. Appl. 699(1-2):499-525 (1997).
Hannon, "RNA interference," Nature 418:244-251 (2002).
Heegaard, "Capillary electrophoresis for the study of affinity interactions," J. Mol. Recognit. WInter 11(1-6):141-148 (1998).
Holliger et al., "Diabodies: Small bivalent and bispecific antibody fragments," PNAS USA 90:6444-6448 (1993).
Huang et al., "Epidermal Growth Factor Receptor Blockade with C225 Modultaes Proliferation, Apoptosis, and Radiosensitivity in Squamous Cell Carcinomas of the Head and Neck," Cancer Res. 15:59(8):1935-1940 (1999).
Huse et al., Science 246:1275-1281 (1989).
Huston et al., PNAS USA 85:5879-5883 (1988).
Ibrahim and Yee, "Insulin-Like Growth Factor-1 and Breast Cancer Therapy," Clin. Cancer Res. 11:944s-950s (2005).
Ishikawa et al., "Enzyme-Labeling of Antibodies and Their Fragments for Enzyme Immunoassay and Immunohistochemical Staining," J. Immunoassay 4(3):209-327 (1983).
Jablonski, "The Preparation of Bacterial Luciferase Conjugates for Immunoassay and Application to Rubella Antibody Detection," Anal. Biochem. 148:199-206 (1985).
Jones et al., Nature 321:522-525 (1986).
Kohler and Milstein, Nature 256:495-497 (1975).
Kozbor et al., "The production of monoclonal antibodies from human lymphocytes," Immunol. Today 4:72-79 (1983).
Kwoh et al., "Transcription-based amplification system and detection of amplified human immunodeficiency virus type 1 with a bead-based sandwich hybridization format," PNAS USA 86:1173-1177 (1989).
Larsson et al., "Role of insulin-like growth factor 2 receptor signalling in cancer," Brit. J. Cancer 92:2097-2101 (2005).
Lee et al., "Expression of small interfering RNAs targeted against HIV-1 rev transcripts in human cells," Nat. Biotech. 20:500-505 (2002).

(56) References Cited

OTHER PUBLICATIONS

Lizardi et al., "Exponential amplification of recombinant-RNA hybridization probes," Biotechnology 6:1197-1202 (1988).
McManus and Sharp, "Gene silencing in mammals by small interfering RNAs," Nature Reviews Genetics 3:737-747 (2002).
Mitsiades et al., "Inhibition of the insulin-like growth factor receptor-1 tyrosine kinase activity as a therapeutic strategy for multiple myeloma, other hematologic malignancies, and solid tumors," Cancer Cell 5:221-230 (2004).
Miyagishi et al., "Y6 promoter-driven siRNAs with four uridine 3' overhangs efficiently suppress targeted gene expression in mamalian cells," Nat. Biotech. 20:497-500 (2002).
Modjtahedi et al., "The human EGF receptor as a target for cancer therapy: six new rat mAbs against the receptor on the breast carcinoma MDA-MB 468," Br. J. Cancer 67:247-253 (1993).
Muyldermans et al., "Sequence and structure of VH domain from naturally occurring camel heavy chain immunoglobulins lacking light chains," Protein Engineering 7(9):1129-1133 (1994).
Osborne et al., "Inhibition of Breast Cancer Cell Growth in Vitro by a Tyrosine Kinase Inhibitor," Cancer Res. 52:3636-3641 (1992).
Osbourn et al., Nat. Biotech. 16:778 (1998).
Paddison et al., "Short hairpin RNAs (shRNAs) induce sequence-specific silencing in mammalian cells," Genes Dev. 16:948-958 (2002).
Parrizas et al., "Specific Inhibition of Insulin-Like Growth Factor-1 and Insulin Receptor Tyrosine Kinase Activity and Biological Function by Tyrphostins," Endocrinology 138:1427-1433 (1997).
Paul et al., "Effective expression of small interfering RNA in human cells," Nat. Biotech. 20:505-508 (2002).
Pluckthun in Handbook of Experimental Pharmacology vol. 113, Rosenburg and Moore eds., Springer-Verlag, NY, pp. 269-315 (1994).
Presta, Curr. Op. Struct. Biol. 2:593-596 (1992).
"Protein kinase inhibitor," Wikipedia, The Free Encylopedia http://en.wikipedia.org/wild/Protein_kinase_inhibitor.
Reichmann et al., "Reshaping human antibodies for therapy," Nature 332:323-329 (1988).
Rivas, "New developments in the study of biomolecular associations via sedimentation equilibrium," Trends Biochem. Sci. 18(8):284-287 (1993).
Rheinwald et al., "Epidermal growth factor and the multiplication of cultured human epidermal keratinocytes," Nature 265:421-424 (1977).
Robertson et al., "Overview of tyrosine kinase inhibitors in clinical breast cancer," Endocrine-Related Cancer 12:S135-S144 (2005).
Robins et al., "Synthesis and anticancer activity of nordihydroguaiaretic acid (NDGA) and analogues," Anti-Cancer Drug Design 16:261-270 (2001).
Rodeck et al., "EGF-R dependent regulation of keratinocyte survival," J. Cell Science 110:113-121 (1997).
Rowe et al., "Nordihydroguaiaretic acid, a cytotoxic insulin-like growth factor-I receptor/HER2 inhibitor in trastuzumab-resistant breast cancer," Mol. Cancer Therapeutics 7(7):1900-1908 (2008).
Rozengurt et al., "Preferential Inhibition of Platelet-derived Growth Factor-stimulated DNA Synthesis and Protein Tyrosine Phosphorylation by Nordihydroguaiaretic Acid," J. Biol. Chem. 269(11):8260-8267 (1994).
Seufferlein et al., "Mechanisms of nordiydroguaiaretic acid-induced growth inhibition and apoptosis in human cancer cells," Br. J. Cancer 86:1188-1196 (2002).
Sherwood et al., "Selective inhibition of heregulin-dependent tyrosin phosphorylation and cellular signaling through erbB2, erbB3 and erbB4 by PD 158780 adn a new irreversible inhibitor, PD 183805," Proc. Am. Assoc. Cancer Res. 40:723 (1999).
Silverman et al., "Corrigendum: Multivalent avimer proteins evolved by exon shuffling of a family of human receptor domains," Nat. Biotech.. 24:220 (2006).
Silverman et al., "Multivalent avimer proteins evolved by exon shuffling of a family of human receptor domains," Nat. Biotech. 23:1493-1494 (2005).
Sjolander, "Integrated Fluid Handling System for Biomolecular Interaction Analysis," Anal. Chem. 63:2338-2345 (1991).
Szabo et al., "Surface plasmon resonance and its use in biomolecular interaction analysis (BIA)," Curr. Op. Struct. Biol. 5:699-705 (1995).
Teramoto et at , "Inhibitory Effect of Anti-Epidermal Growth Factor Receptor Antibody on a Human Gastric Cancer," Cancer 77:639-645 (1996).
Therasse et al., J. Natl. Cancer Inst. 92(3):205-216 (2000).
Traxler, "Use of a Pharmacophore Model for the Design of EGFR Tyrosine Kinase Inhibitors: Isoflavones and 3-Phenyl-4(1H)-quinolones," J. Med. Chem. 42:1018-1026 (1999).
Tuschl et al., "Expanding small RNA interference," Nat. Biotech. 20:446-448 (2002).
Tuschl et al., "Targeted mRNA degradation by double-stranded RNA in vitro," Genes Dev. 13(24):3191-3197 (1999).
Vaughan et al., "Human antibodies by design," Nature Biotech. 16:535-539 (1998).
Ward et al., Nature 341:544-546 (1989).
Woodburn et al., "ZD1839, an epidermal growth factor tyrosine kinase inhibitor selected for clinical development,"Proc. Am. Assoc. Cancer Res. 38:633 (1997).
Yang, et al., "Eradication of Established Tumors by a Fully Human Monoclonal Antibody to the Epidermal Growth Factor Receptor without Concimitant Chemotherapy," Cancer Res. 59:1236-1243 (1999).
PCT/US09/63646 Search Report dated Feb. 19, 2010.
U.S. Appl. No. 11/552,686 Office Action mailed Nov. 4, 2009.
U.S. Appl. No. 11/552,686 Office Action mailed Jun. 9, 2009.
U.S. Appl. No. 11/552,686 Office Action mailed May 25, 2009.
U.S. Appl. No. 11/552,686 Office Action mailed Nov. 24, 2008.
Chang et al., "Experimentally-induced prostatic hyperplasia in young beagles: a model to evaluate the chemotherapeutic effects of gossypol," Res Comm Mol Path Pharmacol 92(3):341-360 (1996).
CA 2,742,986 Office action mailed Sep. 11, 2012.
MX/a/2011/004824 office action mailed Sep. 28, 2012.
TW 098137952 Office action mailed Jun. 4, 2012.
Gendreau, et al "Inhibition of the T790M Gatekeeper Mutant of the Epidermal Growth Factor Receptor by EXEL-7647." Clin Cancer Res 2007;13:3713-3723.
Pao, et al., "Acquired Resistance of Lung Adenocarcinomas to Gefitinib or Erlotinib Is Associated with a Second Mutation in the EGFR Kinase Domain." PLoS Med 2(3): e73; pp. 1-10. doi:10.1371/journal.pmed.0020073.

* cited by examiner

CATECHOLIC BUTANES AND USE THEREOF FOR CANCER THERAPY

CROSS-REFERENCE

This application claims the benefit of U.S. Provisional Application No. 61/112,621, filed Nov. 7, 2008, which is incorporated herein by reference in its entirety.

BACKGROUND OF THE INVENTION

Proliferative diseases are a serious threat to modern society. Cancerous growths, including malignant cancerous growth, pose serious challenges for modern medicine due to their unique characteristics. Their characteristics include uncontrollable cell proliferation resulting in, for example, unregulated growth of malignant tissue, an ability to invade local and even remote tissues, lack of differentiation, lack of detectable symptoms and most significantly, the lack of effective therapy and prevention.

Cancer can develop in any tissue of any organ at any age. The etiology of cancer is not clearly defined but mechanisms such as genetic susceptibility, chromosome breakage disorders, viruses, environmental factors and immunologic disorders have all been linked to a malignant cell growth and transformation. Cancer encompasses a large category of medical conditions, affecting millions of individuals worldwide. Cancer cells can arise in almost any organ and/or tissue of the body. Cancer develops when cells in a part of the body begin to grow or differentiate out of control. All cancer types begin with the out-of-control growth of abnormal cells.

Currently, some of the main treatments available are surgery, radiation therapy, and chemotherapy. Surgery is often a drastic measure and can have serious consequences. For example, all treatments for ovarian cancer may result in infertility. Some treatments for cervical cancer and bladder cancer may cause infertility and/or sexual dysfunction. Surgical procedures to treat pancreatic cancer may result in partial or total removal of the pancreas can itself carry significant risks, causing serious adverse effects to the patient. Breast cancer surgery invariably involves removal of part of or the entire breast. Some surgical procedures for prostate cancer carry the risk of urinary incontinence and impotence. The procedures for lung cancer patients often have significant post-operative pain as the ribs must be cut through to access and remove the cancerous lung tissue. In addition, patients who have both lung cancer and another lung disease, such as emphysema or chronic bronchitis, typically experience an increase in their shortness of breath following the surgery.

Worldwide, more than 10 million people are diagnosed with cancer every year and it is estimated that this number will grow to 15 million new cases every year by 2020. Cancer causes six million deaths every year or 12% of the deaths worldwide.

SUMMARY OF THE INVENTION

The embodiments disclosed herein relate generally to methods of treatment of diseases using a catecholic butane or a derivative thereof. Some specific embodiments relate to the use of the catecholic butane nordihydroguaiaretic acid (NDGA) or a salt, solvate, isomer, tautomer, metabolite, analog, or prodrug thereof in treating a proliferative disease.

Provided herein are methods for treating a disease comprising administering an effective amount of one pharmaceutical compound capable of inhibiting the tyrosine kinase activity of both insulin-like growth factor-1 receptor (IGF-1R) and epidermal growth factor receptor (EGFR) (i.e., a dual kinase inhibitor), wherein the pharmaceutical compound is a catecholic butane.

Also provided herein are methods for treating a disease in a subject that has developed resistance to one or more tyrosine kinase inhibitors, for example, one or more EGF-R inhibitors and/or one or more IGF-1R inhibitors, comprising administering an effective amount of a pharmaceutical compound capable of inhibiting the tyrosine kinase activity of both IGF-1R and EGFR (i.e., a single compound that is a dual kinase inhibitor), wherein the pharmaceutical compound is a catecholic butane.

Diseases to be treated using the methods provided herein are proliferative diseases.

A proliferative disease includes, but is not limited to, a malignant, pre-malignant or benign cancer. Cancers to be treated using the disclosed methods include, for example, a solid tumor, a lymphoma or a leukemia. In one embodiment, a cancer can be, for example, a brain tumor (e.g., a malignant, pre-malignant or benign brain tumor such as, for example, a glioblastoma, an astrocytoma, a meningioma, a medulloblastoma or a peripheral neuroectodermal tumor), a carcinoma (e.g., gall bladder carcinoma, bronchial carcinoma, basal cell carcinoma, adenocarcinoma, squamous cell carcinoma, small cell carcinoma, large cell undifferentiated carcinoma, adenomas, cystadenoma, etc.), a basalioma, a teratoma, a retinoblastoma, a choroidea melanoma, a seminoma, a sarcoma (e.g., Ewing sarcoma, rhabdomyosarcoma, craniopharyngeoma, osteosarcoma, chondrosarcoma, myosarcoma, liposarcoma, fibrosarcoma, leimyosarcoma, Askin's tumor, lymphosarcoma, neurosarcoma, Kaposi's sarcoma, dermatofibrosarcoma, angiosarcoma, etc.), a plasmocytoma, a head and neck tumor (e.g., oral, laryngeal, nasopharyngeal, esophageal, etc.), a liver tumor, a kidney tumor, a renal cell tumor, a squamous cell carcinoma, a uterine tumor, a bone tumor, a prostate tumor, a breast tumor including, but not limited to a breast tumor that is Her2- and/or ER- and/or PR-, a bladder tumor, a pancreatic tumor, an endometrium tumor, a squamous cell carcinoma, a stomach tumor, gliomas, a colorectal tumor, a testicular tumor, a colon tumor, a rectal tumor, an ovarian tumor, a cervical tumor, an eye tumor, a central nervous system tumor (e.g., primary CNS lymphomas, spinal axis tumors, brain stem gliomas, pituitary adenomas, etc.), a thyroid tumor, a lung tumor (e.g., non-small cell lung cancer (NSCLC) or small cell lung cancer), a leukemia or a lymphoma (e.g., cutaneous T-cell lymphomas (CTCL), non-cutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma, etc.), a multiple myeloma, a skin tumor (e.g., basal cell carcinomas, squamous cell carcinomas, melanomas such as malignant melanomas, cutaneous melanomas or intraocular melanomas, Dermatofibrosarcoma protuberans, Merkel cell carcinoma or Kaposi's sarcoma), a gynecologic tumor (e.g., uterine sarcomas, carcinoma of the fallopian tubes, carcinoma of the endometrium, carcinoma of the cervix, carcinoma of the vagina, carcinoma of the vulva, etc.), Hodgkin's disease, a cancer of the small intestine, a cancer of the endocrine system (e.g., a cancer of the thyroid, parathyroid or adrenal glands, etc.), a mesothelioma, a cancer of the urethra, a cancer of the penis, tumors related to Gorlin's syndrome (e.g., medulloblastomas, meningioma, etc.), a tumor of unknown origin; or metastases of any thereto.

In another embodiment, the cancer is a lung tumor, a breast tumor, a colon tumor, a colorectal tumor, a head and neck tumor, a liver tumor, a prostate tumor, a glioma, glioblastoma multiforme, a ovarian tumor or a thyroid tumor; or metastases of any thereto.

In yet another embodiment, the cancer is an endometrial tumor, bladder tumor, multiple myeloma, melanoma, renal tumor, sarcoma, cervical tumor, leukemia, and neuroblastoma.

Tumors as provided herein may be primary tumors or metastases.

Proliferative diseases may also be disorders of the skin.

In one aspect, the disorder of the skin is for example, a tumor, actinic keratosis, acne, psoriasis, skin wounds, warts, bacterial infections, fungal infections or viral infections. Viral infections include, but are not limited to, an HIV infection, an HPV infection or an HSV infection.

Provided herein are methods for treating a malignant, pre-malignant or benign cancer, comprising administering an effective amount of a pharmaceutical compound capable of inhibiting the tyrosine kinase activity of both IGF-1R and EGFR (i.e., a single compound that is a dual kinase inhibitor), wherein the pharmaceutical compound is a catecholic butane.

Cancers to be treated using the disclosed methods include, for example, a solid tumor, a lymphoma or a leukemia. In one embodiment, a cancer can be, for example, a brain tumor (e.g., a malignant, pre-malignant or benign brain tumor such as, for example, a glioblastoma, an astrocytoma, a meningioma, a medulloblastoma or a peripheral neuroectodermal tumor), a carcinoma (e.g., gall bladder carcinoma, bronchial carcinoma, basal cell carcinoma, adenocarcinoma, squamous cell carcinoma, small cell carcinoma, large cell undifferentiated carcinoma, adenomas, cystadenoma, etc.), a basalioma, a teratoma, a retinoblastoma, a seminoma, a sarcoma (e.g., Ewing sarcoma, rhabdomyosarcoma, craniopharyngeoma, osteosarcoma, chondrosarcoma, myosarcoma, liposarcoma, fibrosarcoma, leimyosarcoma, Askin's tumor, lymphosarcoma, neurosarcoma, Kaposi's sarcoma, dermatofibrosarcoma, angiosarcoma, etc.), a plasmocytoma, a head and neck tumor (e.g., oral, laryngeal, nasopharyngeal, esophageal, etc.), a liver tumor, a kidney tumor, a renal cell tumor, a squamous cell carcinoma, a uterine tumor, a bone tumor, a prostate tumor, a breast tumor including, but not limited to a breast tumor that is Her2- and/or ER- and/or PR-, a bladder tumor, a pancreatic tumor, an endometrium tumor, a squamous cell carcinoma, a stomach tumor, gliomas, a colorectal tumor, a testicular tumor, a colon tumor, a rectal tumor, an ovarian tumor, a cervical tumor, an eye tumor, a central nervous system tumor (e.g., primary CNS lymphomas, spinal axis tumors, brain stem gliomas, pituitary adenomas, etc.), a thyroid tumor, a lung tumor (e.g., non-small cell lung cancer (NSCLC) or small cell lung cancer), a leukemia or a lymphoma (e.g., cutaneous T-cell lymphomas (CTCL), non-cutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma, etc.), a multiple myeloma, a skin tumor (e.g., basal cell carcinomas, squamous cell carcinomas, melanomas such as malignant melanomas, choroidea melanomas, cutaneous melanomas or intraocular melanomas, Dermatofibrosarcoma protuberans, Merkel cell carcinoma or Kaposi's sarcoma), a gynecologic tumor (e.g., uterine sarcomas, carcinoma of the fallopian tubes, carcinoma of the endometrium, carcinoma of the cervix, carcinoma of the vagina, carcinoma of the vulva, etc.), Hodgkin's disease, a cancer of the small intestine, a cancer of the endocrine system (e.g., a cancer of the thyroid, parathyroid or adrenal glands, etc.), a mesothelioma, a cancer of the urethra, a cancer of the penis, tumors related to Gorlin's syndrome (e.g., medulloblastomas, meningioma, etc.), a tumor of unknown origin; or metastases of any thereto.

In another embodiment, the cancer is a lung tumor, a breast tumor, a colon tumor, a colorectal tumor, a head and neck tumor, a liver tumor, a prostate tumor, a glioma, glioblastoma multiforme, a ovarian tumor or a thyroid tumor; or metastases of any thereto.

In yet another embodiment, the cancer is an endometrial tumor, bladder tumor, multiple myeloma, melanoma, renal tumor, sarcoma, cervical tumor, leukemia, and neuroblastoma.

Tumors as provided herein may be primary tumors or metastases. Cancers may also be epithelial based cancers. In one embodiment, cells of tumors may express EGFR. In another embodiment, cells of tumors may express IGF-1R. In yet another embodiment, cells of tumors may express EGFR and IGF-1R.

Provided herein are methods for treating a disorder of the skin, comprising administering an effective amount of a pharmaceutical compound capable of inhibiting the tyrosine kinase activity of both IGF-1R and EGFR (i.e., a single compound that is a dual kinase inhibitor), wherein the pharmaceutical compound is a catecholic butane.

In one aspect, the disorder of the skin is for example, a tumor, actinic keratosis, acne, psoriasis, skin wounds, warts, bacterial infections, fungal infections or viral infections. Viral infections include, but are not limited to, an HIV infection, an HCV infection, an HBV infection, HPV infection and an HSV infection Skin tumors include, but are not limited to, basal cell carcinomas, squamous cell carcinomas, melanomas, Dermatofibrosarcoma protuberans, Merkel cell carcinoma and Kaposi's sarcoma.

In one aspect, a pharmaceutical composition to be administered to a subject is a catecholic butane.

In one embodiment of the methods described herein, a catecholic butane may have the structure of formula I:

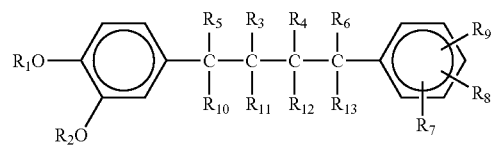

wherein $R_1$ and $R_2$ are independently H, lower alkyl, or lower acyl; $R_3$, $R_4$, $R_5$, $R_6$, $R_{10}$, $R_{11}$, $R_{12}$ and $R_{13}$ are independently H or lower alkyl; and $R_7$, $R_8$ and $R_9$ are independently H, hydroxy, lower alkoxy or lower acyloxy. Also included are pharmaceutically acceptable salts, pharmaceutically acceptable solvates, tautomers, metabolites, and prodrugs of formula I.

In another embodiment of the methods described herein, a catecholic butane may have the structure of formula II:

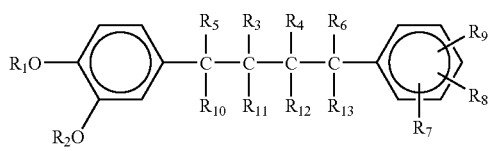

wherein $R_5$, $R_{10}$, $R_6$, and $R_{13}$ are independently H;
when $R_3$ is H, $R_{11}$ is lower alkyl; or when $R_3$ is lower alkyl, $R_{11}$ is H;
when $R_4$ is H, $R_{12}$ is lower alkyl; or when $R_4$ is lower alkyl, $R_{12}$ is H;
two of $R_7$, $R_8$, and $R_9$ are hydroxy, the other is H, and one of the hydroxy groups is in the 3-position and the other hydroxy group is in the 4-position relative to the alkylene substituent. Also included are pharmaceutically acceptable salts, pharmaceutically acceptable solvates, tautomers, metabolites, and prodrugs of formula II.

Non-limiting examples of catecholic butanes for use in the present methods include, for example, NDGA, tetra-O-methyl NDGA; tetraglycinyl NDGA; tetra-dimethylglycinyl NDGA or a salt thereof and tri-O-methyl NDGA; nordihydroguaiaretic acid tetrapivalate; nordihydroguaiaretic acid tetrapropionate and all optical configurations thereof.

Non-limiting examples of catecholic butanes for use in the present methods also include, for example, the d-, l-, racemic mixture of d- and l-, and meso-isomers of 1,4-bis(3,4-dihydroxphenyl)-2,3-dimethylbutane; 1,4-bis(3,4-dihydroxyphenyl)butane; 1,4-bis(3,4-dimethoxyphenyl)-2,3-dimethylbutane; 1,4-bis(3,4-diethoxyphenyl)-2,3-dimethylbutane; 1,4-bis(3,4-dipropoxyphenyl)-2,3-dimethylbutane; 1-(3,4-dihydroxyphenyl)-4-(3,4,5-trihydroxyphenyl) butane; 1,4-bis(3,4-diacetoxyphenyl)-2,3-dimethylbutane; 1,4-bis(3,4-dipropionyloxyphenyl)-2,3-dimethylbutane; 1,4-bis(3,4-dibutyroyloxyphenyl)-2,3-dimethylbutane; 1,4-bis(3,4-divaleroyloxyphenyl)-2,3-dimethylbutane; 1,4-bis(3,4-dipivaloyloxyphenyl)-2,3-dimethylbutane; 1,4-bis(3,4-dineopentylcarboxylphenyl)-2,3-dimethylbutane; or 1-(3,4-dihydroxyphenyl)-4-phenylbutane; and 1-(3,4-dihydroxyphenyl)-4-(2,5-dihydroxyphenyl) butane.

In one embodiment, the catecholic butane is nordihydroguaiaretic acid (NDGA).

Pharmaceutical compositions of the present embodiments may be formulated for any route of administration such as, for example, intranasal administration; oral administration; inhalation administration; subcutaneous administration; transdermal administration; intra-arterial administration, with or without occlusion; intracranial administration; intraventricular administration; intravenous administration; buccal administration; intraperitoneal administration; intraocular administration; intramuscular administration; implantation administration; and central venous administration. In one embodiment, the catecholic butane is formulated for oral administration. In another embodiment, the catecholic butane is formulated for intravenous administration.

Doses of catecholic butanes may be determined using empirical means. By way of example only, catecholic butanes may be administered in an amount of about 5 mg/kg to about 375 mg/kg per dose; about 5 mg/kg to about 250 mg/kg per dose; about 5 mg/kg to about 200 mg/kg per dose; about 5 mg/kg to about 150 mg/kg per dose; about 5 mg/kg to about 100 mg/kg per dose; about 5 mg/kg to about 75 mg/kg per dose; or about 5 mg/kg to about 50 mg/kg per dose. Alternatively, catecholic butanes may be administered in an amount of from about 1,500 mg per day to about 2,500 mg per day; from about 1,800 mg per day to about 2,300 mg per day; or about 2,000 mg per day. In one embodiment, a catecholic butane may be contacted with target cells in a concentration in a range of about 1 µM to about 30 µM. In another embodiment, a catecholic butane may be contacted with target cells in a concentration in a range of about 1 µM to about 10 µM.

In one embodiment, a pharmaceutical composition may be administered more frequently than once every 6 days for a period of time, or more frequently than once every 2 days for a period of time. In one embodiment, a pharmaceutical composition is administered daily for four weeks. In another embodiment, a pharmaceutical composition is administered three times daily for three weeks with a one week hiatus prior to starting a new cycle. In another embodiment, a pharmaceutical composition is administered daily for one week followed by a one week hiatus. In another embodiment, a pharmaceutical composition is administered daily for two weeks followed by a two week hiatus. In another embodiment, a pharmaceutical composition is administered one time or two times daily continuously or with a one week hiatus prior to starting a new cycle. In yet another embodiment, a pharmaceutical composition is administered one time per week or two times per week.

In any of such methods provided herein, a subject being administered a catecholic butane may be further administered one or more additional anti cancer agents or treatment regimens. Anti-cancer agents include, but are not limited to, DNA damaging agents, topoisomerase inhibitors and mitotic inhibitors. In some embodiments, the one or more anti-cancer agents to be administered may be an EGFR inhibitor, an IGF-1R inhibitor, or both.

In one aspect of the methods described herein, a patient being administered a catecholic butane may be further treated by administering an EGFR inhibitor, an IGF-1R inhibitor, or both.

In one embodiment, the subject to be treated may be resistant to treatment with one or more tyrosine kinase inhibitors, for example, an EGFR inhibitor alone, an IGF-1R inhibitor alone, or an EGFR inhibitor and an IGF-1R inhibitor.

Provided herein are methods of screening of subjects for levels of IGF-1R and EGFR tyrosine kinase activity, comprising: (i) analyzing a sample obtained from a subject comprising measuring levels of IGF-1R and EGFR; and (ii) comparing the levels of the IGF-1R and EGFR in the sample to the levels in a control.

Provided herein are methods for determining a disease treatment, comprising: (i) analyzing a sample obtained from a subject comprising measuring levels of IGF-1R and EGFR, and (ii) comparing the levels of the IGF-1R and EGFR in the sample to the levels in a control; wherein increased levels of IGF-1R, EGFR, or both as compared to the control indicate that the subject is to be treated with a dual tyrosine kinase inhibitor (i.e., a single compound that inhibits both IGF-1R and EGFR). In one embodiment, the dual tyrosine kinase inhibitor is a catecholic butane such as described herein.

In one embodiment, the level of EGFR expression is at baseline levels or greater than baseline levels and the level of IGF-1R expression is at baseline levels or greater than baseline levels. In another embodiment, the level of EGFR expression is at baseline levels and the level of IGF-1R expression is at 2× greater than baseline levels or more. In another embodiment, the level of IGF-1R expression is at baseline levels and the level of EGFR expression is at 2× greater than baseline levels or more. In yet another embodiment, the level of IGF-1R expression is at 2× greater than baseline levels or more and the level of EGFR expression is at 2× greater than baseline levels or more.

Messenger RNA (mRNA) levels of IGF-1R and EGFR may by analyzed using assays such as, for example, reverse transcriptase—polymerase chain reaction (RT-PCR), Northern hybridization, in situ hybridization and quantitative RT-PCR (qRT-PCR).

Protein levels of IGF-1R and EGFR may be analyzed using assays such as, for example, an enzyme linked immunosorbent assay (ELISA), a Western blot, immunohistochemistry, immunoprecipitation, immunofluorescence, enzyme immunoassay (EIA) and radioimmunoassay (RIA).

Genomic DNA levels of IGF-1R and EGFR may be analyzed using, for example, Southern hybridization or gene chips.

In one aspect, IGF-1R and EGFR may be analyzed by (a) introducing into a subject a labeled antibody directed against IGF-1R and labeled antibody directed against EGFR and (b) detecting said labeled antibodies by standard imaging techniques. An antibody can be labeled with a radioactive marker whose presence and location in a subject can be detected by standard imaging techniques. In one embodiment, the radioactive marker is different for an antibody directed against IGF-1R and an antibody directed against EGFR.

In one aspect, the method may further comprise administering to the subject a pharmaceutical compound capable of inhibiting the tyrosine kinase activity of IGF-1R and EGF-R, wherein said pharmaceutical compound is a catecholic butane that inhibits IGF-1R and EGFR (i.e., a dual kinase inhibitor).

In any of such methods provided herein, a subject may be further administered one or more additional anti cancer agents and/or treatment regimens. Anti-cancer agents include, but are not limited to, DNA damaging agents, topoisomerase inhibitors and mitotic inhibitors. In one embodiment, the one or more anti-cancer agents is an EGFR inhibitor, an IGF-1R inhibitor, or both.

In one aspect of the methods described herein, a patient may be further treated by administering an EGFR inhibitor, an IGF-1R inhibitor, or both. In one embodiment, the subject to treated may be resistant to treatment with an EGFR inhibitor alone, an IGF-1R inhibitor alone, or an EGFR inhibitor and an IGF-1R inhibitor.

In one aspect, the subject to be treated has a proliferative disease as described above.

Provided herein are methods of selecting a subject for treatment with a catecholic butane capable of inhibiting the tyrosine kinase activity of IGF-1R and EGF-R (i.e., a dual kinase inhibitor), wherein said subject is identified as having levels of IGF-1R , EGFR, or both at baseline levels or at 2× greater than baseline levels as compared to control levels.

In one aspect, a subject has been previously treated with an EGFR inhibitor or an IGF-1R inhibitor.

In another aspect, the subject may be resistant to treatment with at least one tyrosine kinase inhibitor, for example, an EGFR inhibitor and/or an IGF-1R inhibitor.

In one aspect, a pharmaceutical composition to be administered to a subject is a catecholic butane. Routes of administration, doses and schedules of administration of catecholic butanes have been described above.

In any of such methods provided herein, a subject may be further administered one or more additional anti cancer agents and/or treatment regimens. Anti-cancer agents include, but are not limited to, DNA damaging agents, topoisomerase inhibitors and mitotic inhibitors. In one embodiment, the one or more anti-cancer agents to be administered is an EGFR inhibitor, an IGF-1R inhibitor, or both.

In one aspect of the methods described herein, a patient may be further treated by administering an EGFR inhibitor, an IGF-1R inhibitor, or both. In one embodiment, the subject to be treated may be resistant to treatment with at least one tyrosine kinase inhibitor, for example, an EGFR inhibitor alone, an IGF-1R inhibitor alone, or an EGFR inhibitor and an IGF-1R inhibitor.

In one aspect, the subject (patient) to be treated has a proliferative disease such as those described herein.

In one embodiment, the level of EGFR expression is at baseline levels or greater than baseline levels and the level of IGF-1R expression is at baseline levels or greater than baseline levels. In another embodiment, the level of EGFR expression is at baseline levels and the level of IGF-1R expression is at 2× greater than baseline levels or more. In another embodiment, the level of IGF-1R expression is at baseline levels and the level of EGFR expression is at 2× greater than baseline levels or more. In yet another embodiment, the level of IGF-1R expression is at 2× greater than baseline levels or more and the level of EGFR expression is at 2× greater than baseline levels or more.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the embodiments are set forth with particularity in the appended claims. A better understanding of the features and advantages of the present embodiments will be obtained by reference to the following detailed description that sets forth illustrative embodiments, in which the principles of the embodiments are utilized, and the accompanying drawings of which:

DETAILED DESCRIPTION OF THE INVENTION

Definitions

Figure 1:
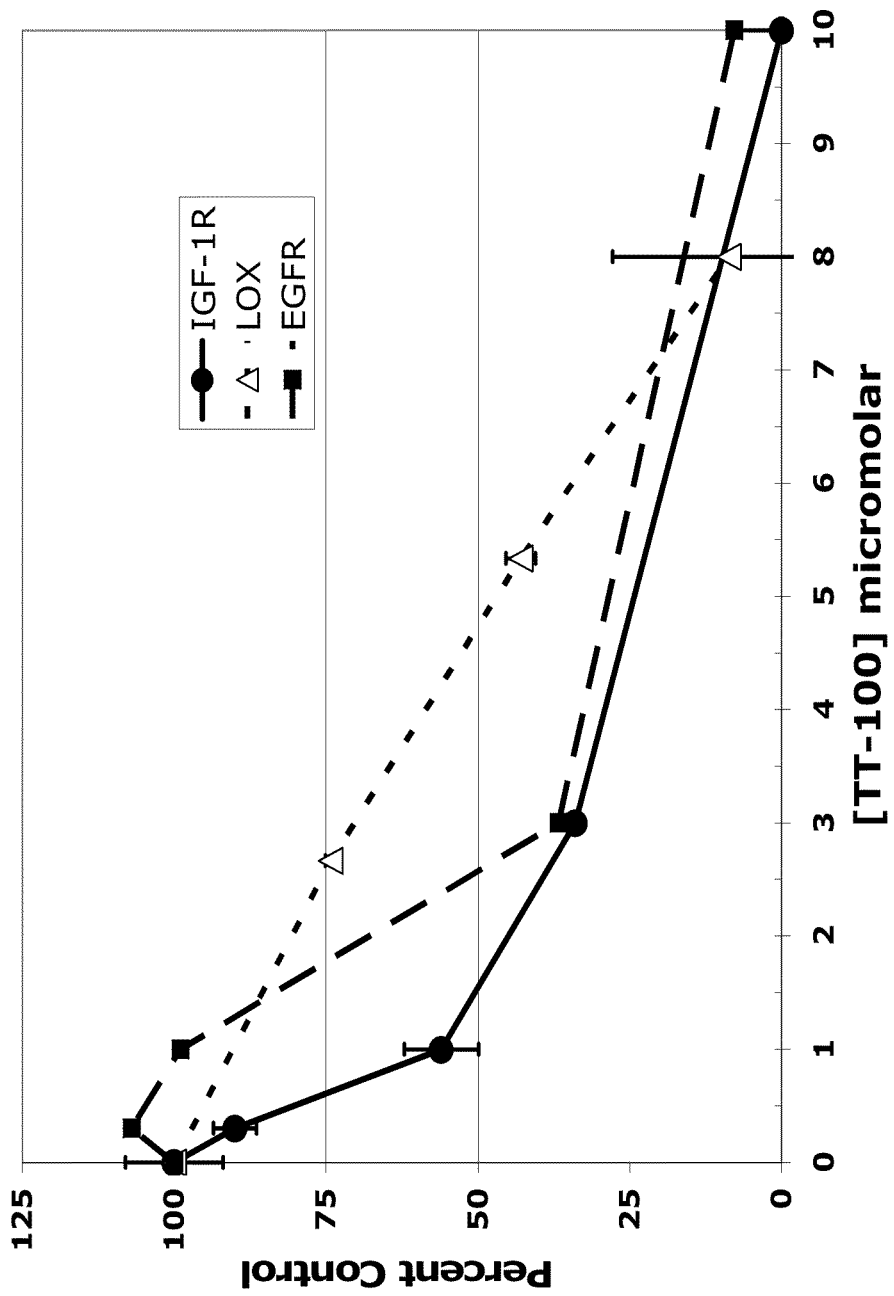
FIG. 1 demonstrates that NDGA (TT-100) directly inhibits the tyrosine kinase activity of both purified IGF-1R and EGFR with greater affinity than its actions against purified lipoxygenase (LOX).

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. It should also be noted that use of "or" means "and/or" unless stated otherwise. Furthermore, use of the term "including" as well as other forms, such as "include," "includes," and "included" is not limiting.

The term "solid tumor" refers to tumors in which a plurality of tumor cells are associated with one another, i.e. contiguous and localized within a confined site. This is to be contrasted with "fluid" or "hematogenous" tumors in which the tumor cells occur primarily as unassociated or individual cells, e.g. leukemia. Solid tumors generally propagate on host tissues such as the epithelial, the connective and supportive tissues as well as other tissues located throughout the body.

"Surgery" means any therapeutic or diagnostic procedure that involves methodical action of the hand or of the hand with an instrument, on the body of a human or other mammal, to produce a curative, remedial, or diagnostic effect.

"Radiation therapy" means exposing a patient to high-energy radiation, including without limitation x-rays, gamma rays, and neutrons. This type of therapy includes without limitation external-beam therapy, internal radiation therapy, implant radiation, brachytherapy, systemic radiation therapy, and radiotherapy.

"Chemotherapy" means the administration of one or more anti-cancer drugs such as, antineoplastic chemotherapeutic agents, chemopreventative agents, and/or other agents to a cancer patient by various methods, including intravenous, oral, intramuscular, intraperitoneal, intravesical, subcutaneous, transdermal, buccal, or inhalation or in the form of a suppository. Chemotherapy may be given prior to surgery to shrink a large tumor prior to a surgical procedure to remove it, after surgery or radiation therapy to prevent the growth of any remaining cancer cells in the body.

The terms "effective amount" or "pharmaceutically effective amount" refer to a nontoxic but sufficient amount of the agent to provide the desired biological, therapeutic, and/or prophylactic result. That result can be reduction and/or alleviation of the signs, symptoms, or causes of a disease, or any other desired alteration of a biological system. For example, an "effective amount" for therapeutic uses is the amount of catecholic butane as disclosed herein per se or a composition comprising the catecholic butane herein required to provide a therapeutically significant decrease in a disease. An appropriate effective amount in any individual case may be determined by one of ordinary skill in the art using routine experimentation.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

The term "treating" and its grammatical equivalents as used herein include achieving a therapeutic benefit and/or a prophylactic benefit. By therapeutic benefit is meant eradication or amelioration of the underlying disorder being treated. Treating also refers to obtaining a desired pharmacologic and/or physiologic effect. The effect may be prophylactic in terms of completely or partially preventing a condition or disease or symptom thereof and/or may be therapeutic in terms of a partial or complete cure for a condition or disease and/or adverse affect attributable to the condition or disease. "Treatment," thus, for example, covers any treatment of a condition or disease in a mammal, particularly in a human, and includes: (a) preventing the condition or disease from occurring in a subject which may be predisposed to the condition or disease but has not yet been diagnosed as having it; (b) inhibiting the condition or disease, such as, arresting its development; and (c) relieving, alleviating or ameliorating the condition or disease, such as, for example, causing regression of the condition or disease. By way of example only, in a cancer patient, therapeutic benefit may include eradication or amelioration of the underlying cancer. Also, a therapeutic benefit may be achieved with the eradication or amelioration of one or more of the physiological symptoms associated with the underlying disorder such that an improvement is observed in the patient, notwithstanding the fact that the patient may still be afflicted with the underlying disorder. For prophylactic benefit, a method may be performed on, or a composition administered to a patient at risk of developing cancer, or to a patient reporting one or more of the physiological symptoms of such conditions, even though a diagnosis of the condition may not have been made. In some instances, treating means stasis (i.e., that the disease does not get worse) and survival of the patient is prolonged. A dose to be administered depends on the subject to be treated, such as the general health of the subject, the age of the subject, the state of the disease or condition, the weight of the subject, the size of a tumor, for example.

The term "subject," "patient" or "individual" as used herein in reference to individuals suffering from a disorder, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In some embodiments of the methods and compositions provided herein, the mammal is a human.

As used herein, the terms "co-administration," "administered in combination with" and their grammatical equivalents or the like are meant to encompass administration of the selected therapeutic agents to a single patient, and are intended to include treatment regimens in which the agents are administered by the same or different route of administration or at the same or different times. In some embodiments, an inhibitor will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, an inhibitor and the other agent(s) are administered in a single composition. In some embodiments, an inhibitor and the other agent(s) are admixed in the composition. In further embodiments, an inhibitor and the other agent(s) are administered at separate times in separate doses.

The term "pharmaceutical composition," as used herein, refers to a biologically active compound, optionally mixed with at least one pharmaceutically acceptable chemical component, such as, though not limited to carriers, stabilizers, diluents, dispersing agents, suspending agents, thickening agents, and/or excipients.

The term "carrier" as used herein, refers to relatively nontoxic chemical compounds or agents that facilitate the incorporation of the compound into cells or tissues.

The term "pharmaceutically acceptable excipient," includes vehicles, adjuvants, or diluents or other auxiliary substances, such as those conventional in the art, which are readily available to the public. For example, pharmaceutically acceptable auxiliary substances include pH adjusting and buffering agents, tonicity adjusting agents, stabilizers, wetting agents and the like.

The term "metabolite," as used herein, refers to a derivative of the compound which is formed when the compound is metabolized.

The term "active metabolite," as used herein, refers to a biologically active derivative of the compound that is formed when the compound is metabolized.

The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to the compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from The Pharmacological Basis of Therapeutics, 9th Edition, McGraw-Hill (1996).

The term "unit dosage form," as used herein, refers to physically discrete units suitable as unitary dosages for human and animal subjects, each unit containing a predetermined quantity of API calculated in an amount sufficient to produce the desired effect in association with a pharmaceutically acceptable diluent, carrier or vehicle. The specifications for the novel unit dosage forms of the present compounds depend on the particular compound employed and the effect to be achieved, and the pharmacodynamics associated with each compound in the host.

As used herein, "percent," "percentage" or the symbol "%" means the percent of the component indicated in the composition based on the amount of the carrier present in the composition, on a weight/weight (w/w), weight/volume (w/v) or volume/volume (v/v), as indicated with respect to any particular component, all based on the amount of the carrier present in the composition. Thus, different types of carriers may be present in an amount of up to 100% as indicated, which does not preclude the presence of the API, the amount of which may be indicated as a % or as a certain number of mg present in the composition or a certain number of mg/mL present, where the % or mg/mL is based on the amount of the total carrier present in the composition. Certain types of carriers may be present in combination to make up 100% of the carrier.

A "substantially purified" compound in reference to the catecholic butanes or NDGA compounds or derivatives is one that is substantially free of materials that are not the catecholic butane, NDGA compounds or NDGA derivatives. By way of example, substantially free is meant at least about 50% free of non-NDGA materials, at least about 70%, at least about 80%, at least about 90% free or at least about 95% free of non-NDGA materials.

The term "tumor cell antigen" is defined herein as an antigen that is present in higher quantities on a tumor cell or in body fluids than unrelated tumor cells, normal cells, or in normal body fluid. The antigen presence may be tested by any number of assays known to those skilled in the art and include without limitation negative and/or positive selection with antibodies, such as an ELISA assay, a radioimmunoassay, or by Western Blot.

"Apoptosis inducing agent" is defined herein to induce apoptosis/programmed cell death, and include, for example, anticancer agents and treatments wherein cells (e.g., tumor cells) are induced to undergo programmed cell death. Exemplary apoptosis inducing agents are described in more detail below.

The terms "apoptosis" or "programmed cell death," refers to the physiological process by which unwanted or useless cells are eliminated during development and other normal biological processes. Apoptosis is a mode of cell death that occurs under normal physiological conditions and the cell is an active participant in its own demise ("cellular suicide"). It is most often found during normal cell turnover and tissue homeostasis, embryogenesis, induction and maintenance of immune tolerance, development of the nervous system and endocrine-dependent tissue atrophy. Cells undergoing apoptosis show characteristic morphological and biochemical features. These features include chromatin aggregation, nuclear and cytoplasmic condensation, partition of cytoplasm and nucleus into membrane bound vesicles (apoptotic bodies), which contain ribosomes, morphologically intact mitochondria and nuclear material. In vivo, these apoptotic bodies are rapidly recognized and phagocytized by macrophages, dendritic cells or adjacent epithelial cells. Due to this efficient mechanism for the removal of apoptotic cells in vivo no inflammatory response is elicited. In vitro, the apoptotic bodies as well as the remaining cell fragments ultimately swell and finally lyse. This terminal phase of in vitro cell death has been termed "secondary necrosis." Apoptosis can be measured by methods known to those skilled in the art like DNA fragmentation, exposure of Annexin V, activation of caspases, release of cytochrome c, etc. A cell that has been induced to die is termed herein as an "apoptotic cell."

Apoptosis can also be tested using a standard Annexin V Apoptosis Assay: NIH:OVCAR-3 cells are grown in 6-well plates (NUNC) and irradiated or treated with an antagonist (or in combination with another anti-cancer drug) for 4-48 hours, washed and stained with Annexin V-FITC (BD-Pharmingen) for 1 hour. Cells are analyzed by flow cytometry (Becton-Dickinson, CellQuest), counterstained with Propidium Iodide and analyzed again in the flow cytometer.

Catecholic Butanes

As used herein, the term "catecholic butane" refers to compounds that are dual kinase inhibitors of both EGFR and IGF-1R (i.e., a single compound that is a dual kinase inhibitor).

In one embodiment, a catecholic butane may have the structure of formula I:

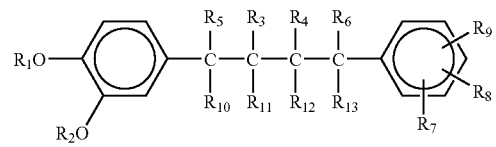

wherein $R_1$ and $R_2$ are independently H, lower alkyl, or lower acyl; $R_3$, $R_4$, $R_5$, $R_6$, $R_{10}$, $R_{11}$, $R_{12}$ and $R_{13}$ are independently H or lower alkyl; and $R_7$, $R_8$ and $R_9$ are independently H, hydroxy, lower alkoxy or lower acyloxy. Also included are pharmaceutically acceptable salts, pharmaceutically acceptable solvates, tautomers, metabolites, and prodrugs of formula I.

In another embodiment, a catecholic butane may have the structure of formula II:

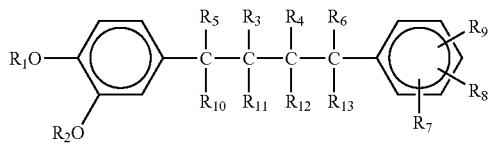

wherein $R_5$, $R_{10}$, $R_6$, and $R_{13}$ are independently H;

when R3 is H, R11 is lower alkyl; or when R3 is lower alkyl, R11 is H;

when R4 is H, R12 is lower alkyl; or when R4 is lower alkyl, $R_{12}$ is H;

two of R7, R8, and R9 are hydroxy, the other is H, and one of the hydroxy groups is in the 3-position and the other hydroxy group is in the 4-position relative to the alkylene substituent. Also included are pharmaceutically acceptable salts, pharmaceutically acceptable solvates, tautomers, metabolites, and prodrugs of formula II.

As used herein, lower alkyl is intended to generally mean $C_1$-$C_6$ alkyl, and preferably $R_3$ and $R_4$ are $C_1$-$C_3$ alkyl. As used herein, lower alkyl also represents, inter alia, methyl, ethyl, n-propyl, isopropyl, n-butyl, iso-butyl, tert-butyl, n-pentyl, isopentyl, n-hexyl, and the like.

As used herein, lower acyl is intended to generally mean [$C_1$-$C_6$] acyl, with [$C_2$-$C_6$] acyl being preferred. As used herein, lower acyl also represents groups having the general formula RCO—, e.g., acetyl($CH_3CO$—), propionyl ($CH_3CH_2CO$—), butyryl(CH $CH_2CH_2CO$—), and the like.

Catecholic butanes may be directed to both the phenolic compounds and the conventional esters and ethers thereof. When the catecholic butane compound is, for example, a substituted phenyl, the corresponding groups are acetoxy ($CH_3CO_2$—), propionyloxy($CH_3CH_2CO_2$—), and butyroyloxy($CH_3CH_2CH_2CO_2$—).

Compounds may be in the form of a single optical isomer or a mixture of such isomers, e.g., a racemic mixture, or diastereoisomers.

In one embodiment, the catecholic butane is nordihydroguaiaretic acid (NDGA) or a derivative thereof. NDGA is a phenolic compound that was identified as a major component of a tea made from resinous extracts of the creosote bush *Larrea divaricatta*.

Non-limiting examples of catecholic butanes for use in the present methods include, but are not limited to, NDGA, tetra-O-methyl NDGA; tetraglycinyl NDGA; tetra-dimethylglycinyl NDGA or a salt thereof; or tri-O-methyl NDGA; nordihydroguaiaretic acid tetrapivalate; nordihydroguaiaretic acid tetrapropionate and all optical configurations thereof.

Non-limiting examples of catecholic butanes for use in the present methods also include, for example, the d-, l-, racemic mixture of d- and l-, and meso-isomers of 1,4-bis(3,4-dihydroxphenyl)-2,3-dimethylbutane; 1,4-bis(3,4-dihydroxyphenyl)butane; 1,4-bis(3,4-dimethoxyphenyl)-2,3-dimethylbutane; 1,4-bis(3,4-diethoxyphenyl)-2,3-dimethylbutane; 1,4-bis(3,4-dipropoxyphenyl)-2,3-dimethylbutane; 1-(3,4-dihydroxyphenyl)-4-(3,4,5-trihydroxyphenyl) butane; 1,4-bis(3,4-diacetoxyphenyl)-2,3-dimethylbutane; 1,4-bis(3,4-dipropionyloxyphenyl)-2,3-dimethylbutane; 1,4-bis(3,4-dibutyroyloxyphenyl)-2,3-dimethylbutane; 1,4-bis(3,4-divaleroyloxyphenyl)-2,3-dimethylbutane; 1,4-bis(3,4-dipivaloyloxyphenyl)-2,3-dimethylbutane; 1,4-bis(3,4-dineopentylcarboxylphenyl)-2,3-dimethylbutane; or 1-(3,4-dihydroxyphenyl)-4-phenylbutane; and 1-(3,4-dihydroxyphenyl)-4-(2,5-dihydroxyphenyl) butane.

Other catecholic butanes described in the art are contemplated for use herein. Catecholic butanes described in, for example, U.S. Pat. Nos. 5,008,294; 6,291,524; or 6,417,234; U.S. Published Application Nos. 20080207532, 20080096967, 20060151574, 20060141029 and 20070099847 are incorporated herein by reference.

Definition of standard chemistry terms may be found in reference works, including Carey and Sundberg "Advanced Organic Chemistry 4th Ed." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

The compounds presented herein may exist as tautomers. Tautomers are compounds that are interconvertible by migration of a hydrogen atom, accompanied by a switch of a single bond and adjacent double bond. In solutions where tautomerization is possible, a chemical equilibrium of the tautomers will exist. The exact ratio of the tautomers depends on several factors, including temperature, solvent, and pH. Some examples of tautomeric pairs include:

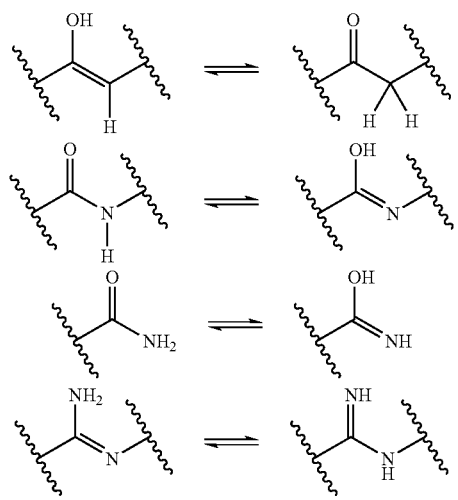

The term "pharmaceutically acceptable derivative or prodrug" as used herein, refers to any pharmaceutically acceptable salt, ester, salt of an ester or other derivative of a compound, which, upon administration to a recipient, is capable of providing (either directly or indirectly) a pharmaceutically active metabolite or residue thereof. Particularly favored derivatives or prodrugs are those that increase the bioavailability of the compounds when such compounds are administered to a patient (e.g., by allowing orally administered compound to be more readily absorbed into blood) or which enhance delivery of the parent compound to a biological compartment (e.g., the brain or lymphatic system).

The term "pharmaceutically acceptable salt" as used herein, refers to salts that retain the biological effectiveness of the free acids and bases of the specified compound and that are not biologically or otherwise undesirable. Compounds described herein may possess acidic or basic groups and therefore may react with any of a number of inorganic or organic bases, and inorganic and organic acids, to form a pharmaceutically acceptable salt. These salts can be prepared in situ during the final isolation and purification of the compounds, or by separately reacting a purified compound in its free base form with a suitable organic or inorganic acid, and isolating the salt thus formed. Examples of pharmaceutically acceptable salts include those salts prepared by reaction of the compound with a mineral or organic acid or an inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate, metaphosphate, methanesulfonate, methoxybenzoate, methylbenzoate, monohydrogen phosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate and xylenesulfonate. Other acids, such as oxalic, while not in themselves pharmaceutically acceptable, may be employed in the preparation of salts useful as intermediates in obtaining the compounds described herein and their pharmaceutically acceptable acid addition salts. See, for example, Berge et al., J. Pharm. Sci. 1977, 66, 1-19. Further, those compounds described herein which may comprise a free acid group may react with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of bases include sodium hydroxide, potassium hydroxide, choline hydroxide, sodium carbonate, N+(C1-4 alkyl)$_4$, and the like. Representative organic amines useful for the formation of base addition salts include ethylamine, diethylamine, ethylenediamine, ethanolamine, diethanolamine, piperazine and the like. It should be understood that compounds also include the quaternization of any basic nitrogen-containing groups they may contain. Water or oil-soluble or dispersible products may be obtained by such quaternization. See, for example, Berge et al., supra.

Catecholic butanes can also exist in various polymorphic states, all of which are herein contemplated, and which can also be useful for treating disorders. For example, polymorphs of catecholic butanes may be administered in embodiments of the methods described herein. Catecholic butanes include, for example, all crystalline forms (known as polymorphs). Polymorphs include the different crystal packing arrangements of the same elemental composition of the compound. Polymorphs can have different X-ray diffraction patterns, infrared spectra, melting points, density, hardness, crystal shape, optical and electrical properties, stability, solvates and solubility. Various factors such as the recrystallization solvent, rate of crystallization, and storage temperature can cause a single crystal form to dominate. The various polymorphs can be administered as pharmaceutical compositions.

In pharmaceutical dosage forms, active agents may be administered in the form of their pharmaceutically acceptable salts, or they may also be used alone or in appropriate association, as well as in combination, with other pharmaceutically active compounds. The following methods and excipients are merely exemplary and are in no way limiting. Methods of preparing various pharmaceutical compositions with a specific amount of active compound are known or will be apparent to those skilled in this art. For examples, see Remington's Pharmaceutical Sciences, Mack Publishing Company, Ester, Pa., 18th Edition (1990).

The pharmaceutically acceptable excipients, such as vehicles, adjuvants, carriers or diluents, are conventional in the art. Suitable excipient vehicles are, for example, water, saline, dextrose, glycerol, ethanol, or the like, and combinations thereof. In addition, if desired, the vehicle may contain minor amounts of auxiliary substances such as pH adjusting and buffering agents, tonicity adjusting agents, stabilizers, wetting agents or emulsifying agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The active agents can be formulated into preparations for injection by dissolving, suspending or emulsifying them in an aqueous or non-aqueous solvent, such as vegetable or other similar oils, including corn oil, castor oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents can be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose, saccharin or aspartame.

Pharmaceutical preparations can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. The formulations can be presented in unit-dose or multi-dose containers, for example sealed ampoules and vials, and can be stored in powder form or in a freeze-dried (lyophilized) condition requiring only the addition of the sterile liquid carrier, for example, saline or sterile pyrogen-free water, immediately prior to use. Extemporaneous injection solutions and suspensions can be prepared from sterile powders, granules and tablets of the kind previously described.

Formulations for parenteral administration include aqueous and non-aqueous (oily) sterile injection solutions of the active compounds which can contain antioxidants, buffers, biocide, bacteriostats and solutes which render the formulation isotonic with the blood of the intended recipient; and aqueous and non-aqueous sterile suspensions which can include suspending agents and thickening agents. Examples of suitable isotonic vehicles for use in such formulations include Sodium Chloride Injection, Ringer's Solution, or Lactated Ringer's Injection. Suitable lipophilic solvents or vehicles include fatty oils such as sesame oil, or synthetic fatty acid esters, such as ethyl oleate or triglycerides, or liposomes or other microparticulate systems can be used to target the compound to blood components or one or more organs. The concentration of the active ingredient in the solution can vary widely. Typically, the concentration of the active ingredient in the solution is from about 1 ng/ml to about 10 µg/ml, for example from about 10 ng/ml to about 1 µg/ml. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions Pharmaceutical preparations can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions can take the form of tablets, lozenges, pastilles, or gels formulated in conventional manner. Such compositions can comprise the active ingredient in a flavored basis such as sucrose and acacia or tragacanth.

Pharmaceutical preparations can be administered topically, that is by non-systemic administration. This includes the application of the compositions externally to the epidermis or the buccal cavity and the instillation of such compound into the ear, eye and nose, such that the compound does not significantly enter the blood stream. In contrast, systemic administration refers to oral, intravenous, intraperitoneal and intramuscular administration.

Pharmaceutical preparations suitable for topical administration include liquid or semi-liquid preparations suitable for penetration through the skin to the site of inflammation such as gels, liniments, lotions, creams, ointments or pastes, suspensions, powders, solutions, spray, aerosol, oil, and drops suitable for administration to the eye, ear or nose. Alternatively, a formulation can comprise a patch or a dressing such as a bandage or adhesive plaster impregnated with active ingredients and optionally one or more excipients or diluents. The amount of active ingredient present in the topical formulation can vary widely. The active ingredient can comprise, for topical administration, from 0.001% to 10% w/w, for instance from 1% to 2% by weight of the formulation. It can however comprise as much as 10% w/w but preferably will comprise less than 5% w/w, more preferably from 0.1% to 1% w/w of the formulation.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations suitable for topical administration to the eye also include eye drops wherein the active ingredient is dissolved or suspended in a suitable carrier, especially an aqueous solvent for the active ingredient.

The active agents can be utilized in aerosol formulation to be administered via inhalation.

The compounds of the present embodiments may be formulated into pressurized acceptable propellants such as dichlorodifluoromethane, propane, nitrogen and the like.

Furthermore, the active agents can be made into suppositories by mixing with a variety of bases such as emulsifying bases or water-soluble bases. The compounds of the present embodiments may be administered rectally via a suppository. The suppository can include vehicles such as cocoa butter, carbowaxes and polyethylene glycols, which melt at body temperature, yet are solidified at room temperature.

For oral preparations, the active agents can be used alone or in combination with appropriate additives to make tablets, powders, granules or capsules with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. For oral rinses, the preparations can be made in a manner conventional in the art.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

Some catecholic butanes are water-soluble, hydrophilic compounds. Some embodiments include formulation of hydrophilic compounds in a pharmaceutically acceptable carrier or excipient and delivery of such as oral formulations, such as in the form of an aqueous liquid solution of the compound, or the compounds can be lyophilized and delivered as a powder, made into a tablet, or the compounds can be encapsulated.

The tablets herein can be enteric coated tablets. The formulations herein can be sustained release, either slow release or rapid release formulations.

The amount of the catecholic butanes be included in the oral formulations can be adjusted depending on the desired dose to be administered to a subject. Such an adjustment is within the skill of persons conventional in the art.

Some catecholic butanes are hydrophobic or lipophilic compounds. The absorption of lipophilic compounds in the gut can be improved by using pharmaceutically acceptable carriers that can enhance the rate or extent of solubilization of the compound into the aqueous intestinal fluid. Lipidic carriers are known in the art. The formulations herein can be delivered as oral liquids or can be encapsulated into various types of capsules.

The present embodiments include, in one example, a formulation containing lipophilic catecholic butanes that are formulated for oral delivery by dissolution of such compounds in triacylglycerols, and the formulation is then encapsulated for oral delivery. Triacyglycerols are molecules with long chain and/or medium chain fatty acids linked to a glycerol molecule. The long chain fatty acids range from about $C_{14}$ to $C_{24}$, and can be found in common fat. The medium chain fatty acids range from about $C_6$ to $C_{12}$, and can be found in coconut oil or palm kernel oil. Triacylglycerols suitable for use herein include structured lipids that contain mixtures of either short-chain or medium chain fatty acids or both, esterified on the same glycerol molecule.

In another embodiment, one or more surfactants can be added to a mixture of catecholic butanes and lipidic carrier such that the drug is present in fine droplets of oil/surfactant mix. The surfactants can act to disperse the oily formulation on dilution in the gastrointestinal fluid.

The present embodiments also include a formulation for oral delivery of the catecholic butanes in the form of a microemulsion consisting of hydrophilic surfactant and oil. The micro-emulsion particles can be surfactant micelles containing solubilized oil and drug.

Formulations suitable for oral administration can be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient can also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets can be made by compression or molding, optionally with one or more accessory ingredients. Compressed tablets can be prepared by compressing in a suitable machine the active ingredient in a free-flowing form such as a powder or granules, optionally mixed with binders (e.g., povidone, gelatin, hydroxypropylmethyl cellulose), inert diluents, preservative, disintegrant (e.g., sodium starch glycolate, cross-linked povidone, cross-linked sodium carboxymethyl cellulose) or lubricating, surface active or dispersing agents. Molded tablets can be made by molding in a suitable machine a mixture of the powdered compound moistened with an inert liquid diluent. The tablets can optionally be coated or scored and can be formulated so as to provide slow or controlled release of the active ingredient therein. Tablets can optionally be provided with an enteric coating, to provide release in parts of the gut other than the stomach. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or Dragee coatings for identification or to characterize different combinations of active compound doses.

Also suitable for oral administration are formulations of the catecholic butanes in a solid lipid nanoparticle preparation. Solid lipid nanoparticles can be prepared in any manner conventional in the art.

In one embodiment, the solid lipid nanoparticle can be prepared in a hot homogenization process by homogenization of melted lipids at elevated temperature. In this process, the solid lipid is melted and the catecholic butane is dissolved in the melted lipid. A pre-heated dispersion medium is then mixed with the drug-loaded lipid melt, and the combination is mixed with a homogenisator to form a coarse pre-emulsion. High pressure homogenization is then performed at a temperature above the lipids melting point to produce a oil/water-nanoemulsion. The nanoemulsion is cooled down to room temperature to form solid lipid nanoparticles.

In another embodiment, the solid lipid nanoparticles can be prepared in a cold homogenization process. In this process, the lipid is melted and the catecholic butane is dissolved in the melted lipid. The drug-loaded lipid is then solidified in liquid nitrogen or dry ice. The solid drug-lipid is ground in a powder mill to form 50-100 µm particles. The lipid particles are then dispersed in cold aqueous dispersion medium and homogenized at room temperature or below to form solid lipid nanoparticles.

Also provided herein, in one example, is a formulation of the lipophilic catecholic butanes in liposomes or micelles for oral delivery. These formulations can be made in any manner conventional in the art. Micelles are typically lipid monolayer vesicles in which the hydrophobic drug associates with the hydrophobic regions on the monolayer. Liposomes are typically phospholipids bilayer vesicles. A lipophilic catecholic butane will typically reside in the center of these vesicles.

Also provided herein, in another example, is a formulation of the catecholic butanes for intravenous administration. Catecholic butanes may be formulated for injection into animals with a pharmaceutically acceptable carrier. Carriers include, but are not limited to one or more solubilizing agents and/or an excipient such as, for example: (a) a water-soluble organic solvent other than dimethyl sulfoxide; provided that when the water-soluble organic solvent is propylene glycol, the propylene glycol is in the absence of white petrolatum, in the absence of xanthan gum (also known as xantham gum and xantham gum) and in the absence of at least one of glycerine or glycine, when the water-soluble organic solvent is polyethylene glycol, the polyethylene glycol is present in the absence of ascorbic acid or butylated hydroxytoluene ("BHT"), and when the polyethylene glycol is polyethylene glycol 400, the polyethylene glycol 400 is present in the absence of polyethylene glycol 8000; (b) a cyclodextrin; (c) an ionic, non-ionic or amphipathic surfactant, provided that when the surfactant is a non-ionic surfactant, the non-ionic surfactant is present in the absence of xanthan gum; (d) a modified cellulose; (e) a water-insoluble lipid other than castor oil; or a combination of any of the carriers (a)-(e).

Pharmaceutical compositions can be in the form of a sterile injectable aqueous solution. Among the acceptable vehicles and solvents that can be employed are water, Ringer's solution and isotonic sodium chloride solution. The sterile injectable preparation can also be a sterile injectable oil-in-water microemulsion where the active ingredient is dissolved in the oily phase. For example, the active ingredient can be first dissolved in a mixture of soybean oil and lecithin. The oil solution then introduced into a water and glycerol mixture and processed to form a microemulsion. The injectable solutions or microemulsions can be introduced into a patient's blood-stream by local bolus injection. Alternatively, it can be advantageous to administer the solution or microemulsion in such a way as to maintain a constant circulating concentration of the instant compound. In order to maintain such a constant concentration, a continuous intravenous delivery device can be utilized. An example of such a device is the Deltec CADD-PLUS™ model 5400 intravenous pump. The pharmaceutical compositions can be in the form of a sterile injectable aqueous or oleaginous suspension for intramuscular and subcutaneous administration. This suspension can be formulated according to the known art using those suitable dispersing or wetting agents and suspending agents which have been mentioned above. The sterile injectable preparation can also be a sterile injectable solution or suspension in a non-toxic parenterally-acceptable diluent or solvent, for example as a solution in 1,3-butanediol. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Also provided herein is a formulation of the catecholic butanes for intra-arterial administration, with or without accompanying blood brain barrier disruption ("BBBD"), and with or without occlusion, such as in hepatic artery chemoemobolization. Briefly, where catecholic butanes are administered intra-arterially with occlusion, primary arteries leading to the target site are catheterized and the catecholic butanes may be applied through a catheter. Embolization of the arteries, in order to retain the catecholic butanes at the target site for a longer period, may be performed using polyvinyl alcohol particles alone or in combination with coils. Intra-arterial delivery of the catecholic butanes may include water soluble compositions. The drugs or agents herein may be dissolved in saline prior to intra-arterial injection and such injection may be preceded by heparin treatment and sedation.

Osmotic disruption of the blood brain barrier ("BBB") as conventional in the art may accompany intra-arterial delivery of the agents herein. Such a procedure can be used to increase the transfer of drugs into the central nervous system ("CNS") preferably just prior to intra-arterial delivery. For such disruption, a catheter is placed into an artery, usually the superficial temporal artery, leading to the brain and the BBB is disrupted with a solution of mannitol. This invasive procedure is typically performed while the patient is under general anesthesia. Such treatment may require prior hydration and administration of anticonvulsants and/or atropine.

Also provided herein, in one example, is a formulation of catecholic butanes for intranasal delivery and intranasal delivery thereof. Intranasal delivery may advantageously build up a higher concentration of the active agents in the brain than can be achieved by intravenous administration. Also, this mode of delivery avoids the problem of first pass metabolism in the liver and gut of the subject receiving the drug.

The amount of the active agents that can be absorbed partly depends on the solubility of the drug in the mucus, a composition that consists of about 95% water solution of serum proteins, glycoproteins, lipids and electrolytes. Generally, as lipophilicity of the active agents herein increases, the drug concentration in the CSF also increases.

Hydrophilic catecholic butanes may be dissolved in a pharmaceutically acceptable carrier such as saline, phosphate buffer, or phosphate buffered saline. In one embodiment, a 0.05 M phosphate buffer at pH 7.4 can be used as the carrier.

Intranasal delivery of the present agents may be optimized by adjusting the position of the subject when administering the agents. For example, the head of the patient may be variously positioned upright-90°, supine-90°, supine-45°, or supine-70° to obtain maximal effect.

The carrier of the composition of catecholic butanes may be any material that is pharmaceutically acceptable and compatible with the active agents of the composition. Where the carrier is a liquid, it can be hypotonic or isotonic with nasal fluids and within the pH of about 4.5 to about 7.5. Where the carrier is in powdered form it is also within an acceptable pH range.

The carrier composition for intranasal delivery may optionally contain lipophilic substances that may enhance absorption of the active agents across the nasal membrane and into the brain via the olfactory neural pathway. Examples of such lipophilic substances include, but are not limited to, gangliosides and phosphatidylserine. One or several lipophilic adjuvants may be included in the composition, such as, in the form of micelles.

The pharmaceutical composition of active agents for intranasal delivery to a subject for treatment of the diseases, disorders, or conditions herein can be formulated in the manner conventional in the art as described in, for example, U.S. Pat. No. 6,180,603 which is incorporated herein by reference. For example, the composition herein can be formulated as a powder, granules, solution, aerosol, drops, nanoparticles, or liposomes. In addition to the active agents, the composition may contain appropriate adjuvants, buffers, preservatives, salts. Solutions such as nose drops may contain anti-oxidants, buffers, and the like.

Catecholic butanes may be delivered to a subject for treatment by surgical implantation into a desired site, such as by implantation of a biodegradable polymer containing the catecholic butane.

Thus, the biodegradable polymer herein can be any polymer or copolymer that would dissolve in the interstitial fluid, without any toxicity or adverse effect on host tissues. Preferably, the polymer or monomers from which the polymer is synthesized is approved by the Food and Drug Administration for administration into humans. A copolymer having monomers of different dissolution properties is preferred so as to control the dynamics of degradation, such as increasing the proportion of one monomer over the other to control rate of dissolution.

In one embodiment, the polymer is a copolymer of 1,3-bis-(p-carboxyphenoxy)propane and sebacic acid [p(CPP:SA)], as described in Fleming A. B. and Saltzman, W. M., Pharmacokinetics of the Carmustine Implant, Clin. Pharmacokinet, 41: 403-419 (2002); and Brem, H. and Gabikian, P. (2001). In another embodiment, the polymer is a copolymer of polyethylene glycol ("PEG") and sebacic acid, as described in Fu, J. et al., (2002) Biomaterials, 23: 4425-4433.

Polymer delivery systems are applicable to delivery of both hydrophobic and hydrophilic catecholic butanes described herein. The catecholic butanes may be combined with the biodegradable polymers and surgically implanted at the desired or affected site. Some polymer compositions are also usable for intravenous or inhalation therapy herein.

Catecholic butanes may be delivered systemically and/or locally by administration to the lungs through inhalation. Inhalation delivery of drugs has been well accepted as a method of achieving high drug concentration in the pulmonary tissues without triggering substantial systemic toxicity, as well as a method of accomplishing systemic circulation of the drug. The techniques for producing such formulations are conventional in the art. Efficacy against pulmonary diseases may be seen with either hydrophobic or hydrophilic catecholic butanes delivered in this manner.

For pulmonary delivery via inhalation, catecholic butanes may be formulated into dry powders, aqueous solutions, liposomes, nanoparticles, or polymers and administered, for example, as aerosols. Hydrophilic formulations may also be taken up through the alveolar surfaces and into the bloodstream for systemic applications.

In one embodiment, the polymers containing the active agents herein are made and used as described in Fu, J. et al. (2002) supra. For example, the polymers herein can be polymers of sebacic acid and polyethylene glycol ("PEG"), or can be poly(lactic-co-glycolic) acid ("PLGA"), or polymers of polyethyleneimine ("PEI") and poly-L-lysine ("PLL").

In another embodiment, catecholic butanes for inhalation delivery may be dissolved in saline or ethanol before nebulization and administered.

In a further embodiment, the agents herein are also effective when delivered as a dry powder, prepared in the manner conventional in the art.

In one embodiment, delivery of the NDGA compounds may be accomplished with the aid of microprocessors embedded into drug delivery devices, such as, for example, SmartMist™ and AERx™.

The appropriate dose to be administered depends on the subject to be treated, such as the general health of the subject, the age of the subject, the state of the disease or condition, the weight of the subject, the size of the tumor, for example.

Pharmaceutical compositions may be formulated for a route of administration such as, for example, intranasal administration; oral administration; inhalation administration; subcutaneous administration; transdermal administration; intra-arterial administration, with or without occlusion; intracranial administration; intraventricular administration; intravenous administration; buccal administration; intraperitoneal administration; intraocular administration; intramuscular administration; implantation administration; and central venous administration. In one embodiment, the catecholic butane is formulated for oral administration. In another embodiment, the catecholic butane is formulated for intravenous administration.

An active agent may be administered in a single or, more typically, multiple doses. Preferred dosages for a given agent are readily determinable by those of skill in the art by a variety of means. Other effective dosages can be readily determined by one of ordinary skill in the art through routine trials establishing dose response curves. The amount of agent will, of course, vary depending upon the particular agent used.

The frequency of administration of the active agent, as with the doses, will be determined by the care giver based on age, weight, disease status, health status and patient responsiveness. Thus, the agents may be administered one or more times daily, weekly, monthly or as appropriate as conventionally determined. The agents may be administered intermittently, such as for a period of days, weeks or months, then not again until some time has passed, such as 3 or 6 months, and then administered again for a period of days, weeks, or months.

Unit dosage forms for injection or intravenous administration may comprise the API in a composition as a solution in sterile water, normal saline or another pharmaceutically acceptable carrier.

Mechanism of Catecholic Butanes

Not intending to be limited by one mechanism of action, the present inventors have discovered that the compounds described herein have anti-proliferative properties via the dual inhibition of both the receptor tyrosine kinases (RTKs) EGFR and IGF-1R. The drug's mechanism of action is related to its ability to act as dual kinase inhibitor of EGFR and IGF-1R.

There are multiple means of interaction between the insulin-like growth factor-1 receptor (IGF-1R) and the epidermal growth factor receptor (EGFR) that together have a significant impact on tumor biology and cancer therapeutics. This interaction comes from a degree of redundancy in their function, with both receptors signaling through shared proliferative and survival pathways. In addition, there exists crosstalk between the two receptor signaling pathways, such that signaling through one receptor can activate the other receptor through ligand-dependent or independent mechanisms.

This redundancy and cross talk presents significant problems for targeted anti-cancer therapeutics. Interventions targeted toward blocking the EGFR function can be limited in efficacy in cells for which activated IGF-1R signaling can activate many of the down stream effector molecules involved in mediating the EGFR effects. Reduced sensitivity to IGF-1R inhibition can also be due to increased EGFR expression or activity. More importantly, the drug resistance that develops to EGFR and HER2 treatment is associated with an upregulation of the IGF-1R signaling pathway. This enhancement in IGF-1R signaling can circumvent EGFR inhibition by providing alternative proliferation and survival signals, and also by increasing production of EGFR ligands or independently stimulating EGFR activation via direct phosphorylation.

The role of IGF-1R in developed resistance to EGFR targeting agents suggests both a promising new therapy for drug resistant populations, and an improved strategy for treating tumors driven by EGFR activity. In support of this approach, cell lines with developed resistance to Gefitinib (Iressa®) display an upregulation of IGF-1R signaling and an increased sensitivity to IGF-1R targeted therapies.

Although NDGA is known predominantly as an inhibitor of 5' and 12' lipoxygenase enzymes, the present inventors have shown that this molecule directly inhibits the tyrosine kinase activity of purified IGF-1R and EGFR with greater affinity than its actions against purified lipoxygenase. See FIG. 1. NDGA is therefore a promising agent for the treatment of tumors overexpressing EGFR and IGF-1R to prevent circumvention of EGFR-only targeting or IGF-1R-only targeting. NDGA is also a promising agent in patients with resistance to Gefitinib (Iressa®) therapy.

Inhibiting the activity of EGFR and/or IGF-1R includes reducing the activity of these molecules. The term "inhibits" and its grammatical conjugations, such as "inhibitory," is not intended to require complete reduction in EGFR and/or IGF-1R activity. Such reduction may be by at least about 10%, at least about 15%, at least about 20%, at least about 25%, at least about 30%, at least about 35%, at least about 40%, at least about 45%, at least about 50%, at least about 75%, at least about 80%, at least about 85%, at least about 90%, or at least about 95% of the activity of the molecule in the absence of the inhibitory effect, e.g., in the absence of an inhibitor, such as a catecholic butane described herein. The term also refers to an observable or measurable reduction in activity. In treatment scenarios, preferably the inhibition is sufficient to produce a therapeutic and/or prophylactic benefit in the condition being treated. The phrase "does not inhibit" and its grammatical conjugations does not require a complete lack of effect on the activity. For example, it refers to situations where there is less than about 50%, less than about 40%, less than about 30%, less than about 20%, less than about 10%, or less than about 5% of reduction in EGFR and/or IGF-1R activity in the presence of an inhibitor such as a catecholic butane described herein.

Uses of Catecholic Butanes

Catecholic butanes can sensitize cancers or other proliferative diseases to conventional therapies as well as re-sensitize cancers or other proliferative diseases after they have acquired resistance to such conventional therapies. The embodiments described herein provide a method of inhibiting both EGFR and IGF-1R in a cell, comprising contacting a cell in which inhibition of both EGFR and IGF-1R is desired with a catecholic butane as described herein. Because compounds described herein are dual kinase inhibitors, they are useful research tools for in vitro study of the role of EGFR and IGF-1R in biological processes.

Assessment

Provided herein are methods of screening of subjects for levels of IGF-1R and EGFR tyrosine kinase activity, comprising: (i) analyzing a sample obtained from a subject comprising measuring levels of IGF-1R and EGFR; and (ii) comparing the levels of the IGF-1R and EGFR in the sample to the levels in a control.

Provided herein are methods for determining a disease treatment, comprising: (i) analyzing a sample obtained from a subject comprising measuring levels of IGF-1R and EGFR, and (ii) comparing the levels of the IGF-1R and EGFR in the sample to the levels in a control; wherein increased levels of IGF-1R , EGFR, or both as compared to the control indicate that the subject is to be treated with a dual tyrosine kinase inhibitor. In one embodiment, the dual tyrosine kinase inhibitor is a catecholic butane such as described herein.

In one embodiment, the level of EGFR expression is at baseline levels or greater than baseline levels and the level of IGF-1R expression is at baseline levels or greater than baseline levels. In another embodiment, the level of EGFR expression is at baseline levels and the level of IGF-1R expression is at 2× greater than baseline levels or more. In another embodiment, the level of IGF-1R expression is at baseline levels and the level of EGFR expression is at 2× greater than baseline levels or more. In yet another embodiment, the level of IGF-1R expression is at 2× greater than baseline levels or more and the level of EGFR expression is at 2× greater than baseline levels or more.

In one aspect, IGF-1R and EGFR may be analyzed by (a) introducing into a subject a labeled antibody directed against IGF-1R and labeled antibody directed against EGFR and (b) detecting said labeled antibodies by standard imaging techniques. An antibody can be labeled with a radioactive marker whose presence and location in a subject can be detected by standard imaging techniques. In one embodiment, the radioactive marker is different for said antibody directed against IGF-1R and said antibody directed against EGFR.

In one aspect, the method may further comprise administering to the subject a pharmaceutical compound capable of inhibiting the tyrosine kinase activity of IGF-1R and EGF-R, wherein said pharmaceutical compound is a catecholic butane that inhibits IGF-1R and EGFR.

For assessment of tumor cell biomarker expression, patient samples containing tumor cells, or proteins or nucleic acids produced by these tumor cells, can be used in methods described, for example, in U.S. Publication Number 20070065858, which is incorporated in its entirety by reference herein. Briefly, the level of expression of the biomarker can be assessed by assessing the amount (e.g., absolute amount or concentration) of the marker in a tumor cell sample, e.g., a tumor biopsy obtained from a patient, or other patient sample containing material derived from the tumor (e.g., blood, serum, urine, or other bodily fluids or excretions as described herein above). The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample. Likewise, tumor biopsies can also be subjected to post-collection preparative and storage techniques, e.g., fixation.

One can detect expression of biomarker proteins having at least one portion which is displayed on the surface of tumor cells which express it. One can determine whether a marker protein, or a portion thereof, is exposed on the cell surface. For example, immunological methods can be used to detect such proteins on whole cells, or well known computer-based sequence analysis methods can be used to predict the presence of at least one extracellular domain (i.e., including both secreted proteins and proteins having at least one cell-surface domain). Expression of a marker protein having at least one portion which is displayed on the surface of a cell which expresses it can be detected without necessarily lysing the tumor cell (e.g., using a labeled antibody which binds specifically with a cell-surface domain of the protein).

Expression of biomarkers can be assessed by any of a wide variety of well known methods for detecting expression of a transcribed nucleic acid or protein. Non-limiting examples of such methods include, for example, immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods or any other method known in the art.

Expression of a biomarker can be assessed using an antibody (e.g., a radio-labeled, chromophore-labeled, fluorophore-labeled, or enzyme-labeled antibody), an antibody derivative (e.g., an antibody conjugated with a substrate or with the protein or ligand of a protein-ligand pair (e.g., biotin-streptavidin), or an antibody fragment (e.g., a single-chain antibody, an isolated antibody hypervariable domain, etc.) which binds specifically to a biomarker protein or fragment thereof, including a biomarker protein which has undergone either all or a portion of post-translational modifications to which it is normally subjected in the tumor cell (e.g., glycosylation, phosphorylation, methylation, etc.).

Expression of a biomarker can also be assessed by preparing mRNA/cDNA (i.e., a transcribed polynucleotide) from cells in a patient sample, and by hybridizing the mRNA/cDNA with a reference polynucleotide which is a complement of a biomarker nucleic acid, or a fragment thereof cDNA can, optionally, be amplified using any of a variety of polymerase chain reaction methods prior to hybridization with the reference polynucleotide. Expression of one or more biomarkers can likewise be detected using quantitative PCR to assess the level of expression of one or more of the biomarkers. Alternatively, any of the many known methods of detecting mutations or variants (e.g., single nucleotide polymorphisms, deletions, etc.) of a biomarker can be used to detect occurrence of a biomarker in a patient.

A mixture of transcribed polynucleotides obtained from the sample can be contacted with a substrate having fixed thereto a polynucleotide complementary to or homologous with at least a portion (e.g., at least 7, 10, 15, 20, 25, 30, 40, 50, 100, 500, or more nucleotide residues) of a biomarker nucleic acid. If polynucleotides complementary to, or homologous with, are differentially detectable on the substrate (e.g., detectable using different chromophores or fluorophores, or fixed to different selected positions), then the levels of expression of a plurality of biomarkers can be assessed simultaneously using a single substrate (e.g., a "gene chip" microarray of polynucleotides fixed at selected positions). When a method of assessing biomarker expression is used which involves hybridization of one nucleic acid with another, hybridization can be performed under stringent hybridization conditions.

When a plurality of biomarkers are used in the methods described herein, the level of expression of each biomarker in a patient sample can be compared with the normal level of expression of each of the plurality of biomarkers in non-cancerous samples of the same type, either in a single reaction mixture (i.e., using reagents, such as different fluorescent probes, for each biomarker) or in individual reaction mixtures corresponding to one or more of the biomarkers.

The level of expression of a biomarker in normal (i.e., non-cancerous) human tissue can be assessed in a variety of ways. This normal level of expression can be assessed by assessing the level of expression of the biomarker in a portion of cells which appears to be non-cancerous, and then comparing the normal level of expression with the level of expression in a portion of the tumor cells. As further information becomes available as a result of routine performance of the methods described herein, population-average values for normal expression of the biomarkers can be used. Alternatively, the normal level of expression of a biomarker can be determined by assessing expression of the biomarker in a patient sample obtained from a non-cancer-afflicted patient, from a patient sample obtained from a patient before the suspected onset of cancer in the patient, from archived patient samples, and the like.

An exemplary method for detecting the presence or absence of a biomarker protein or nucleic acid in a biological sample involves obtaining a biological sample (e.g., a tumor-associated body fluid) from a test subject and contacting the biological sample with a compound or an agent capable of detecting the polypeptide or nucleic acid (e.g., mRNA, genomic DNA, or cDNA). The detection methods can, thus, be used to detect mRNA, protein, cDNA, or genomic DNA, for example, in a biological sample in vitro as well as in vivo. In vitro techniques for detection of mRNA include, for example, Northern hybridizations and in situ hybridizations. In vitro techniques for detection of a biomarker protein include, but are not limited to, enzyme linked immunosorbent assays (ELISAs), Western blots, immunohistochemistry, immunoprecipitation and immunofluorescence. In vitro techniques for detection of genomic DNA include, for example, Southern hybridizations. In vivo techniques for detection of mRNA include, for example, polymerase chain reaction (PCR), Northern hybridizations and in situ hybridizations. Furthermore, in vivo techniques for detection of a biomarker protein include introducing into a subject a labeled antibody directed against the protein or fragment thereof. For example, the antibody can be labeled with a radioactive marker whose presence and location in a subject can be detected by standard imaging techniques.

A general principle of such diagnostic and prognostic assays involves preparing a sample or reaction mixture that may contain a biomarker, and a probe, under appropriate conditions and for a time sufficient to allow the biomarker and probe to interact and bind, thus forming a complex that can be removed and/or detected in the reaction mixture. These assays can be conducted in a variety of ways.

For example, one method to conduct such an assay involves anchoring the biomarker or probe onto a solid phase support, also referred to as a substrate, and detecting target biomarker/probe complexes anchored on the solid phase at the end of the reaction. In one embodiment of such a method, a sample from a subject which is to be assayed for presence and/or concentration of biomarker can be anchored onto a carrier or solid phase support. In another embodiment, the reverse situation is possible, in which the probe can be anchored to a solid phase and a sample from a subject can be allowed to react as an unanchored component of the assay.

There are several established methods for anchoring assay components to a solid phase. These include, without limitation, biomarker or probe molecules which are immobilized through conjugation of biotin and streptavidin. Such biotinylated assay components can be prepared from biotin-NHS(N-hydroxy-succinimide) using techniques known in the art (e.g., biotinylation kit, Pierce Chemicals, Rockford, Ill.), and immobilized in the wells of streptavidin-coated 96-well plates (Pierce Chemical). In certain embodiments, the surfaces with immobilized assay components can be prepared in advance and stored. Other suitable carriers or solid phase supports for such assays include any material capable of binding the class of molecule to which the biomarker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite. In order to conduct assays with the above mentioned approaches, the non-immobilized component is added to the solid phase upon which the second component is anchored. After the reaction is complete, uncomplexed components can be removed (e.g., by washing) under conditions such that any complexes formed will remain immobilized upon the solid phase. The detection of biomarker/probe complexes anchored to the solid phase can be accomplished in a number of methods outlined herein. In one embodiment, the probe, when it is the unanchored assay component, can be labeled for the purpose of detection and readout of the assay, either directly or indirectly, with detectable labels discussed herein and which are well-known to one skilled in the art.

It is also possible to directly detect biomarker/probe complex formation without further manipulation or labeling of either component (biomarker or probe), for example by utilizing the technique of fluorescence energy transfer (i.e., FET, see for example, Lakowicz et al., U.S. Pat. No. 5,631,169; and Stavrianopoulos, et al., U.S. Pat. No. 4,868,103). A fluorophore label on a donor molecule is selected such that, upon excitation with incident light of appropriate wavelength, its emitted fluorescent energy will be absorbed by a fluorescent label on an acceptor molecule, which in turn is able to fluoresce due to the absorbed energy. Alternately, the donor protein molecule can simply utilize the natural fluorescent energy of tryptophan residues. Labels are chosen that emit different wavelengths of light, such that the acceptor molecule label can be differentiated from that of the donor. Since the efficiency of energy transfer between the labels is related to the distance separating the molecules, spatial relationships between the molecules can be assessed. In a situation in which binding occurs between the molecules, the fluorescent emission of the acceptor molecule label in the assay should be maximal. An FET binding event can be conveniently measured through standard fluorometric detection means well known in the art (e.g., using a fluorimeter).

In another embodiment, determination of the ability of a probe to recognize a biomarker can be accomplished without labeling either assay component (probe or biomarker) by utilizing a technology such as real-time Biomolecular Interaction Analysis (BIA; see, e.g., Sjolander, S, and Urbaniczky, C., 1991, Anal. Chem. 63:2338-2345 and Szabo et al., 1995, Curr. Opin. Struct. Biol. 5:699-705). As used herein, "BIA" or "surface plasmon resonance" refer to a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with biomarker and probe as solutes in a liquid phase. In such an assay, the complexed biomarker and probe are separated from uncomplexed components by any of a number of standard techniques, including but not limited to: differential centrifugation, chromatography, electrophoresis and immunoprecipitation. In differential centrifugation, biomarker/probe complexes can be separated from uncomplexed assay components through a series of centrifugal steps, due to the different sedimentation equilibria of complexes based on their different sizes and densities (see, for example, Rivas, G., and Minton, A. P., 1993, Trends Biochem Sci. 18(8): 284-7). Standard chromatographic techniques can also be utilized to separate complexed molecules from uncomplexed ones. For example, gel filtration chromatography separates molecules based on size, and through the utilization of an appropriate gel filtration resin in a column format, for example, the relatively larger complex can be separated from the relatively smaller uncomplexed components. Similarly, the relatively different charge properties of the biomarker/probe complex as compared to the uncomplexed components can be exploited to differentiate the complex from uncomplexed components, for example through the utilization of ion-exchange chromatography resins. Such resins and chromatographic techniques are well known to one skilled in the art (see, e.g., Heegaard, N.H., 1998, J. Mol. Recognit. Winter 11(1-6):141-8; Hage, D. S., and Tweed, S. A. J. Chromatogr B Biomed Sci Appl Oct. 10, 1997; 699(1-2):499-525). Gel electrophoresis can also be employed to separate complexed assay components from unbound components (see, e.g., Ausubel et al., ed., Current Protocols in Molecular Biology, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typically used. Appropriate conditions to the particular assay and components thereof will be well known to one skilled in the art.

In another embodiment, the level of biomarker mRNA can be determined both by in situ and by in vitro formats in a biological sample using methods known in the art. The term "biological sample" is intended to include tissues (including, but not limited to, tissue biopsies), cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from tumor cells (see, e.g., Ausubel et al., ed., Current Protocols in Molecular Biology, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or a genomic DNA encoding a biomarker described herein. Determination of appropriate stringency can be identified through routine testing according to conventional molecular techniques. Other suitable probes for use in the diagnostic assays described herein. Hybridization of an mRNA with the probe indicates that a biomarker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array according to manufacturer's instructions. A skilled artisan can readily adapt known mRNA detection methods for use in detecting the level of mRNA encoded by the biomarkers described herein.

An alternative method for determining the level of mRNA biomarker in a sample involves the process of nucleic acid amplification, e.g., by reverse transcriptase—polymerase chain reaction (RT-PCR; e.g., the experimental embodiment set forth in Mullis, 1987, U.S. Pat. No. 4,683,202), ligase chain reaction (e.g., Barany, 1991, Proc. Natl. Acad. Sci. USA, 88:189-193), self sustained sequence replication (e.g., Guatelli et al., 1990, Proc. Natl. Acad. Sci. USA 87:1874-1878), transcriptional amplification system (e.g., Kwoh et al., 1989, Proc. Natl. Acad. Sci. USA 86:1173-1177), Q-Beta Replicase (Lizardi et al., 1988, Bio/Technology 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the tumor cells prior to detection. In such methods, a cell or tissue sample is prepared/processed using known histological methods. The sample is then immobilized on a support, typically a glass slide, and then contacted with a probe that can hybridize to mRNA that encodes the biomarker.

As an alternative to making determinations based on the absolute expression level of the biomarker, determinations can be based on the normalized expression level of the biomarker. Expression levels are normalized by correcting the absolute expression level of a biomarker by comparing its expression to the expression of a gene that is not a biomarker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-tumor sample, or between samples from different sources.

Alternatively, the expression level can be provided as a relative expression level. To determine a relative expression level of a biomarker (e.g., a mesenchymal biomarker), the level of expression of the biomarker is determined for 10 or more, 20 or more, 30 or more, 40 or more, or 50 or more samples of normal versus cancer cell isolates prior to the determination of the expression level for the sample in question. The mean expression level of each of the genes assayed in the larger number of samples is determined and this is used as a baseline expression level for the biomarker. The expression level of the biomarker determined for the test sample (absolute level of expression) is then divided by the mean expression value obtained for that biomarker. This provides a relative expression level.

In another embodiment, a biomarker protein is detected. One type of agent for detecting biomarker protein is an antibody capable of binding to such a protein or a fragment thereof such as, for example, a detectably labeled antibody. Antibodies can be polyclonal or monoclonal. An intact antibody, or an antigen binding fragment thereof (e.g., Fab, $F(ab')_2$, Fv, scFv, single binding chain polypeptide) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Proteins from tumor cells can be isolated using techniques that are well known to those of skill in the art. The protein isolation methods employed can, for example, be such as those described in Harlow and Lane (Harlow and Lane, 1988, Antibodies: A Laboratory Manual, Cold Spring Harbor Laboratory Press, Cold Spring Harbor, N.Y.).

A variety of formats can be employed to determine whether a sample contains a protein that binds to a given antibody. Examples of such formats include, but are not limited to, enzyme immunoassay (EIA), radioimmunoassay (RIA), Western blot analysis, immunohistochemistry and enzyme linked immunoabsorbant assay (ELISA). A skilled artisan can readily adapt known protein/antibody detection methods for use in determining whether tumor cells express a biomarker.

In one format, antibodies, or antibody fragments or derivatives, can be used in methods such as Western blots or immunofluorescence techniques to detect the expressed proteins. In such uses, either the antibody or proteins can be immobilized on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. One will know, or can determine, other suitable carriers for binding antibody or antigen, and will be able to adapt such support for use in the present methods. For example, proteins isolated from tumor cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

For ELISA assays, specific binding pairs can be of the immune or non-immune type. Immune specific binding pairs are exemplified by antigen-antibody systems or hapten/anti-hapten systems. There can be mentioned fluorescein/anti-fluorescein, dinitrophenyl/anti-dinitrophenyl, biotin/anti-biotin, peptide/anti-peptide and the like. The antibody member of the specific binding pair can be produced by customary methods familiar to those skilled in the art. Such methods involve immunizing an animal with the antigen member of the specific binding pair. If the antigen member of the specific binding pair is not immunogenic, e.g., a hapten, it can be covalently coupled to a carrier protein to render it immunogenic. Non-immune binding pairs include systems wherein the two components share a natural affinity for each other but are not antibodies. Exemplary non-immune pairs are biotin-streptavidin, intrinsic factor-vitamin B12, folic acid-folate binding protein and the like.

A variety of methods are available to covalently label antibodies with members of specific binding pairs. Methods are selected based upon the nature of the member of the specific binding pair, the type of linkage desired, and the tolerance of the antibody to various conjugation chemistries. Biotin can be covalently coupled to antibodies by utilizing commercially available active derivatives. Some of these are biotin-N-hydroxy-succinimide which binds to amine groups on proteins; biotin hydrazide which binds to carbohydrate moieties, aldehydes and carboxyl groups via a carbodiimide coupling; and biotin maleimide and iodoacetyl biotin which bind to sulfhydryl groups. Fluorescein can be coupled to protein amine groups using fluorescein isothiocyanate. Dinitrophenyl groups can be coupled to protein amine groups using 2,4-dinitrobenzene sulfate or 2,4-dinitrofluorobenzene. Other standard methods of conjugation can be employed to couple monoclonal antibodies to a member of a specific binding pair including dialdehyde, carbodiimide coupling, homofunctional cross-linking, and heterobifunctional cross-linking Carbodiimide coupling is an effective method of coupling carboxyl groups on one substance to amine groups on another. Carbodiimide coupling is facilitated by using the commercially available reagent 1-ethyl-3-(dimethyl-amino-propyl)-carbodiimide (EDAC).

Homobifunctional cross-linkers, including the bifunctional imidoesters and bifunctional N-hydroxysuccinimide esters, are commercially available and are employed for coupling amine groups on one substance to amine groups on another. Heterobifunctional cross-linkers are reagents which possess different functional groups. The most common commercially available heterobifunctional cross-linkers have an amine reactive N-hydroxysuccinimide ester as one functional group, and a sulfhydryl reactive group as the second functional group. The most common sulfhydryl reactive groups are maleimides, pyridyl disulfides and active halogens. One of the functional groups can be a photoactive aryl nitrene, which upon irradiation reacts with a variety of groups.

A detectably-labeled antibody or detectably-labeled member of the specific binding pair can be prepared via coupling to a reporter, which can be a radioactive isotope, enzyme, fluorogenic, chemiluminescent or electrochemical materials. Two commonly used radioactive isotopes are $^{125}$I and $^{3}$H. Standard radioactive isotopic labeling procedures include the chloramine T, lactoperoxidase and Bolton-Hunter methods for $^{125}$I and reductive methylation for $^{3}$H. The term "detectably-labeled" refers to a molecule labeled in such a way that it can be readily detected by the intrinsic enzymatic activity of the label or by the binding to the label of another component, which can itself be readily detected.

Enzymes suitable for use in this method include, but are not limited to, horseradish peroxidase, alkaline phosphatase, β-galactosidase, glucose oxidase, luciferases, including firefly and renilla, β-lactamase, urease, green fluorescent protein (GFP) and lysozyme. Enzyme labeling is facilitated by using dialdehyde, carbodiimide coupling, homobifunctional crosslinkers and heterobifunctional crosslinkers as described above for coupling an antibody with a member of a specific binding pair.

The labeling method chosen depends on the functional groups available on the enzyme and the material to be labeled, and the tolerance of both to the conjugation conditions. The labeling method used may be one of, but not limited to, any conventional methods currently employed including those described by Engvall and Pearlmann, Immunochemistry 8, 871 (1971), Avrameas and Temynck, Immunochemistry 8, 1175 (1975), Ishikawa et al., J. Immunoassay 4(3):209-327 (1983) and Jablonski, Anal. Biochem. 148:199 (1985).

Labeling can be accomplished by indirect methods such as using spacers or other members of specific binding pairs. An example of this is the detection of a biotinylated antibody with unlabeled streptavidin and biotinylated enzyme, with streptavidin and biotinylated enzyme being added either sequentially or simultaneously. Thus, an antibody used to detect may be detectably-labeled directly with a reporter or indirectly with a first member of a specific binding pair. When the antibody is coupled to a first member of a specific binding pair, then detection is effected by reacting the antibody-first member of a specific binding complex with the second member of the binding pair that is labeled or unlabeled as mentioned above.

Moreover, the unlabeled detector antibody can be detected by reacting the unlabeled antibody with a labeled antibody specific for the unlabeled antibody. In this instance "detectably-labeled" as used above is taken to mean containing an epitope by which an antibody specific for the unlabeled antibody can bind. Such an anti-antibody can be labeled directly or indirectly using any of the approaches discussed above. For example, the anti-antibody can be coupled to biotin which is detected by reacting with the streptavidin-horseradish peroxidase system discussed above. Thus, in one embodiment, biotin is utilized. The biotinylated antibody is in turn reacted with streptavidin-horseradish peroxidase complex. Orthophenylenediamine, 4-chloro-naphthol, tetramethylbenzidine (TMB), ABTS, BTS or ASA can be used for chromogenic detection.

In one immunoassay format, a forward sandwich assay is used in which the capture reagent has been immobilized, using conventional techniques, on the surface of a support. Suitable supports used in assays include synthetic polymer supports, such as polypropylene, polystyrene, substituted polystyrene, e.g., aminated or carboxylated polystyrene, polyacrylamides, polyamides, polyvinylchloride, glass beads, agarose, or nitrocellulose.

A combination of two or more of the assays described above can also be used to assess one or more biomarkers.

The values obtained from the test and/or control samples are statistically processed using any suitable method of statistical analysis to establish a suitable baseline level using methods standard in the art for establishing such values. Statistical significance can be readily determined as further described, for example, in U.S. patent application Ser. No. 11/781,946. By way of example only, in one embodiment, statistical significance is at least $p<0.05$.

Treatment of Proliferative Diseases

Described herein are compounds, pharmaceutical compositions and methods for treating a patient suffering from a proliferative disease by administering an effective amount of a catecholic butane (i.e., a single compound that is a dual kinase inhibitor) as described herein, alone or in combination with one or more additional active ingredients (e.g., anticancer agents) and/or treatment regimens (e.g., surgery).

The present application relates generally to methods of treatment of diseases using a catecholic butane (or a derivative thereof) described herein. By way of example, it relates to the use of the catecholic butane NDGA or a salt, solvate, isomer, tautomer, metabolite, analog, or prodrug thereof in treating a proliferative disease by inhibiting IGF-1R and EGFR.

Provided herein are methods for treating a disease comprising administering an effective amount of a pharmaceutical compound capable of inhibiting the tyrosine kinase activity of both IGF-1R and EGFR, wherein the pharmaceutical compound is a catecholic butane described herein (i.e., one compound that is a dual kinase inhibitor).

Also provided herein are methods for treating a disease in a subject that has developed resistance to one or more EGF-R inhibitors or IGF-1R inhibitors comprising administering an effective amount of a pharmaceutical compound capable of inhibiting the tyrosine kinase activity of both of IGF-1R and EGFR, wherein the pharmaceutical compound is a catecholic butane (i.e., a dual kinase inhibitor).

In one embodiment, the disease is a proliferative disease.

A proliferative disease includes, but is not limited to, a malignant, pre-malignant or benign cancer. Cancers to be treated using the disclosed methods include, for example, a solid tumor, a lymphoma or a leukemia. In one embodiment, a cancer can be, for example, a brain tumor (e.g., a malignant, pre-malignant or benign brain tumor such as, for example, a glioblastoma, an astrocytoma, a meningioma, a medulloblastoma or a peripheral neuroectodermal tumor), a carcinoma (e.g., gall bladder carcinoma, bronchial carcinoma, basal cell carcinoma, adenocarcinoma, squamous cell carcinoma, small cell carcinoma, large cell undifferentiated carcinoma, adenomas, cystadenoma, etc.), a basalioma, a teratoma, a retinoblastoma, a choroidea melanoma, a seminoma, a sarcoma (e.g., Ewing sarcoma, rhabdomyosarcoma, craniopharyngeoma, osteosarcoma, chondrosarcoma, myosarcoma, liposarcoma, fibrosarcoma, leimyosarcoma, Askin's tumor, lymphosarcoma, neurosarcoma, Kaposi's sarcoma, dermatofibrosarcoma, angiosarcoma, etc.), a plasmocytoma, a head and neck tumor (e.g., oral, laryngeal, nasopharyngeal, esophageal, etc.), a liver tumor, a kidney tumor, a renal cell tumor, a squamous cell carcinoma, a uterine tumor, a bone tumor, a prostate tumor, a breast tumor including, but not limited to a breast tumor that is Her2- and/or ER- and/or PR-, a bladder tumor, a pancreatic tumor, an endometrium tumor, a squamous cell carcinoma, a stomach tumor, gliomas, a colorectal tumor, a testicular tumor, a colon tumor, a rectal tumor, an ovarian tumor, a cervical tumor, an eye tumor, a central nervous system tumor (e.g., primary CNS lymphomas, spinal axis tumors, brain stem gliomas, pituitary adenomas, etc.), a thyroid tumor, a lung tumor (e.g., non-small cell lung cancer (NSCLC) or small cell lung cancer), a leukemia or a lymphoma (e.g., cutaneous T-cell lymphomas (CTCL), non-cutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma, etc.), a multiple myeloma, a skin tumor (e.g., basal cell carcinomas, squamous cell carcinomas, melanomas such as malignant melanomas, cutaneous melanomas or intraocular melanomas, Dermatofibrosarcoma protuberans, Merkel cell carcinoma or Kaposi's sarcoma), a gynecologic tumor (e.g., uterine sarcomas, carcinoma of the fallopian tubes, carcinoma of the endometrium, carcinoma of the cervix, carcinoma of the vagina, carcinoma of the vulva, etc.), Hodgkin's disease, a cancer of the small intestine, a cancer of the endocrine system (e.g., a cancer of the thyroid, parathyroid or adrenal glands, etc.), a mesothelioma, a cancer of the urethra, a cancer of the penis, tumors related to Gorlin's syndrome (e.g., medulloblastomas, meningioma, etc.), a tumor of unknown origin; or metastases of any thereto.

In another embodiment, the cancer is a lung tumor, a breast tumor, a colon tumor, a colorectal tumor, a head and neck tumor, a liver tumor, a prostate tumor, a glioma, glioblastoma multiforme, a ovarian tumor or a thyroid tumor; or metastases of any thereto.

In yet another embodiment, the cancer is an endometrial tumor, bladder tumor, multiple myeloma, melanoma, renal tumor, sarcoma, cervical tumor, leukemia, and neuroblastoma.

Tumors as provided herein may be primary tumors or metastases. Cancers may also be epithelial based cancers. In one embodiment, cells of tumors may express EGFR. In another embodiment, cells of tumors may express IGF-1R. In yet another embodiment, cells of tumors may express EGFR and IGF-1R.

Provided herein are methods for treating a malignant, pre-malignant or benign cancer, comprising administering an effective amount of a pharmaceutical compound capable of inhibiting the tyrosine kinase activity of IGF-1R and EGFR, wherein the pharmaceutical compound is a catecholic butane (i.e., a single compound that is a dual kinase inhibitor).

Provided herein are methods of selecting a subject for treatment with a catecholic butane capable of inhibiting the tyrosine kinase activity of both IGF-1R and EGF-R, wherein said subject is identified as having levels of IGF-1R, EGFR, or both at baseline levels or at 2× greater than baseline levels as compared to control levels.

In one aspect, a subject has been previously treated with an EGFR inhibitor or an IGF-1R inhibitor.

In another aspect, the subject may be resistant to treatment with at least one tyrosine kinase inhibitor, for example, an EGFR inhibitor alone or an IGF-1R inhibitor alone or an IGF-1R and EGFR inhibitor.

Provided herein are methods for degrading, inhibiting the growth of or killing cancer cells of epithelial origin comprising contacting the cells with an amount of a catecholic butane effective to degrade, inhibit the growth of or kill cancer cells.

Provided herein are methods of inhibiting tumor size increase, reducing the size of a tumor, reducing tumor proliferation or preventing tumor proliferation in an individual comprising administering to said individual an effective amount of a catecholic butane described herein to inhibit tumor size increase, reduce the size of a tumor, reduce tumor proliferation or prevent tumor proliferation. Treatment of tumors in some cases includes stasis of symptoms, that is, by treating the patient, the cancer does not worsen and survival of the patient is prolonged.

Patients may be assessed with respect to symptoms at one or more multiple time points including prior to, during, and after treatment regimens. Treatment can result in improving the subject's condition and can be assessed by determining if one or more of the following events has occurred: decreased tumor size, decreased tumor cell proliferation, decreased numbers of cells, decreased neovascularization and/or increased apoptosis. One or more of these occurrences may, in some cases, result in partial or total elimination of the cancer and prolongation of survival of the patient. Alternatively, for terminal stage cancers, treatment may result in stasis of disease, better quality of life and/or prolongation of survival. Other methods of assessing treatment are known in the art and contemplated herein.

One would understand that classification and staging systems described herein may be used to assess treatment of cancers described herein; additionally, other staging schemes are known in the art and may be used in connection with the methods described herein. By way of example only, the TNM classification of malignant tumors may be used as a cancer staging system to describe the extent of cancer in a patient's body. T describes the size of the tumor and whether it has invaded nearby tissue, N describes regional lymph nodes that are involved, and M describes distant metastasis. TNM is maintained by the International Union Against Cancer (UICC) and is used by the American Joint Committee on Cancer (AJCC) and the International Federation of Gynecology and Obstetrics (FIGO). One would understand that not all tumors have TNM classifications such as, for example, brain tumors. Generally, T (a,is,(0), 1-4) is measured as the size or direct extent of the primary tumor. N (0-3) refers to the degree of spread to regional lymph nodes: N0 means that tumor cells are absent from regional lymph nodes, N1 means that tumor cells spread to the closest or small numbers of regional lymph nodes, N2 means that tumor cells spread to an extent between N1 and N3; N3 means that tumor cells spread to most distant or numerous regional lymph nodes. M (0/1) refers to the presence of metastasis: M0 means that no distant metastasis are present; M1 means that metastasis has occurred to distant organs (beyond regional lymph nodes). Other parameters may also be assessed. G (1-4) refers to the grade of cancer cells (i.e., they are low grade if they appear similar to normal cells, and high grade if they appear poorly differentiated). R (0/1/2) refers to the completeness of an operation (i.e., resection-boundaries free of cancer cells or not). L (0/1) refers to invasion into lymphatic vessels. V (0/1) refers to invasion into vein. C (1-4) refers to a modifier of the certainty (quality) of V.

Breast Cancer

In one aspect, provided herein is a method of treating breast cancer, such as a ductal carcinoma in duct tissue in a mammary gland, a breast cancer that is Her2- and/or ER- and/or PR-.

Several types of breast cancer exist that may be treated by the methods described herein. A lobular carcinoma in situ and a ductal carcinoma in situ are breast cancers that have developed in the lobules and ducts, respectively, but have not spread to the fatty tissue surrounding the breast or to other areas of the body. Infiltrating (or invasive) lobular and ductal carcinoma are cancers that have developed in the lobules and ducts, respectively, and have spread to either the breast's fatty tissue and/or other parts of the body. Other cancers of the breast that would benefit from treatment by the methods are medullary carcinomas, colloid carcinomas, tubular carcinomas, and inflammatory breast cancer.

In one embodiment, breast cancer is staged according to the TNM system. Prognosis is closely linked to results of staging, and staging is also used to allocate patients to treatments both in clinical trials and clinical practice.

Briefly, the information for staging is as follows:

TX: Primary tumor cannot be assessed. T0: No evidence of tumor. T is: Carcinoma in situ, no invasion; T1: Tumor is 2 cm or less; T2: Tumor is more than 2 cm but not more than 5 cm; T3: Tumor is more than 5 cm; T4: Tumor of any size growing into the chest wall or skin, or inflammatory breast cancer NX: Nearby lymph nodes cannot be assessed NO: cancer has not spread to regional lymph nodes. N1: cancer has spread to 1 to 3 axillary or one internal mammary lymph node N2: cancer has spread to 4 to 9 axillary lymph nodes or multiple internal mammary lymph nodes N3: One of the following applies: cancer has spread to 10 or more axillary lymph nodes, or cancer has spread to the lymph nodes under the clavicle (collar bone), or cancer has spread to the lymph nodes above the clavicle, or cancer involves axillary lymph nodes and has enlarged the internal mammary lymph nodes, or cancer involves 4 or more axillary lymph nodes, and tiny amounts of cancer are found in internal mammary lymph nodes on sentinel lymph node biopsy.

MX: presence of distant spread (metastasis) cannot be assessed. M0: no distant spread. M1: spread to distant organs (not including the supraclavicular lymph node) has occurred.

The methods provided herein may provide a beneficial effect for breast cancer patients, by administration of a catecholic butane or a combination of administration of a catecholic butane and one or more anticancer treatments.

Ovarian Cancer

In another aspect, provided herein is a method of treating ovarian cancer, including epithelial ovarian tumors. Preferably, the method treats an ovarian cancer selected from the following: an adenocarcinoma in the ovary and an adenocarcinoma that has migrated from the ovary into the abdominal cavity.

The methods provided herein may provide a beneficial effect for ovarian cancer patients, by administration of a catecholic butane or a combination of administration of a catecholic butane and one or more anticancer treatments.

Cervical Cancer

In another aspect, the method treats cervical cancer, preferably an adenocarcinoma in the cervix epithelial. Two main types of this cancer exist: squamous cell carcinoma and adenocarcinomas. The former constitutes about 80-90% of all cervical cancers and develops where the ectocervix (portion closest to the vagina) and the endocervix (portion closest to the uterus) join. The latter develop in the mucous-producing gland cells of the endocervix. Some cervical cancers have characteristics of both of these and are called adenosquamous carcinomas or mixed carcinomas.

The methods provided herein may provide a beneficial effect for cervical cancer patients, by administration of a catecholic butane or a combination of administration of a catecholic butane and one or more anticancer treatments.

Prostate Cancer

In one other aspect, provided herein is a method to treat prostate cancer, preferably a prostate cancer selected from the following: an adenocarcinoma or an adenocarinoma that has migrated to the bone. Prostate cancer develops in the prostate organ in men, which surrounds the first part of the urethra. The prostate has several cell types but 99% of tumors are adenocarcinomas that develop in the glandular cells responsible for generating seminal fluid.

There are two schemes commonly used to stage prostate cancer. The most common is the TNM system, which evaluates the size of the tumor, the extent of involved lymph nodes, and any metastasis (distant spread). As with many other cancers, these are often grouped into four stages (I-IV). Another scheme, used less commonly, is the Whitmore-Jewett stage.

Briefly, Stage I disease is cancer that is found incidentally in a small part of the sample when prostate tissue was removed for other reasons, such as benign prostatic hypertrophy, and the cells closely resemble normal cells and the gland feels normal to the examining finger. In Stage II more of the prostate is involved and a lump can be felt within the gland. In Stage III, the tumor has spread through the prostatic capsule and the lump can be felt on the surface of the gland. In Stage IV disease, the tumor has invaded nearby structures, or has spread to lymph nodes or other organs. Grading is based on cellular content and tissue architecture from biopsies (Gleason) which provides an estimate of the destructive potential and ultimate prognosis of the disease.

The methods provided herein may provide a beneficial effect for prostate cancer patients, by administration of a catecholic butane or a combination of administration of a catecholic butane and one or more anticancer treatments.

Pancreatic Cancer

In another aspect, provided herein is a method of treating pancreatic cancer, preferably a pancreatic cancer selected from the following: an epitheliod carcinoma in the pancreatic duct tissue and an adenocarcinoma in a pancreatic duct. The most common type of pancreatic cancer is an adenocarcinoma, which occurs in the lining of the pancreatic duct.

The methods provided herein may provide a beneficial effect for pancreatic cancer patients, by administration of a catecholic butane or a combination of administration of a catecholic butane and one or more anticancer treatments.

Bladder Cancer

In another aspect, provided herein is a method of treating bladder cancer, preferably a transitional cell carcinoma in urinary bladder. Bladder cancers are urothelial carcinomas (transitional cell carcinomas) or tumors in the urothelial cells that line the bladder. The remaining cases of bladder cancer are squamous cell carcinomas, adenocarcinomas, and small cell cancers. Several subtypes of urothelial carcinomas exist depending on whether they are noninvasive or invasive and whether they are papillary, or flat. Noninvasive tumors are in the urothelium, the innermost layer of the bladder, while invasive tumors have spread from the urothelium to deeper layers of the bladder's main muscle wall. Invasive papillary urothelial carcinomas are slender finger-like projections that branch into the hollow center of the bladder and also grow outward into the bladder wall. Non-invasive papillary urothelial tumors grow towards the center of the bladder. While a non-invasive, flat urothelial tumor (also called a flat carcinoma in situ) is confined to the layer of cells closest to the inside hollow part of the bladder, an invasive flat urothelial carcinoma invades the deeper layer of the bladder, particularly the muscle layer.

The methods provided herein may provide a beneficial effect for bladder cancer patients, by administration of a catecholic butane or a combination of administration of a catecholic butane and one or more anticancer treatments.

Acute Myeloid Leukemia

In another aspect, provided herein is a method of treating acute myeloid leukemia (AML), preferably acute promyelocytic leukemia in peripheral blood. AML begins in the bone marrow but can spread to other parts of the body including the lymph nodes, liver, spleen, central nervous system, and testes. It is acute meaning it develops quickly and may be fatal if not treated within a few months. AML is characterized by immature bone marrow cells usually granulocytes or monocytes, which continue to reproduce and accumulate.

There are other types of leukemia's that can also be treated by the methods provided herein including but not limited to, Acute Lymphocytic Leukemia, Acute Myeloid Leukemia, Chronic Lymphocytic Leukemia, Chronic Myeloid Leukemia, Hairy Cell Leukemia, Myelodysplasia, and Myeloproliferative Disorders.

The methods provided herein may provide a beneficial effect for leukemia patients, by administration of a catecholic butane or a combination of administration of a catecholic butane and one or more anticancer treatments.

Lung Cancer

In another aspect, provided herein is a method to treat lung cancer. The most common type of lung cancer is non-small cell lung cancer (NSCLC), which accounts for approximately 80-85% of lung cancers and is divided into squamous cell carcinomas, adenocarcinomas, and large cell undifferentiated carcinomas. Small cell lung cancer accounts for 15-20% of lung cancers.

Lung cancer staging is an assessment of the degree of spread of the cancer from its original source. It is an important factor affecting the prognosis and potential treatment of lung cancer. Non-small cell lung carcinoma is staged from IA ("one A"; best prognosis) to IV ("four"; worst prognosis). Small cell lung carcinoma is classified as limited stage if it is confined to one half of the chest and within the scope of a single radiotherapy field; otherwise, it is extensive stage.

Lung cancer may be staged using EUS (endoscopic ultrasound) or TNM. Staging a part of the assessment of patients with non-small cell lung carcinoma. These patients undergo staging as part of the process of considering prognosis and treatment. The AJCC recommends TNM staging followed by further grouping.

Primary Tumor (T):

TX: The primary tumor cannot be assessed, or there are malignant cells in the sputum or bronchoalveolar lavage but not seen on imaging or bronchoscopy;

T is: Carcinoma in situ.

T0: No evidence of primary tumor.

T1: Tumor less than 3 cm in its greatest dimension, surrounded by lung or visceral pleura and without bronchoscopic invasion into the main bronchus.

T2: A tumor with any of: more than 3 cm in greatest dimension; extending into the main bronchus (but more than 2 cm distal to the carina), and obstructive pneumonitis (but not involving the entire lung).

T3: A tumor with any of: invasion of the chest wall, diaphragm, mediastinal pleura, or parietal pericardium; extending into the main bronchus, within 2 cm of the carina, but not involving the carina; and obstructive pneumonitis of the entire lung.

T4: A tumor with any of: invasion of the mediastinum, heart, great vessels, trachea, esophagus, vertebra, or carina; separate tumor nodules in the same lobe; and malignant pleural effusion.

Lymph nodes (N): NX: Lymph nodes cannot be assessed; N0: No lymph nodes involved; N1: Metastasis to ipsilateral peribronchial or ipsilateral hilar lymph nodes; N2: Metastasis to ipsilateral mediastinal or subcarinal lymph nodes; and N3: Metastasis to any of: ipsilateral supraclavicular lymph nodes; ipsilateral scalene lymph nodes; and contralateral lymph nodes.

Distant metastasis (M): MX: Distant metastasis cannot be assessed; M0: No distant metastasis; and M1: Distant metastasis is present.

The methods provided herein may provide a beneficial effect for lung cancer patients, by administration of a catecholic butane or a combination of administration of a catecholic butane and one or more anticancer treatments.

Skin Cancer

In another aspect, provided herein is a method to treat skin cancer. There are several types of cancer that start in the skin. The most common types are basal cell carcinoma and squamous cell carcinoma, which are non-melanoma skin cancers. Actinic keratosis is a skin condition that sometimes develops into squamous cell carcinoma. Non-melanoma skin cancers rarely spread to other parts of the body. Melanoma, the rarest form of skin cancer, is more likely to invade nearby tissues and spread to other parts of the body.

The methods provided herein may provide a beneficial effect for skin cancer patients, by administration of a catecholic butane or a combination of administration of a catecholic butane and one or more anticancer treatments.

Eye Cancer, Retinoblastoma

In another aspect, provided herein is a method to treat eye retinoblastoma. Retinoblastoma is a malignant tumor of the retina. Although retinoblastoma may occur at any age, it most often occurs in younger children, usually before the age of 5 years. The tumor may be in one eye only or in both eyes. Retinoblastoma is usually confined to the eye and does not spread to nearby tissue or other parts of the body.

The methods provided herein may provide a beneficial effect for eye retinoblastoma patients, by administration of a catecholic butane or a combination of administration of a catecholic butane and one or more anticancer treatments.

Eye Cancer, Intraocular Melanoma

In another aspect, provided herein is a method to treat intraocular (eye) melanoma. Intraocular melanoma, a rare cancer, is a disease in which cancer cells are found in the part of the eye called the uvea. The uvea includes the iris, the ciliary body, and the choroid. Intraocular melanoma occurs most often in people who are middle aged.

The methods provided herein may provide a beneficial effect for intraocular melanoma patients, by administration of a catecholic butane or a combination of administration of a catecholic butane and one or more anticancer treatments.

Endometrium Cancer

In another aspect, provided herein is a method to treat endometrium cancer. Endometrial cancer is a cancer that starts in the endometrium, the inner lining of the uterus. Some of the examples of the cancer of uterus and endometrium include, but are not limited to, adenocarcinomas, adenoacanthomas, adenosquamous carcinomas, papillary serous adenocarcinomas, clear cell adenocarcinomas, uterine sarcomas, stromal sarcomas, malignant mixed mesodermal tumors, and leiomyosarcomas.

The methods provided herein may provide a beneficial effect for endometrium cancer patients, by administration of a catecholic butane or a combination of administration of a catecholic butane and one or more anticancer treatments.

Liver Cancer

In another aspect, provided herein is a method to treat primary liver cancer (cancer that begins in the liver). Primary liver cancer can occur in both adults and children.

The methods provided herein may provide a beneficial effect for liver cancer patients, by administration of a catecholic butane or a combination of administration of a catecholic butane and one or more anticancer treatments.

Kidney Cancer

In another aspect, provided herein is a method to treat kidney cancer. Kidney cancer (also called renal cell cancer or renal adenocarcinoma) is a disease in which malignant cells are found in the lining of tubules in the kidney.

The methods provided herein may provide a beneficial effect for kidney cancer patients, by administration of a catecholic butane or a combination of administration of a catecholic butane and one or more anticancer treatments.

Thyroid Cancer

In another aspect, provided herein is a method to treat thyroid cancer. Thyroid cancer is a disease in which cancer (malignant) cells are found in the tissues of the thyroid gland. The four main types of thyroid cancer are papillary, follicular, medullary and anaplastic.

The methods provided herein may provide a beneficial effect for thyroid cancer patients, by administration of a catecholic butane or a combination of administration of a catecholic butane and one or more anticancer treatments.

AIDS Related Cancers

Provided herein are methods to treat AIDS-related cancers including, but not limited to AIDS-related lymphoma and Kaposi's Sarcoma. The methods provided herein may provide a beneficial effect for AIDS-related cancers, by administration of a catecholic butane or a combination of administration of a catecholic butane or a combination of administration of a catecholic butane and one or more anticancer treatments.

AIDS-Related Lymphoma

In another aspect, provided herein is a method to treat AIDS-related lymphoma. AIDS-related lymphoma is a disease in which malignant cells form in the lymph system of patients who have acquired immunodeficiency syndrome (AIDS). AIDS is caused by the human immunodeficiency virus (HIV), which attacks and weakens the body's immune system. The immune system is then unable to fight infection and diseases that invade the body. People with HIV disease have an increased risk of developing infections, lymphoma, and other types of cancer. Lymphomas are cancers that affect the white blood cells of the lymph system. Lymphomas are divided into two general types: Hodgkin's lymphoma and non-Hodgkin's lymphoma. Both Hodgkin's lymphoma and non-Hodgkin's lymphoma may occur in AIDS patients, but non-Hodgkin's lymphoma is more common. When a person with AIDS has non-Hodgkin's lymphoma, it is called an AIDS-related lymphoma. Non-Hodgkin's lymphomas may be indolent (slow-growing) or aggressive (fast-growing). AIDS-related lymphoma is usually aggressive. The three main types of AIDS-related lymphoma are diffuse large B-cell lymphoma, B-cell immunoblastic lymphoma and small non-cleaved cell lymphoma.

Treatment of AIDS-related lymphoma combines treatment of the lymphoma with treatment for AIDS. Patients with AIDS have weakened immune systems and treatment can cause further damage. For this reason, patients who have AIDS-related lymphoma are usually treated with lower doses of drugs than lymphoma patients who do not have AIDS. Highly-active antiretroviral therapy (HAART) is used to slow progression of HIV. Medicine to prevent and treat infections, which can be serious, is also used.

Kaposi's Sarcoma

In another aspect, provided herein is a method to treat Kaposi's sarcoma. Kaposi's sarcoma is a disease in which cancer cells are found in the tissues under the skin or mucous membranes that line the mouth, nose, and anus. Classic Kaposi's sarcoma usually occurs in older men of Jewish, Italian, or Mediterranean heritage. This type of Kaposi's sarcoma progresses slowly, sometimes over 10 to 15 years. Kaposi's sarcoma may occur in people who are taking immunosuppressants. Kaposi's sarcoma in patients who have Acquired Immunodeficiency Syndrome (AIDS) is called epidemic Kaposi's sarcoma. Kaposi's sarcoma in people with AIDS usually spreads more quickly than other kinds of Kaposi's sarcoma and often is found in many parts of the body.

The methods provided herein may provide a beneficial effect for Kaposi's sarcoma, by administration of a catecholic butane or a combination of administration of a catecholic butane and one or more anticancer treatments.

Viral-Induced Cancers

In another aspect, provided herein is a method to treat viral-induced cancers. Several common viruses are clearly or probable causal factors in the etiology of specific malignancies. These viruses either normally establish latency or few can become persistent infections. Oncogenesis is probably linked to an enhanced level of viral activation in the infected host, reflecting heavy viral dose or compromised immune control. The major virus-malignancy systems include hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer. In general, these malignancies occur relatively early in life, typically peaking in middle-age or earlier.

Virus-Induced Hepatocellular Carcinoma

The causal relationship between both HBV and HCV and hepatocellular carcinoma or liver cancer is established through substantial epidemiologic evidence. Both appear to act via chronic replication in the liver by causing cell death and subsequent regeneration.

Viral-Induced Adult T cell leukemia/lymphoma

The association between HTLV-1 and Adult T cell leukemia (ATL) is firmly established. Unlike the other oncogenic viruses found throughout the world, HTLV-1 is highly geographically restricted, being found primarily in southern Japan, the Caribbean, west and central Africa, and the South Pacific islands. Evidence for causality includes the monoclonal integration of viral genome in almost all cases of ATL in carriers. The risk factors for HTLV-1-associated malignancy appear to be perinatal infection, high viral load, and being male sex. Adult T cell leukemia is a cancer of the blood and bone marrow.

Viral-Induced Cervical Cancer

Infection of the cervix with human papillomavirus (HPV) is the most common cause of cervical cancer. Not all women with HPV infection, however, will develop cervical cancer. Cervical cancer usually develops slowly over time. Before cancer appears in the cervix, the cells of the cervix go through changes known as dysplasia, in which cells that are not normal begin to appear in the cervical tissue. Later, cancer cells start to grow and spread more deeply into the cervix and to surrounding areas.

The methods provided herein may provide a beneficial effect for virally induced cancers, by administration of a catecholic butane or a combination of administration of a catecholic butane and one or more anticancer treatments.

Central Nervous System (CNS) Cancers

Brain and spinal cord tumors are abnormal growths of tissue found inside the skull or the bony spinal column, which are the primary components of the central nervous system (CNS). Benign tumors are non-cancerous, and malignant tumors are cancerous. The CNS is housed within rigid, bony quarters (i.e., the skull and spinal column), so any abnormal growth, whether benign or malignant, can place pressure on sensitive tissues and impair function. Tumors that originate in the brain or spinal cord are called primary tumors. Most primary tumors are caused by out-of-control growth among cells that surround and support neurons. In a small number of individuals, primary tumors may result from specific genetic disease (e.g., neurofibromatosis, tuberous sclerosis) or from exposure to radiation or cancer-causing chemicals. The cause of most primary tumors remains a mystery.

The first test to diagnose brain and spinal column tumors is a neurological examination. Special imaging techniques (computed tomography, and magnetic resonance imaging, positron emission tomography) are also employed. Laboratory tests include the EEG and the spinal tap. A biopsy, a surgical procedure in which a sample of tissue is taken from a suspected tumor, helps doctors diagnose the type of tumor.

Tumors are classified according to the kind of cell from which the tumor seems to originate. The most common primary brain tumor in adults comes from cells in the brain called astrocytes that make up the blood-brain barrier and contribute to the nutrition of the central nervous system. These tumors are called gliomas (astrocytoma, anaplastic astrocytoma, or glioblastoma multiforme) and account for 65% of all primary central nervous system tumors. Some of the tumors are, but not limited to, Oligodendroglioma, Ependymoma, Meningioma, Lymphoma, Schwannoma, and Medulloblastoma.

Neuroepithelial Tumors of the CNS

Astrocytic tumors, such as astrocytoma,; anaplastic (malignant) astrocytoma, such as hemispheric, diencephalic, optic, brain stem, cerebellar; glioblastoma multiforme; pilocytic astrocytoma, such as hemispheric, diencephalic, optic, brain stem, cerebellar; subependymal giant cell astrocytoma; and pleomorphic xanthoastrocytoma. Oligodendroglial tumors, such as oligodendroglioma; and anaplastic (malignant) oligodendroglioma. Ependymal cell tumors, such as ependymoma,; anaplastic ependymoma; myxopapillary ependymoma; and subependymoma. Mixed gliomas, such as mixed oligoastrocytoma; anaplastic (malignant) oligoastrocytoma; and others (e.g. ependymo-astrocytomas). Neuroepithelial tumors of uncertain origin, such as polar spongioblastoma; astroblastoma; and gliomatosis cerebri. Tumors of the choroid plexus, such as choroid plexus papilloma; and choroid plexus carcinoma (anaplastic choroid plexus papilloma). Neuronal and mixed neuronal-glial tumors, such as gangliocytoma; dysplastic gangliocytoma of cerebellum (Lhermitte-Duclos); ganglioglioma; anaplastic (malignant) ganglioglioma; desmoplastic infantile ganglioglioma, such as desmoplastic infantile astrocytoma; central neurocytoma; dysembryoplastic neuroepithelial tumor; olfactory neuroblastoma (esthesioneuroblastoma). Pineal Parenchyma Tumors, such as pineocytoma; pineoblastoma; and mixed pineocytoma/pineoblastoma. Tumors with neuroblastic or glioblastic elements (embryonal tumors), such as medulloepithelioma; primitive neuroectodermal tumors with multipotent differentiation, such as medulloblastoma; cerebral primitive neuroectodermal tumor; neuroblastoma; retinoblastoma; and ependymoblastoma.

Other CNS Neoplasms

Tumors of the Sellar Region, such as pituitary adenoma; pituitary carcinoma; and craniopharyngioma. Hematopoietic tumors, such as primary malignant lymphomas; plasmacytoma; and granulocytic sarcoma. Germ Cell Tumors, such as germinoma; embryonal carcinoma; yolk sac tumor (endodermal sinus tumor); choriocarcinoma; teratoma; and mixed germ cell tumors. Tumors of the Meninges, such as meningioma; atypical meningioma; and anaplastic (malignant) meningioma. Non-menigothelial tumors of the meninges, such as Benign Mesenchymal; Malignant Mesenchymal; Primary Melanocytic Lesions; Hemopoietic Neoplasms; and Tumors of Uncertain Histogenesis, such as hemangioblastoma (capillary hemangioblastoma). Tumors of Cranial and Spinal Nerves, such as schwannoma (neurinoma, neurilemoma); neurofibroma; malignant peripheral nerve sheath tumor (malignant schwannoma), such as epithelioid, divergent mesenchymal or epithelial differentiation, and melanotic. Local Extensions from Regional Tumors; such as paraganglioma (chemodectoma); chordoma; chodroma; chondrosarcoma; and carcinoma. Metastatic tumors, Unclassified Tumors and Cysts and Tumor-like Lesions, such as Rathke cleft cyst; Epidermoid; dermoid; colloid cyst of the third ventricle; enterogenous cyst; neuroglial cyst; granular cell tumor (choristoma, pituicytoma); hypothalamic neuronal hamartoma; nasal glial herterotopia; and plasma cell griuloma.

The methods provided herein may provide a beneficial effect for CNS neoplasms, by administration of a catecholic butane or a combination of administration of a catecholic butane and one or more anticancer treatments.

Peripheral Nervous System (PNS) Cancers

The peripheral nervous system consists of the nerves that branch out from the brain and spinal cord. These nerves form the communication network between the CNS and the body parts. The peripheral nervous system is further subdivided into the somatic nervous system and the autonomic nervous system. The somatic nervous system consists of nerves that go to the skin and muscles and is involved in conscious activities. The autonomic nervous system consists of nerves that connect the CNS to the visceral organs such as the heart, stomach, and intestines. It mediates unconscious activities.

Acoustic neuromas are benign fibrous growths that arise from the balance nerve, also called the eighth cranial nerve or vestibulocochlear nerve. These tumors are non-malignant, meaning that they do not spread or metastasize to other parts of the body. The location of these tumors is deep inside the skull, adjacent to vital brain centers in the brain stem. As the tumors enlarge, they involve surrounding structures which have to do with vital functions. In the majority of cases, these tumors grow slowly over a period of years.

The malignant peripheral nerve sheath tumor (MPNST) is the malignant counterpart to benign soft tissue tumors such as neurofibromas and schwannomas. It is most common in the deep soft tissue, usually in close proximity of a nerve trunk. The most common sites include the sciatic nerve, brachial plexus, and sarcal plexus. The most common symptom is pain which usually prompts a biopsy. It is a rare, aggressive, and lethal orbital neoplasm that usually arises from sensory branches of the trigeminal nerve in adults. Malignant PNS tumor spreads along nerves to involve the brain, and most patients die within 5 years of clinical diagnosis. The MPNST may be classified into three major categories with epithelioid, mesenchymal or glandular characteristics. Some of the MPNST include but not limited to, Subcutaneous malignant epithelioid schwannoma with cartilaginous differentiation, Glandular malignant schwannoma, Malignant peripheral nerve sheath tumor with perineurial differentiation, Cutaneous epithelioid malignant nerve sheath tumor with rhabdoid features, Superficial epithelioid MPNST, Triton Tumor (MPNST with rhabdomyoblastic differentiation), Schwannoma with rhabdomyoblastic differentiation. Rare MPNST cases contain multiple sarcomatous tissue types, especially osteosarcoma, chondrosarcoma and angiosarcoma. These have sometimes been indistinguishable from the malignant mesenchymoma of soft tissue.

Other types of PNS cancers include but not limited to, malignant fibrous cytoma, malignant fibrous histiocytoma, malignant meningioma, malignant mesothelioma, and malignant mixed Müllerian tumor.

The methods provided herein may provide a beneficial effect for PNS cancers, by administration of a catecholic butane or a combination of administration of a catecholic butane and one or more anticancer treatments.

Oral Cavity and Oropharyngeal Cancer

Management of patients with central nervous system (CNS) cancers remains a formidable task. Cancers such as, hypopharyngeal cancer, laryngeal cancer, nasopharyngeal cancer, oropharyngeal cancer, may be treated using the compounds described herein.

The methods provided herein may provide a beneficial effect for oral cavity and oropharyngeal cancer, by administration of a catecholic butane or a combination of administration of a catecholic butane and one or more anticancer treatments Stomach Cancer Stomach cancer is the result of cell changes in the lining of the stomach. There are three main types of stomach cancers: lymphomas, gastric stromal tumors, and carcinoid tumors. Lymphomas are cancers of the immune system tissue that are sometimes found in the wall of the stomach. Gastric stromal tumors develop from the tissue of the stomach wall. Carcinoid tumors are tumors of hormone-producing cells of the stomach. The causes of stomach cancer continue to be debated. A combination of heredity and environment (diet, smoking, etc) are all thought to play a part.

The methods provided herein may provide a beneficial effect for stomach cancer, by administration of a catecholic butane or a combination of administration of a catecholic butane and one or more anticancer treatments.

Testicular Cancer

Testicular cancer is cancer that typically develops in one or both testicles in young men. Cancers of the testicle develop in certain cells known as germ cells. The 2 main types of germ cell tumors (GCTs) that occur in men are seminomas (60%) and nonseminomas (40%). Tumors can also arise in the supportive and hormone-producing tissues, or stroma, of the testicles. Such tumors are known as gonadal stromal tumors. The 2 main types are Leydig cell tumors and Sertoli cell tumors. Secondary testicular tumors are those that start in another organ and then spread to the testicle. Lymphoma is the most common secondary testicular cancer.

The methods provided herein may provide a beneficial effect for testicular cancer, by administration of a catecholic butane or a combination of administration of a catecholic butane and one or more anticancer treatments.

Thymus Cancer

The thymus is a small organ located in the upper/front portion of your chest, extending from the base of the throat to the front of the heart. The thymus contains 2 main types of cells, thymic epithelial cells and lymphocytes. Thymic epithelial cells can give origin to thymomas and thymic carcinomas. Lymphocytes, whether in the thymus or in the lymph nodes, can become malignant and develop into cancers called Hodgkin disease and non-Hodgkin lymphomas. The thymus also contains another much less common type of cells called Kulchitsky cells, or neuroendocrine cells, which normally release certain hormones. These cells can give rise to cancers, called carcinoids or carcinoid tumors that often release the same type of hormones, and are similar to other tumors arising from neuroendocrine cells elsewhere in the body.

The methods provided herein may provide a beneficial effect for thymus cancer, by administration of a catecholic butane or a combination of administration of a catecholic butane and one or more anticancer treatments.

Provided herein are methods for treating a disorder of the skin, comprising administering an effective amount of a pharmaceutical compound capable of inhibiting the tyrosine kinase activity of IGF-1R and EGFR, wherein the pharmaceutical compound is a catecholic butane.

In one aspect, the disorder of the skin is for example, a tumor, actinic keratosis, acne, psoriasis, skin wounds, warts, bacterial infections, fungal infections or viral infections. Viral infections include, but are not limited to, an HIV infection, an HPV infection and an HSV infection. Tumors include, but are not limited to, basal cell carcinomas, squamous cell carcinomas, melanomas, Dermatofibrosarcoma protuberans, Merkel cell carcinoma and Kaposi's sarcoma.

Colon Cancer and Colorectal Cancer

Colorectal cancer, also called colon cancer or large bowel cancer, includes cancerous growths in the colon, rectum and appendix. With 655,000 deaths worldwide per year, it is the third most common form of cancer and the second leading cause of cancer-related death in the Western world. Many colorectal cancers are thought to arise from adenomatous polyps in the colon. These mushroom-like growths are usually benign, but some may develop into cancer over time.

In another embodiment, Dukes classification may be used to classify colorectal cancer based on stages A-D. Stage A refers to colorectal cancer that is limited to mucosa (i.e., has not invaded through the bowel wall). Stage B1 refers to extending into muscularis propria, but not penetrating through it (i.e., lymph nodes have not been invaded); whereas Stage B2 cancer has penetrated through the muscularis propria, but not penetrating through it (i.e., lymph nodes have not been invaded). Stage C1 refers to cancer that extends into the muscularis propria, but not penetrating through it (i.e., lymph nodes are involved); whereas Stage C2 refers to cancer that extends into the muscularis propria and penetrating through it (i.e., lymph nodes are involved). Stage D refers to distant metastatic spread. The TNM system may also be used to stage colorectal cancer according to conventional means known in the art.

The methods provided herein may provide a beneficial effect for colorectal cancer, by administration of a catecholic butane or a combination of administration of a catecholic butane and one or more anticancer treatments.

Dosing

A physician or veterinarian can readily determine and prescribe the "effective amount" (ED50) of a composition required to inhibit both EGFR and IGF-1R. For example, the physician or veterinarian could start doses of the compounds employed in the composition at levels lower than that required in order to achieve the desired therapeutic effect and gradually increase the dosage until the desired effect is achieved.

A "therapeutically effective amount" as used herein, is an amount that achieves at least partially a desired therapeutic or prophylactic effect in an organ or tissue. In one example, the amount of an inhibitor to bring about prevention and/or therapeutic treatment of the disease is not fixed per se. The amount of an inhibitor administered will vary with the type of disease, extent of the disease, and size of species of the mammal suffering from the disease.

One embodiment contemplates the use of the compositions described herein to make a medicament for treating a condition, disease or disorder described herein. Medicaments can be formulated based on the physical characteristics of the patient/subject needing treatment, and can be formulated in single or multiple formulations based on the stage of the condition, disease or disorder. Medicaments can be packaged in a suitable package with appropriate labels for the distribution to hospitals and clinics wherein the label is for the indication of treating a subject having a disease described herein.

Medicaments can be packaged as a single or multiple units. Instructions for the dosage and administration of the compositions can be included with the packages as described elsewhere herein.

Pharmaceutical compositions of the present embodiments may be formulated for dosage by any route of administration such as, for example, intranasal administration; oral administration; inhalation administration; subcutaneous administration; transdermal administration; intra-arterial administration, with or without occlusion; intracranial administration; intraventricular administration; intravenous administration; buccal administration; intraperitoneal administration; intraocular administration; intramuscular administration; implantation administration; and central venous administration. In one embodiment, the catecholic butane is formulated for oral administration. In another embodiment, the catecholic butane is formulated for intravenous administration.

Catecholic butanes may be administered in an amount of about 5 mg/kg to about 375 mg/kg per dose; about 5 mg/kg to about 250 mg/kg per dose; about 5 mg/kg to about 200 mg/kg per dose; about 5 mg/kg to about 150 mg/kg per dose; about 5 mg/kg to about 100 mg/kg per dose; about 5 mg/kg to about 75 mg/kg per dose; or about 5 mg/kg to about 50 mg/kg per dose. Alternatively, catecholic butanes may be administered a flat dose of a catecholic butane in an amount of from about 1,500 mg per day to about 2,500 mg per day; from about 1,800 mg per day to about 2,300 mg per day; or about 2,000 mg per day. In one embodiment, a catecholic butane may be contacted with target cells in a concentration in a range of about 1 µM to about 30 µM. In another embodiment, a catecholic butane may be contacted with target cells in a concentration in a range of about 1 µM to about 10 µM.

In another embodiment, NDGA may be administered in different dosing and administration schedules such as, for example: (1) twice-daily oral administration on days 1-28. Treatment repeats every 28 days in the absence of disease progression or unacceptable toxicity; (2) 2000 mg once-daily oral administration; (3) IV on days 1-5, treatment repeats every 28 days in the absence of disease progression or unacceptable toxicity; (4) dose escalation with starting schedule to a target of 20 mg/cm3 tumor volume and then, new patient cohorts will have their schedule extended to weekly administration for 4 weeks. Dose escalation will continue, assuming tolerability, so that cohorts will be treated for 6 weeks, and finally, 8 weeks; (5) IV weekly over 24 hours, dose will commence with 100 mg/hour (2400 mg in a 24-hour period) with escalation in 5 cohorts of 3 to 6 patients with increments of 25 mg per hour to a maximum of 200 mg/hr (4800 mg in a 24-hour period) or until MTD is defined; (6) topical application to the cervix; and (7) dose escalation with IV infusion for 5 consecutive days every 28 days.

In one embodiment, a pharmaceutical composition may be administered more frequently than once every 6 days for a period of time, or more frequently than once every 2 days for a period of time. In one embodiment, a pharmaceutical composition is administered daily for four weeks. In another embodiment, a pharmaceutical composition is administered three times daily for three weeks with a one week hiatus prior to starting a new cycle. In another embodiment, a pharmaceutical composition is administered daily for one week followed by a one week hiatus. In another embodiment, a pharmaceutical composition is administered daily for two weeks followed by a two week hiatus. In another embodiment, a pharmaceutical composition is administered one time or two times daily continuously or with a one week hiatus prior to starting a new cycle. In yet another embodiment, a pharmaceutical composition is administered one time per week or two times per week. One would understand that, as needed, where cycles of treatment are considered, a patient may be assessed and the treatment repeated as needed.

In various embodiments, a catecholic butane may be prepared as a free base or a pharmaceutically acceptable salt, solvate, polymorph, ester, tautomer or prodrug thereof. Also described, are pharmaceutical compositions comprising a catecholic butane or a pharmaceutically acceptable salt, solvate, polymorph, ester, tautomer or prodrug thereof. The compounds and compositions described herein may be administered either alone or in combination with pharmaceutically acceptable carriers, excipients or diluents, in a pharmaceutical composition, according to standard pharmaceutical practice.

In addition to the aforementioned examples and embodiments of dosages, cycles, and schedules of cycles, numerous permutations of the aforementioned dosages, cycles, and schedules of cycles for the co-administration of a compound with a second chemotherapeutic compound, radiotherapy, or surgery are contemplated herein and can be administered according to the patient, type of cancer, and/or appropriate treatment schedule as determined by qualified medical professionals.

In various embodiments, a therapeutically equivalent amount of a catecholic butane dose described herein is used.

In various embodiments, the catecholic butane is dosed in so as to minimize toxicity to the patient. In some embodiments, the catecholic butane is dosed in a manner adapted to provide particular pharmacokinetic (PK) parameters in a human patient. In some embodiments, the catecholic butane is dosed in a manner adapted to provide a particular maximum blood concentration ($C_{max}$) of the catecholic butane. In some embodiments, the catecholic butane is dosed in a manner adapted to provide a particular time ($T_{max}$) at which a maximum blood concentration of the catecholic butane is obtained. In some embodiments, the catecholic butane is dosed in a manner adapted to provide a particular area under the blood plasma concentration curve (AUC) for the catecholic butane. In some embodiments, the catecholic butane is dosed in a manner to provide a particular clearance rate (CL/F) or a particular half-life ($T_{1/2}$) for the catecholic butane. Unless otherwise specified herein, the PK parameters recited herein, including in the appended claims, refer to mean PK values for a cohort of at least 3 patients under the same dosing schedule. Thus, unless otherwise specified: AUC=mean AUC for a cohort of at least 3 patients; $C_{max}$=mean $C_{max}$ for a cohort of at least 3 patients; $T_{max}$=mean $T_{max}$ for a cohort of at least 3 patients; $T_{1/2}$=mean $T_{1/2}$ for a cohort of at least 3 patients; and CL/F=mean CL/F for a cohort of at least 3 patients. In some embodiments, the mean is a cohort of at least 6 patients, or at least 12 patients or at least 24 patients or at least 36 patients. Where other than mean PK values are intended, it will be indicated that the value pertains to individuals only. Also, unless otherwise indicated herein, AUC refers to the mean AUC for the cohort of at least 3 patients, extrapolated to infinity following a standard clearance model. If AUC for a time certain is intended, the start (x) and end (y) times will be indicated by suffix appellation to "AUC" (e.g., $AUC_{x,y}$).

Combination Therapy

One aspect of the embodiments described herein provides methods for treating cancer using different combinations of treatment regimens. For example, such catecholic butane compounds in conjunction with one or more various antineoplastic chemotherapeutic agents, chemopreventative agents, side-effect limiting agents, and/or antineoplastic treatments (e.g., surgery).

In any of such methods provided herein, a subject may be further administered one or more additional anti cancer agents. As described above, these additional cancer therapies can be, for example, surgery, radiation therapy, administration of chemotherapeutic agents and combinations of any two or all of these methods. Combination treatments may occur sequentially or concurrently and the combination therapies may be neoadjuvant therapies or adjuvant therapies. Anticancer agents include, but are not limited to, DNA damaging agents, topoisomerase inhibitors and mitotic inhibitors. Many chemotherapeutics are presently known in the art and can be used in combination with the compounds described herein. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

In one embodiment, the subject to be treated may be resistant to treatment with at least one tyrosine kinase inhibitor, for example an EGFR inhibitor alone, an IGF-1R inhibitor alone, or an EGFR inhibitor and an IGF-1R inhibitor.

As used herein, the terms "cancer treatment," "cancer therapy" and the like encompasses treatments such as surgery such as cutting, abrading, ablating (by physical or chemical means, or a combination of physical or chemical means), suturing, lasering or otherwise physically changing body tissues and organs), radiation therapy, administration of chemotherapeutic agents and combinations of any two or all of these methods. Combination treatments may occur sequentially or concurrently. Treatments, such as radiation therapy and/or chemotherapy, that is administered prior to surgery, are referred to as neoadjuvant therapy. Treatments, such as radiation therapy and/or chemotherapy, administered after surgery is referred to herein as adjuvant therapy. Examples of surgeries that may be used for cancer treatment include, but are not limited to radical prostatectomy, cryotherapy, mastectomy, lumpectomy, transurethral resection of the prostate, and the like.

Many chemotherapeutic agents are known and operate via a wide variety of modes of action. In some non-limiting embodiments, the chemotherapeutic agent is a cytotoxic agent, an anti-proliferative, a targeting agent (such as kinase inhibitors and cell cycle regulators), or a biologic agent (such as cytokines, vaccines, viral agents, and other immunostimulants such as BCG, hormones, monoclonal antibodies and siRNA). The nature of a combination therapy involving administration of a chemotherapeutic agent will depend upon the type of agent being used.

Where combination treatments are contemplated, it is not intended that an inhibitor be limited by the particular nature of the combination. For example, an inhibitor may be administered in combination as simple mixtures as well as chemical hybrids. An example of the latter is where the compound is covalently linked to a targeting carrier or to an active pharmaceutical. Covalent binding can be accomplished in many ways, such as, though not limited to, the use of a commercially available cross-linking compound.

As used herein, the terms "pharmaceutical combination," "administering an additional therapy," "administering an additional therapeutic agent" and the like refer to a pharmaceutical therapy resulting from the mixing or combining of more than one active ingredient and includes both fixed and non-fixed combinations of the active ingredients. The term "fixed combination" means that an inhibitor, and at least one co-agent, are both administered to a patient simultaneously in the form of a single entity or dosage. The term "non-fixed combination" means that an inhibitor, and at least one co-agent, are administered to a patient as separate entities either simultaneously, concurrently or sequentially with variable intervening time limits, wherein such administration provides effective levels of the two or more compounds in the body of the patient. These also apply to cocktail therapies, e.g., the administration of three or more active ingredients.

As used herein, the terms "co-administration," "administered in combination with" and their grammatical equivalents or the like are meant to encompass administration of the selected therapeutic agents to a single patient, and are intended to include treatment regimens in which the agents are administered by the same or different route of administration or at the same or different times. In some embodiments, an inhibitor will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, an inhibitor and the other agent(s) are administered in a single composition. In some embodiments, an inhibitor and the other agent(s) are admixed in the composition.

As used herein, "anti-cancer agents or treatments" refer to, but are not limited to, a chemotherapeutic agent, a nucleic acid damaging agent, a nucleic acid damaging treatment, an anticancer antibody, an anti-proliferative agent, or an anti-proliferative treatment to the subject. One would understand that the listing of therapeutic regimens listed below represents conventional therapies, but the present embodiments encompass other known therapeutic regimens which are not specifically disclosed herein.

Suitable antineoplastic chemotherapeutic agents to be used in the present methods include, but are not limited to, alkylating agents, antimetabolites, natural antineoplastic agents, hormonal antineoplastic agents, angiogenesis inhibitors, differentiating reagents, RNA inhibitors, antibodies or immunotherapeutic agents, gene therapy agents, small molecule enzymatic inhibitors, biological response modifiers, and antimetastatic agents.

Alkylating Agents

Alkylating agents are known to act through the alkylation of macromolecules such as the DNA of cancer cells, and are usually strong electrophiles. This activity can disrupt DNA synthesis and cell division. Examples of alkylating reagents suitable for use herein include nitrogen mustards and their analogues and derivatives including, cyclophosphamide, ifosfamide, chlorambucil, estramustine, mechlorethamine hydrochloride, melphalan, and uracil mustard. Other examples of alkylating agents include alkyl sulfonates (e.g. busulfan), nitrosoureas (e.g. carmustine, lomustine, and streptozocin), triazenes (e.g. dacarbazine and temozolomide), ethylenimines/methylmelamines (e.g. altretamine and thiotepa), and methylhydrazine derivatives (e.g. procarbazine). Included in the alkylating agent group are the alkylating-like platinum-containing drugs comprising carboplatin, cisplatin, and oxaliplatin.

Antimetabolites

Antimetabolic antineoplastic agents structurally resemble natural metabolites, and are involved in normal metabolic processes of cancer cells such as the synthesis of nucleic acids and proteins. They differ enough from the natural metabolites so that they interfere with the metabolic processes of cancer cells. Suitable antimetabolic antineoplastic agents to be used in the present methods can be classified according to the metabolic process they affect, and can include, but are not limited to, analogues and derivatives of folic acid, pyrimidines, purines, and cytidine. Members of the folic acid group of agents suitable for use herein include, but are not limited to, methotrexate (amethopterin), pemetrexed and their analogues and derivatives. Pyrimidine agents suitable for use herein include, but are not limited to, cytarabine, floxuridine, fluorouracil (5-fluorouracil), capecitabine, gemcitabine, and their analogues and derivatives. Purine agents suitable for use herein include, but are not limited to, mercaptopurine (6-mercaptopurine), pentostatin, thioguanine, cladribine, and their analogues and derivatives. Cytidine agents suitable for use herein include, but are not limited to, cytarabine (cytosine arabinodside), azacitidine (5-azacytidine) and their analogues and derivatives.

Natural Antineoplastic Agents

Natural antineoplastic agents comprise antimitotic agents, antibiotic antineoplastic agents, camptothecin analogues, and enzymes. Antimitotic agents suitable for use herein include, but are not limited to, vinca alkaloids like vinblastine, vincristine, vindesine, vinorelbine, and their analogues and derivatives. They are derived from the Madagascar periwinkle plant and are usually cell cycle-specific for the M phase, binding to tubulin in the microtubules of cancer cells. Other antimitotic agents suitable for use herein are the podophyllotoxins, which include, but are not limited to etoposide, teniposide, and their analogues and derivatives. These reagents predominantly target the G2 and late S phase of the cell cycle.

Also included among the natural antineoplastic agents are the antibiotic antineoplastic agents. Antibiotic antineoplastic agents are antimicrobial drugs that have anti-tumor properties usually through interacting with cancer cell DNA. Antibiotic antineoplastic agents suitable for use herein include, but are not limited to, belomycin, dactinomycin, doxorubicin, idarubicin, epirubicin, mitomycin, mitoxantrone, pentostatin, plicamycin, and their analogues and derivatives.

The natural antineoplastic agent classification also includes camptothecin analogues and derivatives which are suitable for use herein and include camptothecin, topotecan, and irinotecan. These agents act primarily by targeting the nuclear enzyme topoisomerase I. Another subclass under the natural antineoplastic agents is the enzyme, L-asparaginase and its variants. L-asparaginase acts by depriving some cancer cells of L-asparagine by catalyzing the hydrolysis of circulating asparagine to aspartic acid and ammonia.

Hormonal Antineoplastic Agents

Hormonal antineoplastic agents act predominantly on hormone-dependent cancer cells associated with prostate tissue, breast tissue, endometrial tissue, ovarian tissue, lymphoma, and leukemia. Such tissues may be responsive to and dependent upon such classes of agents as glucocorticoids, progestins, estrogens, and androgens. Both analogues and derivatives that are agonists or antagonists are suitable to treat tumors. Examples of glucocorticoid agonists/antagonists suitable for use herein are dexamethasone, cortisol, corticosterone, prednisone, mifepristone (RU486), their analogues and derivatives. The progestin agonist/antagonist subclass of agents suitable for use herein includes, but is not limited to, hydroxyprogesterone, medroxyprogesterone, megestrol acetate, mifepristone (RU486), ZK98299, their analogues and derivatives. Examples from the estrogen agonist/antagonist subclass of agents suitable for use herein include, but are not limited to, estrogen, tamoxifen, toremifene, RU58668, SR16234, ZD164384, ZK191703, fulvestrant, their analogues and derivatives. Examples of aromatase inhibitors suitable for use herein, which inhibit estrogen production, include, but are not limited to, androstenedione, formestane, exemestane, aminoglutethimide, anastrozole, letrozole, their analogues and derivatives. Examples from the androgen agonist/antagonist subclass of agents suitable for use herein include, but are not limited to, testosterone, dihydrotestosterone, fluoxymesterone, testolactone, testosterone enanthate, testosterone propionate, gonadotropin-releasing hormone agonists/antagonists (e.g. leuprolide, goserelin, triptorelin, buserelin), diethylstilbestrol, abarelix, cyproterone, flutamide, nilutamide, bicalutamide, their analogues and derivatives.

Angiogenesis Inhibitors

Angiogenesis inhibitors work by inhibiting the vascularization of tumors. Angiogenesis inhibitors encompass a wide variety of agents including small molecule agents, antibody agents, and agents that target RNA function. Examples of angiogenesis inhibitors suitable for use herein include, but are not limited to, ranibizumab, bevacizumab, SU11248, PTK787, ZK222584, CEP-7055, angiozyme, dalteparin, thalidomide, suramin, CC-5013, combretastatin A4 Phosphate, LY317615, soy isoflavones, AE-941, interferon alpha, PTK787/ZK 222584, ZD6474, EMD 121974, ZD6474, BAY 543-9006, celecoxib, halofuginone hydrobromide, bevacizumab, their analogues, variants, or derivatives.

Differentiating Reagents

Differentiating agents inhibit tumor growth through mechanisms that induce cancer cells to differentiate. One such subclass of these agents suitable for use herein includes, but is not limited to, vitamin A analogues or retinoids, and peroxisome proliferator-activated receptor agonists (PPARs). Retinoids suitable for use herein include, but are not limited to, vitamin A, vitamin A aldehyde (retinal), retinoic acid, fenretinide, 9-cis-retinoid acid, 13-cis-retinoid acid, all-trans-retinoic acid, isotretinoin, tretinoin, retinal palmitate, their analogues and derivatives. Agonists of PPARs suitable for use herein include, but are not limited to, troglitazone, ciglitazone, tesaglitazar, their analogues and derivatives.

RNA Inhibitors

Certain RNA inhibiting agents may be utilized to inhibit the expression or translation of messenger RNA ("mRNA") that is associated with a cancer phenotype. Examples of such agents suitable for use herein include, but are not limited to, short interfering RNA ("siRNA"), ribozymes, and antisense oligonucleotides. Specific examples of RNA inhibiting agents suitable for use herein include, but are not limited to, Candy, Sirna-027, fomivirsen, and angiozyme.

Antibodies/Immunotherapeutic Agents

Antibody agents bind targets selectively expressed in cancer cells and can either utilize a conjugate to kill the cell associated with the target, or elicit the body's immune response to destroy the cancer cells. Immunotherapeutic agents can either be comprised of polyclonal or monoclonal antibodies. The antibodies may be comprised of non-human animal (e.g. mouse) and human components, or be comprised of entirely human components ("humanized antibodies"). Examples of monoclonal immunotherapeutic agents suitable for use herein include, but are not limited to, rituximab, tositumomab, ibritumomab which target the CD-20 protein. Other examples suitable for use herein include trastuzumab, edrecolomab, bevacizumab, cetuximab, carcinoembryonic antigen antibodies, gemtuzumab, alemtuzumab, mapatumumab, panitumumab, EMD 72000, TheraCIM hR3, 2C4, HGS-TR2J, and HGS-ETR2.

Gene Therapy Agents

Gene therapy agents insert copies of genes into a specific set of a patient's cells, and can target both cancer and non-cancer cells. The goal of gene therapy can be to replace altered genes with functional genes, to stimulate a patient's immune response to cancer, to make cancer cells more sensitive to chemotherapy, to place "suicide" genes into cancer cells, or to inhibit angiogenesis. Genes may be delivered to target cells using viruses, liposomes, or other carriers or vectors. This may be done by injecting the gene-carrier composition into the patient directly, or ex vivo, with infected cells being introduced back into a patient. Such compositions are suitable for use in the present methods.

Small Molecule Enzymatic Inhibitors

Certain small molecule therapeutic agents are able to target the tyrosine kinase enzymatic activity or downstream signal transduction signals of certain cell receptors such as epidermal growth factor receptor ("EGFR") or vascular endothelial growth factor receptor ("VEGFR"). Such targeting by small molecule therapeutics can result in anti-cancer effects. Examples of such agents suitable for use herein include, but are not limited to, imatinib, gefitinib, erlotinib, lapatinib, canertinib, ZD6474, sorafenib (BAY 43-9006), ERB-569, and their analogues and derivatives.

Biological Response Modifiers

Certain protein or small molecule agents can be used in anti-cancer therapy through either direct anti-tumor effects or through indirect effects. Examples of direct-acting agents suitable for use herein include, but are not limited to, differentiating reagents such as retinoids and retinoid derivatives. Indirect-acting agents suitable for use herein include, but are not limited to, agents that modify or enhance the immune or other systems such as interferons, interleukins, hematopoietic growth factors (e.g. erythropoietin), and antibodies (monoclonal and polyclonal).

Anti-Metastatic Agents

The process whereby cancer cells spread from the site of the original tumor to other locations around the body is termed cancer metastasis. Certain agents have anti-metastatic properties, designed to inhibit the spread of cancer cells. Examples of such agents suitable for use herein include, but are not limited to, marimastat, bevacizumab, trastuzumab, rituximab, erlotinib, MMI-166, GRN163L, hunter-killer peptides, tissue inhibitors of metalloproteinases (TIMPs), their analogues, derivatives and variants.

Chemopreventative Agents

Certain pharmaceutical agents can be used to prevent initial occurrences of cancer, or to prevent recurrence or metastasis. Administration with such chemopreventative agents in combination with one or more other anticancer agents including the catecholic butanes can act to both treat and prevent the recurrence of cancer. Examples of chemopreventative agents suitable for use herein include, but are not limited to, tamoxifen, raloxifene, tibolone, bisphosphonate, ibandronate, estrogen receptor modulators, aromatase inhibitors (letrozole, anastrozole), luteinizing hormone-releasing hormone agonists, goserelin, vitamin A, retinal, retinoic acid, fenretinide, 9-cis-retinoid acid, 13-cis-retinoid acid, all-trans-retinoic acid, isotretinoin, tretinoid, vitamin B6, vitamin B12, vitamin C, vitamin D, vitamin E, cyclooxygenase inhibitors, non-steroidal anti-inflammatory drugs (NSAIDs), aspirin, ibuprofen, celecoxib, polyphenols, polyphenol E, green tea extract, folic acid, glucaric acid, interferon-alpha, anethole dithiolethione, zinc, pyridoxine, finasteride, doxazosin, selenium, indole-3-carbinal, alpha-difluoromethylornithine, carotenoids, beta-carotene, lycopene, antioxidants, coenzyme Q10, flavonoids, quercetin, curcumin, catechins, epigallocatechin gallate, N-acetylcysteine, indole-3-carbinol, inositol hexaphosphate, isoflavones, glucanic acid, rosemary, soy, saw palmetto, and calcium.

Side-Effect Limiting Agents

Treatment of cancer with catecholic butanes alone or in combination with other antineoplastic compounds may be accompanied by administration of pharmaceutical agents that can alleviate the side effects produced by the antineoplastic agents. Such agents suitable for use herein include, but are not limited to, anti-emetics, anti-mucositis agents, pain management agents, infection control agents, and anti-anemia/anti-thrombocytopenia agents. Examples of anti-emetics suitable for use herein include, but are not limited to, 5-hydroxytryptamine 3 receptor antagonists, metoclopramide, steroids, lorazepam, ondansetron, cannabinoids, their analogues and derivatives. Examples of anti-mucositis agents suitable for use herein include, but are not limited to, palifermin (keratinocyte growth factor), glucagon-like peptide-2, teduglutide, L-glutamine, amifostin, and fibroblast growth factor 20. Examples of pain management agents suitable for use herein include, but are not limited to, opioids, opiates, and non-steroidal anti-inflammatory compounds. Examples of agents used for control of infection suitable for use herein include, but are not limited to, antibacterials such as aminoglycosides, penicillins, cephalosporins, tetracyclines, clindamycin, lincomycin, macrolides, vancomycin, carbapenems, monobactams, fluoroquinolones, sulfonamides, nitrofurantoins, their analogues and derivatives. Examples of agents that can treat anemia or thrombocytopenia associated with chemotherapy suitable for use herein include, but are not limited to, erythropoietin, and thrombopoietin.

Several other suitable therapies for use in combination with the catecholic butanes and other compounds described herein are also available. For example, see *Goodman & Gilman's The Pharmacological Basis of Therapeutics* 11th ed. Brunton L L, Lazo J S, and Parker K L, ed. McGraw-Hill, New York, 2006.

Ovarian Cancer

In one embodiment, the cancer is ovarian cancer and the one or more therapeutic treatments is surgery, chemotherapy (e.g., doxorubicin, doxil, gemcitabine, Rubitecan, and platinum-based chemotherapeutics such as cisplatin, carboplatin and oxaliplatin), melphalan, paclitaxel, topoisomerase I inhibitors such as topotecan and irinotecan, taxane-based therapy, hormones, radiation therapy, whole body hyperthermia, isoflavone derivatives such as Phenoxodial, cytotoxic macrolides such as Epothilones, angiogenesis inhibitors such as bevacizumab, signal transduction inhibitors such as trastuzumab, gene therapy, RNAi therapy, immunotherapy, monoclonal antibodies, phosphatidylinositol-like kinase inhibitors such as rapamycin, or any combination thereof. In yet another embodiment the therapeutic treatment is a VEGF receptor inhibitor. Non-limiting examples of VEGF receptor inhibitors include bevacizumab (AVASTIN®), ranibizumab (LUCENTIS®), VEGF-Trap, sunitinib (SUTENT®), sorafenib (NEXAVAR®), axitinib, pegaptanib and pazopanib.

Liver Cancer

In one embodiment, the cancer is liver cancer and the one or more anticancer treatments is, for example, surgery, immunotherapy, radiation therapy, chemotherapy and percutaneous ethanol injection. The types of surgery that may be used are cryosurgery, partial hepatectomy, total hepatectomy and radiofrequency ablation. Radiation therapy may be external beam radiation therapy, brachytherapy, radiosensitizers or radiolabel antibodies. Other types of treatment include hyperthermia therapy and immunotherapy.

Skin Cancer

Different types of treatment are available for patients with non-melanoma and melanoma skin cancer and actinic keratosis including surgery, radiation therapy, chemotherapy and photodynamic therapy. Some possible surgical options for treatment of skin cancer are mohs micrographic surgery, simple excision, electrodesiccation and curettage, cryosurgery, laser surgery. Radiation therapy may be external beam radiation therapy or brachytherapy. Other types of treatments that are being tested in clinical trials are biologic therapy or immunotherapy, chemoimmunotherapy, topical chemotherapy with fluorouracil and photodynamic therapy.

Endometrium Cancer

In one embodiment, the cancer is endometrium cancer and the one or more anticancer treatments is, for example, surgery, radiation therapy, chemotherapy, gene therapy, photodynamic therapy, antiangiogenesis therapy, and immunotherapy, or a combination thereof.

Renal/Kidney Cancer

In one embodiment, the cancer is renal/kidney cancer and the one or more therapeutic treatments is surgery, chemotherapy, bevacizumab (AVASTIN®), ranibizumab (LUCENTIS®), VEGF-Trap, sunitinib (SUTENT®), sorafenib (NEXAVAR®), axitinib, pegaptanib, pazopanib, interferon-alpha, IL-2, or any combination thereof.

Testicular Cancer

In one embodiment, the cancer is testicular cancer and the one or more anticancer treatments is, for example, surgery, immunotherapy, chemotherapy, radiation therapy, combination of chemotherapy and radiation therapy or biological therapy. Several drugs are typically used to treat testicular cancer: Platinol (cisplatin), Vepesid or VP-16 (etoposide) and Blenoxane (bleomycin sulfate). Additionally, Ifex (ifosamide), Velban (vinblastine sulfate) and others may be used.

Stomach Cancer

In one embodiment, the cancer is testicular cancer and the one or more anticancer treatments is, for example, surgery, immunotherapy, chemotherapy, radiation therapy, combination of chemotherapy and radiation therapy or biological therapy.

Thymus Cancer

In one embodiment, the cancer is thymus cancer and the one or more anticancer treatments is, for example, surgery, immunotherapy, chemotherapy, radiation therapy, combination of chemotherapy and radiation therapy or biological therapy. Anticancer drugs that have been used in the treatment of thymomas and thymic carcinomas are doxorubicin (Adriamycin), cisplatin, ifosfamide, and corticosteroids (prednisone). Often, these drugs are given in combination to increase their effectiveness. Combinations used to treat thymic cancer include cisplatin, doxorubicin, etoposide and cyclophosphamide, and the combination of cisplatin, doxorubicin, cyclophosphamide, and vincristine.

Myeloma

In one embodiment, the cancer is myeloma and the one or more therapeutic treatments is surgery, radiotherapy, VELCADE®, lenalidomide, or thalidomide, or a combination thereof. In one embodiment, the therapeutic treatment is VELCADE®. The dosages for any of these therapies are known in the art and can be adjusted with combination therapy accordingly.

Prostate Cancer

In one embodiment, the cancer is prostate cancer and the one or more therapeutic treatments is surgery, radiotherapy (e.g., external beam or brachytherapy), hormonal deprivation (androgen suppression), heat shock protein 90 (HSP90) inhibitors, chemotherapy (e.g., docetaxel, platinum-based chemotherapy such as cisplatin, carboplatin, satraplatin and oxaliplatin, taxane, estramustine), prednisone or prednisolone, cholesterol-lowering drugs such as statins, leutinizing hormone-releasing hormone (LHRH) agonists, RNAi therapy, whole tumor cells genetically modified to secrete granulocyte macrophage—colony stimulating factor (GM-CSF) (also known as GVAX), or any combination thereof. In yet another embodiment, the one or more therapeutic treatments is a VEGF receptor inhibitor. Non-limiting examples of VEGF receptor inhibitors include bevacizumab (AVASTIN®), ranibizumab (LUCENTIS®), VEGF-Trap, sunitinib (SUTENT®), sorafenib (NEXAVAR®), axitinib, pegaptanib and pazopanib.

Lung Cancer

In one embodiment, the cancer is lung cancer and the one or more therapeutic treatments is surgery, radiotherapy (e.g., thoracic radiotherapy, radiation therapy with charged particles, Uracil-tegafur and Platinum-based chemotherapy (e.g., cisplatin, carboplatin, oxaliplatin, etc.) and vinorebline, Erlotinib (TARCEVA®), Gefitinib (IRESSA®), anti-epidermal growth factor receptor antibodies (e.g., Cetuximab), anti-vascular endothelial growth factor antibodies (e.g., Bevacizumab), small molecule inhibitors of tyrosine kinases, direct inhibitors of proteins involved in lung cancer cell proliferation, Aurora kinase inhibitors, laser-induced thermotherapy, RNAi therapy, whole tumor cells genetically modified to secrete granulocyte macrophage—colony stimulating factor (GM-CSF) (also known as GVAX), bevacizumab (AVASTIN®), ranibizumab (LUCENTIS®), VEGF-Trap, sunitinib (SUTENT®), sorafenib (NEXAVAR®), axitinib, pegaptanib and pazopanib, or any combination thereof. Additional therapeutic treatments include Taxol and pemetrexed. The dosages for any of these therapies are known in the art and can be adjusted with combination therapy accordingly.

Breast Cancer

In one embodiment, the cancer is breast cancer and the one or more therapeutic treatments is surgery, monoclonal antibodies (e.g., Her-2 antibodies, herceptin, bevacizumab (AVASTIN®), ranibizumab (LUCENTIS®), sunitinib (SUTENT®), sorafenib (NEXAVAR®), axitinib, pegaptanib and pazopanib), adjuvant chemotherapy such as single agent chemotherapy or combination chemotherapy (e.g., anthracycline- and taxane-based polychemotherapies, taxol, or target-specific trastuzumab with or without endocrine manipulation with or without PMRT, vinorelbine), VEGF-Trap, xeloda, taxotere, adriamycin, cyclophosphamide, xeloda, taxotere, selective estrogen receptor modulators such as Tamoxifen and Raloxifene, allosteric estrogen receptor modulators such as Trilostane, radiation (e.g., interstitial brachytherapy, Mammosite device, 3-dimensional conformal external radiation and intraoperative radiotherapy), Aromatase inhibitors that suppress total body synthesis (e.g., anastrozole, exemestane and letrozole), RNAi therapy, intravenous analogs of rapamycin that are immunosuppressive and anti-proliferative such as Temsirolimus (CCI779), or any combination thereof. The dosages for any of these therapies are known in the art and can be adjusted with combination therapy accordingly.

Colon Cancer

In one embodiment, the cancer is colon cancer and the one or more therapeutic treatments is surgery, radiation therapy, and chemotherapy (e.g., 5-fluorouracil, levamisole, leucovorin or semustine (methyl CCNU)), N[2-(dimethylamino) ethyl]acridine-4-carboxamide and other related carboxamide anticancer drugs; non-topoisomerase II inhibitors, irinotecan, liposomal topotecan, taxane class of anticancer agents (e.g., paclitaxel or docetaxel), a compound of the xanthenone acetic acid class (e.g., 5,6-dimethylanthenone-4-acetic acid PMAA), laminarin, site-selective cyclic AMP Analogs (e.g., 8-chloroadenosine 3',5'-cyclic phosphate), pyranoindole inhibitors of Cox-2, carbazole inhibitors of Cox-2, tetrahydrocarbazole inhibitors of Cox-2, indene inhibitors of Cox-2, localized inhibitors of NSAIDS (e.g., anthranilic acids, aspirin (5-acetylsalicylic acid), azodisal sodium, carboheterocyclic acids, carprofen, chlorambucil, diclophenac, fenbufen, fenclofenac, fenoprofen, flufenamic acid, flurbiprofen, fluprofen, furosemide, gold sodium thiomalate, ibuprofen, indomethacin, indoprofen, ketoprofen, lonazolac, loxoprofen, meclofenamic acid, mefanamic acid, melphalan, naproxen, penicillamine, phenylacetic acids, proprionic acids, salicylic acids, salazosulfapyridine, sulindac, tolmetin, a pyrazolone butazone propazone NSAID, meloxicam, oxicams, piroxicam, feldene, piroxicam beta cyclodextran, tenoxicam, etodolac, and oxaprozin), an inhibitor of HER-2/neu, RNAi therapy, GM-CSF, monoclonal antibodies (e.g., anti-Her-2/neu antibodies, anti-CEA antibodies, A33 (HB 8779), 100-210 (HB 11764) and 100-310 (HB 11028)), bevacizumab (AVASTIN®), ranibizumab (LUCENTIS®), VEGF-Trap, sunitinib (SUTENT®), sorafenib (NEXAVAR®), axitinib, pegaptanib pazopanib, and erbitux), vectibix, hormonal therapy, pyrimidineamines, camptothecin derivatives (e.g., CPT-11), folinic acid (FA), Gemcitabine, Ara-C, platinum-based chemotherapeutics such as cisplatin, carboplatin and oxaliplatin, a cGMP-specific phosphodiesterase inhibitor, or any combination thereof. The dosages for any of these therapies are known in the art and can be adjusted with combination therapy accordingly.

Pancreatic Cancer

In one embodiment, the cancer is pancreatic cancer and the one or more therapeutic treatments is surgery, radiation therapy (RT), Fluorouracil (5-FU) and RT, systemic therapy, stenting, Gemcitabine (GEMZAR®), Gemcitabine and RT, Cetuximab, erlotinib (TARCEVA®), chemoradiation, bevacizumab (AVASTIN®), or any combination thereof. The dosages for any of these therapies are known in the art and can be adjusted with combination therapy accordingly.

Cervical Cancer

In one embodiment, the cancer is cervical cancer and the one or more anticancer treatments include, but are not limited to, surgery, immunotherapy, radiation therapy and chemotherapy. Some possible surgical options are cryosurgery, a hysterectomy, and a radical hysterectomy. Radiation therapy for cervical cancer patients includes external beam radiation therapy or brachytherapy. Anti-cancer drugs that may be administered as part of chemotherapy to treat cervical cancer include cisplatin, carboplatin, hydroxyurea, irinotecan, bleomycin, vincristine, mitomycin, ifosfamide, fluorouracil, etoposide, methotrexate, and combinations thereof.

Thyroid Cancer

In one embodiment, the cancer is thyroid cancer and the one or more anticancer treatments include, but are not limited to, surgery, immunotherapy, radiation therapy, hormone therapy and chemotherapy. Surgery is the most common treatment of thyroid cancer. Some possible surgical options for treatment of thyroid cancer are lobectomy, near-total thyroidectomy, total thyroidectomy and lymph node dissection. Radiation therapy may be external radiation therapy or may required intake of a liquid that contains radioactive iodine. Hormone therapy uses hormones to stop cancer cells from growing. In treating thyroid cancer, hormones can be used to stop the body from making other hormones that might make cancer cells grow.

EGFR Inhibitor Resistance and EGFR Inhibitors

Over-expression of the epidermal growth factor receptor (EGFR), or its ligand TGFα, is frequently associated with, for example, breast, lung and head and neck cancer, and is believed to contribute to the malignant growth of these tumors. The development of compounds that inhibit the kinase activity of the EGFR, as well as antibodies that block EGFR activation, for use as anti-tumor agents is an area of intense research effort.

Epidermal growth factor (EGF), acting through its receptor EGFR, is a mitogen and survival factor for epithelial cells (Rheinwald, J. G. and Green, H., 1977, Nature 265, 421; Rodeck, U. et al., 1997, J. Cell Science 110, 113). Thus, there is the potential that use of EGFR inhibitors in chemotherapy would interfere with the normal renewal of skin and other epithelial tissues such as the cornea and the lining of the gastrointestinal tract: Toxicity to proliferating tissues such as skin and the G1 tract is frequently a dose-limiting side effect of cytotoxic agents. Such toxicity may be manifested, among other symptoms, as a skin rash, diarrhea, corneal thinning, hair atrophy or loss, hair follicle dysplasia, degeneration, necrosis or inflammation, interfollicular epidermal hyperplasia, or a failure to heal or a delayed healing after injury.

As used herein, the term "EGFR inhibitor" refers to any EGFR inhibitor that is currently known in the art or that will be identified in the future, and includes any entity that, upon administration to a patient, results in inhibition of a biological activity associated with activation of the EGFRs in the patient, including any of the downstream biological effects otherwise resulting from the binding to an EGFR of its natural ligand. Such EGFR inhibitors include any agent that can block EGFR activation or any of the downstream biological effects of EGFR activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the EGFR receptor or a portion thereof, thereby making the receptor inaccessible to its natural ligand so that its normal biological activity is prevented or reduced. EGFR inhibitors include but are not limited to low molecular weight inhibitors, antibodies or antibody fragments, antisense constructs and ribozymes. In a preferred embodiment, the EGFR inhibitor is a small organic molecule or an antibody that binds specifically to the human EGFR.

EGFR inhibitors that can be used according to the present methods include, but are not limited to, those classified in the art as quinazoline EGFR inhibitors, pyrido-pyrimidine EGFR inhibitors, pyrimido-pyrimidine EGFR inhibitors, pyrrolo-pyrimidine EGFR inhibitors, pyrazolo-pyrimidine EGFR inhibitors, phenylamino-pyrimidine EGFR inhibitors, oxindole EGFR inhibitors, indolocarbazole EGFR inhibitors, phthalazine EGFR inhibitors, isoflavone EGFR inhibitors, quinalone EGFR inhibitors, and tyrphostin EGFR inhibitors.

Non-limiting examples of low molecular weight EGFR inhibitors useful in practicing the present methods include any of the EGFR inhibitors described in the following patent publications, and all pharmaceutically acceptable salts and solvates of said EGFR inhibitors: European Patent Application EP 520722, published Dec. 30, 1992; European Patent Application EP 566226, published Oct. 20, 1993; PCT International Publication WO 96/33980, published Oct. 31, 1996; U.S. Pat. No. 5,747,498, issued May 5, 1998; PCT International Publication WO 96/30347, published Oct. 3, 1996; European Patent Application EP 787772, published Aug. 6, 1997; PCT International Publication WO 97/30034, published Aug. 21, 1997; PCT International Publication WO 97/30044, published Aug. 21, 1997; PCT International Publication WO 97/38994, published Oct. 23, 1997; PCT International Publication WO 97/49688, published Dec. 31, 1997; European Patent Application EP 837063, published Apr. 22, 1998; PCT International Publication WO 98/02434, published Jan. 22, 1998; PCT International Publication WO 97/38983, published Oct. 23, 1997; PCT International Publication WO 95/19774, published Jul. 27, 1995; PCT International Publication WO 95/19970, published Jul. 27, 1995; PCT International Publication WO 97/13771, published Apr. 17, 1997; PCT International Publication WO 98/02437, published Jan. 22, 1998; PCT International Publication WO 98/02438, published Jan. 22, 1998; PCT International Publication WO 97/32881, published Sep. 12, 1997; German Application DE 19629652, published Jan. 29, 1998; PCT International Publication WO 98/33798, published Aug. 6, 1998; PCT International Publication WO 97/32880, published Sep. 12, 1997; PCT International Publication WO 97/32880 published Sep. 12, 1997; European Patent Application EP 682027, published Nov. 15, 1995; PCT International Publication WO 97/02266, published January 23, 197; PCT International Publication WO 97/27199, published Jul. 31, 1997; PCT International Publication WO 98/07726, published Feb. 26, 1998; PCT International Publication WO 97/34895, published Sep. 25, 1997; PCT International Publication WO 96/31510, published Oct. 10, 1996; PCT International Publication WO 98/14449, published Apr. 9, 1998; PCT International Publication WO 98/14450, published Apr. 9, 1998; PCT International Publication WO 98/14451, published Apr. 9, 1998; PCT International Publication WO 95/09847, published Apr. 13, 1995; PCT International Publication WO 97/19065, published May 29, 1997; PCT International Publication WO 98/17662, published Apr. 30, 1998; U.S. Pat. No. 5,789,427, issued Aug. 4, 1998; U.S. Pat. No. 5,650,415, issued Jul. 22, 1997; U.S. Pat. No. 5,656,643, issued Aug. 12, 1997; PCT International Publication WO 99/35146, published Jul. 15, 1999; PCT International Publication WO 99/35132, published Jul. 15, 1999; PCT International Publication WO 99/07701, published Feb. 18, 1999; and PCT International Publication WO 92/20642 published Nov. 26, 1992. Additional non-limiting examples of low molecular weight EGFR inhibitors include any of the EGFR inhibitors described in Traxler, P., 1998, Exp. Opin. Ther. Patents 8(12):1599-1625.

Specific preferred examples of low molecular weight EGFR inhibitors that can be used according to the present methods include [6,7-bis(2-methoxyethoxy)-4-quinazolin-4-yl]-(3-ethynylphenyl)amine (U.S. Pat. No. 5,747,498 issued May 5, 1998 and Moyer et al., 1997, supra); CI-1033 and PD183805 (Sherwood et al., 1999, Proc. Am. Assoc. Cancer Res. 40:723); and ZD1839 (Woodburn et al., 1997, Proc. Am. Assoc. Cancer Res. 38:633).

Antibody-based EGFR inhibitors include any anti-EGFR antibody or antigen-binding fragment thereof that can partially or completely block EGFR activation by its natural ligand. Non-limiting examples of antibody-based EGFR inhibitors include those described in Modjtahedi, H., et al., 1993, Br. J. Cancer 67:247-253; Teramoto, T., et al., 1996, Cancer 77:639-645; Goldstein et al., 1995, Clin. Cancer Res. 1:1311-1318; Huang, S. M., et al., 1999, Cancer Res. 15:59 (8):1935-40; and Yang, X., et al., 1999, Cancer Res. 59:1236-1243. Thus, the EGFR inhibitor can be monoclonal antibody Mab E7.6.3 (Yang, 1999 supra), or Mab C225 (ATCC Accession No. HB-8508), or an antibody or antigen-binding fragment thereof having the binding specificity thereof. Other examples of antibody-based EGFR inhibitors include, for example, TARCEVA® (Erlotinib), ERBITUX® (Cetuximab), and Iressa® (Gefitinib).

Additional antibody-based EGFR inhibitors can be raised according to known methods by administering the appropriate antigen or epitope to a host animal selected, e.g., from pigs, cows, horses, rabbits, goats, sheep, and mice, among others. Various adjuvants known in the art can be used to enhance antibody production (such as, for example, aluminum hydroxide, complete Freund's adjuvant, incomplete Freund's adjuvant, etc.).

Although antibodies useful in practicing the methods include, but are not limited to, polyclonal, monoclonal, humanized, chimeric, human, and genetically-engineered antibodies.

The terms "antigen-binding portion of an antibody," "antigen-binding fragment," "antigen-binding domain," "antibody fragment" or a "functional fragment of an antibody" are used interchangeably herein to refer to one or more fragments of an antibody that retain the ability to specifically bind to an antigen. Non-limiting examples of antibody fragments included within such terms include, but are not limited to, a Fab fragment, a F(ab')$_2$ fragment, a Fd fragment consisting of the VH and CH1 domains, a Fv fragment, a scFv, a scFv2 (a tandem linkage of two scFv molecules head to tail in a chain), a dAb fragment (Ward et al., (1989) Nature 341:544 546); an isolated CDR, an AVIMER™, a VH, a VL, and a single chain binding polypeptide (a scFv fused to an immunoglobulin Fc). Additionally included in this definition are "one-half" antibodies comprising a single heavy chain and a single light chain. Other forms of single chain antibodies, such as diabodies are also encompassed herein.

"F(ab')$_2$" and "Fab'" moieties can be produced by treating an Ig with a protease such as pepsin and papain, and include antibody fragments generated by digesting immunoglobulin near the disulfide bonds existing between the hinge regions in each of the two heavy chains. For example, papain cleaves IgG upstream of the disulfide bonds existing between the hinge regions in each of the two heavy chains to generate two homologous antibody fragments in which an light chain composed of VL and CL (light chain constant region), and a heavy chain fragment composed of VH and CHγ1 (γ1 region in the constant region of the heavy chain) are connected at their C terminal regions through a disulfide bond. Each of these two homologous antibody fragments is called Fab'. Pepsin also cleaves IgG downstream of the disulfide bonds existing between the hinge regions in each of the two heavy chains to generate an antibody fragment slightly larger than the fragment in which the two above-mentioned Fab' are connected at the hinge region. This antibody fragment is called a F(ab')$_2$.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Fv" refers to an antibody fragment which contains a complete antigen-recognition and antigen-binding site. This region consists of a dimer of one heavy chain and one light chain variable domain in tight, non-covalent association. It is in this configuration that the three CDRs of each variable domain interact to define an antigen-binding site on the surface of the VH-VL dimer. Collectively, a combination of one or more of the CDRs from each of the VH and VL chains confer antigen-binding specificity to the antibody. For example, it would be understood that, for example, the CDRH3 and CDRL3 could be sufficient to confer antigen-binding specificity to an antibody when transferred to VH and VL chains of a recipient antibody or antigen-binding fragment thereof and this combination of CDRs can be tested for binding, affinity, etc. using any of the techniques described herein. Even a single variable domain (or half of an Fv comprising only three CDRs specific for an antigen) has the ability to recognize and bind antigen, although likely at a lower affinity than when combined with a second variable domain. Furthermore, although the two domains of a Fv fragment (VL and VH), are coded for by separate genes, they can be joined using recombinant methods by a synthetic linker that enables them to be made as a single protein chain in which the VL and VH regions pair to form monovalent molecules (known as single chain Fv (scFv); Bird et al. Science 242:423-426 (1988); Huston et al. Proc. Natl. Acad. Sci. USA 85:5879-5883 (1988); and Osbourn et al. Nat. Biotechnol. 16:778 (1998)). Such scFvs are also intended to be encompassed within the term "antigen-binding portion" of an antibody. Any VH and VL sequences of specific scFv can be linked to an Fc region cDNA or genomic sequences, in order to generate expression vectors encoding complete Ig (e.g., IgG) molecules or other isotypes. VH and VL can also be used in the generation of Fab, Fv or other fragments of Igs using either protein chemistry or recombinant DNA technology.

"Single-chain Fv" or "sFv" antibody fragments comprise the VH and VL domains of an antibody, wherein these domains are present in a single polypeptide chain. In some embodiments, the Fv polypeptide further comprises a polypeptide linker between the VH and VL domains which enables the sFv to form the desired structure for antigen binding. For a review of sFvs see, e.g., Pluckthun in The Pharmacology of Monoclonal Antibodies, Vol. 113, Rosenburg and Moore eds. Springer-Verlag, New York, pp. 269-315 (1994).

The term "Avimer™" refers to a class of therapeutic proteins of human origin, which are unrelated to antibodies and antibody fragments, and are composed of several modular and reusable binding domains, referred to as A-domains (also referred to as class A module, complement type repeat, or LDL-receptor class A domain). They were developed from human extracellular receptor domains by in vitro exon shuffling and phage display (Silverman et al., 2005, Nat. Biotechnol. 23:1493-1494; Silverman et al., 2006, Nat. Biotechnol. 24:220). The resulting proteins can contain multiple independent binding domains that can exhibit improved affinity (in some cases, sub-nanomolar) and specificity compared with single-epitope binding proteins. See, for example, U.S. Patent Application Publ. Nos. 2005/0221384, 2005/0164301, 2005/0053973 and 2005/0089932, 2005/0048512, and 2004/0175756, each of which is hereby incorporated by reference herein in its entirety.

Each of the known 217 human A-domains comprises ~35 amino acids (~4 kDa); and domains are separated by linkers that average five amino acids in length. Native A-domains fold quickly and efficiently to a uniform, stable structure mediated primarily by calcium binding and disulfide formation. A conserved scaffold motif of only 12 amino acids is required for this common structure. The end result is a single protein chain containing multiple domains, each of which represents a separate function. Each domain of the proteins binds independently and the energetic contributions of each domain are additive. These proteins were called "Avimers™" from avidity multimers.

The term "diabodies" refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA 90:6444 6448 (1993).

Antigen-binding polypeptides also include heavy chain dimers such as, for example, antibodies from camelids and sharks. Camelid and shark antibodies comprise a homodimeric pair of two chains of V-like and C-like domains (neither has a light chain). Since the VH region of a heavy chain dimer IgG in a camelid does not have to make hydrophobic interactions with a light chain, the region in the heavy chain that normally contacts a light chain is changed to hydrophilic amino acid residues in a camelid. VH domains of heavy-chain dimer IgGs are called VHH domains. Shark Ig-NARs comprise a homodimer of one variable domain (termed a V-NAR domain) and five C-like constant domains (C-NAR domains). In camelids, the diversity of antibody repertoire is determined by the CDRs 1, 2, and 3 in the VH or VHH regions. The CDR3 in the camel VHH region is characterized by its relatively long length, averaging 16 amino acids (Muyldermans et al., 1994, Protein Engineering 7(9): 1129). This is in contrast to CDR3 regions of antibodies of many other species. For example, the CDR3 of mouse VH has an average of 9 amino acids. Libraries of camelid-derived antibody variable regions, which maintain the in vivo diversity of the variable regions of a camelid, can be made by, for example, the methods disclosed in U.S. Patent Application Ser. No. 20050037421.

"Humanized" forms of non-human (e.g., murine) antibodies include chimeric antibodies which contain minimal sequence derived from a non-human Ig. For the most part, humanized antibodies are human Igs (recipient antibody) in which one or more of the CDRs of the recipient are replaced by CDRs from a non-human species antibody (donor antibody) such as mouse, rat, rabbit or non-human primate having the desired specificity, affinity and binding function. In some instances, one or more FR amino acid residues of the human Ig are replaced by corresponding non-human amino acid residues. Furthermore, humanized antibodies can contain residues which are not found in the recipient antibody or in the donor antibody. These modifications can be made to refine antibody performance, if needed. A humanized antibody can comprise substantially all of at least one and, in some cases two, variable domains, in which all or substantially all of the hypervariable regions correspond to those of a non-human immunoglobulin and all, or substantially all, of the FRs are those of a human immunoglobulin sequence. The humanized antibody optionally can also include at least a portion of an immunoglobulin constant region (Fc), typically that of a human immunoglobulin. For details, see Jones et al., Nature 321: 522-525 (1986); Reichmann et al., Nature 332: 323-329 (1988); and Presta, Curr. Op. Struct. Biol. 2: 593-596 (1992).

Monoclonal antibodies against EGFR can be prepared and isolated using any technique that provides for the production of antibody molecules by continuous cell lines in culture. Techniques for production and isolation include but are not limited to the hybridoma technique originally described by Kohler and Milstein (Nature, 1975, 256: 495-497); the human B-cell hybridoma technique (Kosbor et al., 1983, Immunology Today 4:72; Cote et al., 1983, Proc. Natl. Acad. Sci. USA 80: 2026-2030); and the EBV-hybridoma technique (Cole et al, 1985, Monoclonal Antibodies and Cancer Therapy, Alan R. Liss, Inc., pp. 77-96).

Alternatively, techniques described for the production of single chain antibodies (see, e.g., U.S. Pat. No. 4,946,778) can be adapted to produce anti-EGFR single chain antibodies. Antibody-based EGFR inhibitors useful in practicing the present methods also include anti-EGFR antibody fragments including but not limited to F(ab')$_2$ fragments, which can be generated by pepsin digestion of an intact antibody molecule, and Fab fragments, which can be generated by reducing the disulfide bridges of the F(ab')$_2$ fragments. Alternatively, Fab and/or scFv expression libraries can be constructed (see, e.g., Huse et al., 1989, Science 246: 1275-1281) to allow rapid identification of fragments having the desired specificity to EGFR.

Techniques for the production and isolation of monoclonal antibodies and antibody fragments are well-known in the art, and are additionally described, among other places, in Harlow and Lane, 1988, Antibodies: A Laboratory Manual, Cold Spring Harbor Laboratory, and in J. W. Goding, 1986, Monoclonal Anti-bodies: Principles and Practice, Academic Press, London. Humanized anti-EGFR antibodies and antibody fragments can also be prepared according to known techniques such as those described in Vaughn, T. J. et al., 1998, Nature Biotech. 16:535-539 and references cited therein, and such antibodies or fragments thereof are also useful in practicing the present methods.

Small inhibitory RNAs (siRNAs) can also function as EGFR inhibitors for use in the present methods. EGFR gene expression can be reduced by contacting the tumor, subject or cell with a small double stranded RNA (dsRNA), or a vector or construct causing the production of a small double stranded RNA, such that expression of EGFR is specifically inhibited (i.e., RNA interference or RNAi). Methods for selecting an appropriate dsRNA or dsRNA-encoding vector are well known in the art for genes whose sequence is known (e.g., see Tuschi, T., et al. (1999) Genes Dev. 13(24):3191-3197; Elbashir, S. M. et al. (2001) Nature 411:494-498; Hannon, G. J. (2002) Nature 418:244-251; McManus, M. T. and Sharp, P. A. (2002) Nature Reviews Genetics 3:737-747; Bremmelkamp, T. R. et al. (2002) Science 296:550-553; U.S. Pat. Nos. 6,573,099 and 6,506,559; and International Patent Publication Nos. WO 01/36646, WO 99/32619, and WO 01/68836).

Ribozymes can also function as EGFR inhibitors for use in the present methods. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of EGFR mRNA sequences are thereby useful within the scope of the present methods. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Various modifications to the oligonucleotides of the methods can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

The antisense oligonucleotide constructs, siRNA, and ribozymes suitable for use with the present methods may be synthesized by a variety of known methods or future-developed methods. For example, one may use methods of chemical synthesis such as methods that employ Dharmacon, Inc.'s proprietary ACE® technology. Alternatively, one could also use template dependant synthesis methods. Synthesis may be carried out using modified or non-modified, natural or non-natural bases as disclosed herein. Moreover, syntheses may be carried out with or without modified or non-modified nucleic acid backbone as disclosed herein.

In addition, the antisense oligonucleotide constructs, siRNA, and ribozymes may be synthesized in a host cell by a variety of known, and any future-developed method, for synthesizing antisense oligonucleotide constructs, siRNA, and ribozymes molecules in a host cell. For example, antisense oligonucleotide constructs, siRNA, and ribozymes can be expressed from recombinant circular or linear DNA vector using any suitable promoter. Suitable promoters for expressing antisense or inhibitory RNA molecules from a vector suitable for use with the methods include, for example, the U6 or H1 RNA pol III promoter sequences and the cytomegalovirus promoter. Selection of other suitable promoters is within the skill in the art. Suitable vectors for use with the subject methods include those described in U.S. Pat. No. 5,624,803, the disclosure of which is incorporated herein in its entirely. The recombinant plasmids of the embodiments can also comprise inducible or regulatable promoters for expression of the antisense oligonucleotide constructs, siRNA, and ribozymes in a particular tissue or in a particular intracellular environment.

The antisense oligonucleotide constructs, siRNA, and ribozymes of the embodiments described herein can be expressed from a recombinant nucleic acid vector either as two separate, complementary RNA molecules, or as a single RNA molecule with two complementary regions. Selection of vectors suitable for expressing antisense oligonucleotide constructs, siRNA, and ribozymes, methods for inserting nucleic acid sequences for expressing antisense oligonucleotide constructs, siRNA, and ribozymes into the vector, and methods of delivering the recombinant vector to the cells of interest are within the skill in the art. See, for example, Tuschl, T. (2002), Nat. Biotechnol, 20: 446-448; Brummelkamp T R et al. (2002), Science 296: 550-553; Miyagishi M et al. (2002), Nat. Biotechnol. 20: 497-500; Paddison P J et al. (2002), Genes Dev. 16: 948-958; Lee N S et al. (2002), Nat. Biotechnol. 20: 500-505; and Paul C P et al. (2002), Nat. Biotechnol. 20: 505-508, the entire disclosures of which are herein incorporated by reference. Other methods for delivery and intracellular expression are described in, for example, U.S. Patent Application Publication Nos. 20040005593, 20050048647, 20050060771, the entire disclosures of which are herein incorporated by reference.

In one embodiment, following contacting cells with a catecholic butane, EGFR inhibitors can inhibit the activity of EGFR by at least about 2-fold, at least about 5 fold, at least about 10 fold, at least about 20 fold, at least about 25 fold, at least about 50 fold, at least about 100 fold or more. In another embodiment, inhibitors can inhibit the activity of EGFR by at least about 5%, at least about 10%, at least about 15%, at least about 20%, at least about 50%, at least about 60%, at least about 70%, at least about 80%, at least about 90%, at least about 95% or at least about 100%. In another embodiment, inhibition of EGFR results in stasis of symptoms of a patient that has received administration of a combination of a catecholic butane and an EGFR inhibitor.

IGF-JR Inhibitor Resistance and Inhibitors

IGF-1R (type 1 insulin-like growth factor receptor) is a transmembrane RTK that binds primarily to IGF-1 but also to IGF-II and insulin with lower affinity. Binding of IGF-1 to its receptor results in multiple cellular effects including receptor oligomerization, activation of tyrosine kinases, intermolecular receptor autophosphorylation, and phosphorylation of cellular substrates such as IRS1 and Shc. The ligand-activated IGF-1R also induces mitogenic activity in normal cells and plays an important role in abnormal growth. A major physiological role of the IGF-1 system is the promotion of normal growth and regeneration. Overexpression of IGF-1R can initiate mitogenesis and promote ligand-dependent neoplastic transformation. Furthermore, IGF-1R is involved in the establishment and maintenance of the malignant phenotype. Several oncogenes have been demonstrated to affect IGF-1 and IGF-1R expression, and a reduction of IGF-1R expression correlates with a resistance to transformation. Exposure of cells to the mRNA antisense to IGF-1R RNA prevents soft agar growth of several human tumor cell lines. IGF-1R abrogates progression into apoptosis, both in vivo and in vitro, and a decrease in the level of IGF-1R below wild-type levels causes apoptosis of tumor cells in vivo.

IGF-1R overexpression is frequently found in various tumors (breast, colon, lung, sarcoma) and is often associated with an aggressive phenotype. High circulating IGF1 concentrations are also correlated with prostate, lung and breast cancer risk. Furthermore, IGF-1R is implicated with establishment and maintenance of the transformed phenotype in vitro and in vivo (Baserga R. Exp. Cell. Res., 1999, 253, 1-6). The kinase activity of IGF-1R participates in the transforming activity of several oncogenes such as EGFR, PDGFR, SV40 T antigen, activated Ras, Raf, and v-Src. The expression of IGF-1R in normal fibroblasts induces neoplastic phenotypes, which can then form tumors in vivo. IGF-1R expression plays an important role in anchorage-independent growth. IGF-1R has also been shown to protect cells from chemotherapy-, radiation-, and cytokine-induced apoptosis. Conversely, inhibition of endogenous IGF-1R by a dominant negative IGF-1R, triple helix formation, or antisense expression vector has been shown to repress transforming activity in vitro and tumor growth in animal models. Like resistance to EGFR inhibitors, tumors/cancers can similarly develop resistance to IGF-1R inhibitors.

In one embodiment, the present methods relate to use of IGF-1R inhibiting compounds.

As used herein, the term "IGF-1R inhibitor" refers to any number of IGF-1R inhibitors, such as any chemical entity (e.g., small molecule) or biologic (e.g., antibodies, binding proteins, oligonucleotides, etc.), that upon administration to a patient, results in inhibition of a biological activity associated with activation of the IGF-1 receptor in the patient, including any of the downstream biological effects otherwise resulting from the binding to IGF-1R of its natural ligand. IGF-1R kinase inhibitors include agents that can block IGF-1R activation or any of the downstream biological effects of IGF-1R activation that are relevant to treating cancer in a patient. Exemplary modes of action by such inhibitors include, but are not limited to, binding directly to the intracellular domain of the receptor and inhibiting its kinase activity. Alternatively, IGF-1R inhibitors can act by occupying the ligand binding site or a portion thereof of the IGF-1 receptor, thereby making the receptor inaccessible to its natural ligand so that its normal biological activity is prevented or reduced. Alternatively, IGF-1R inhibitors can act by modulating the dimerization of IGF-1R polypeptides, or interaction of IGF-1R polypeptide with other proteins, or enhance ubiquitination and endocytotic degradation of IGF-1R. An IGF-1R inhibitor can also act by reducing the amount of IGF-1 available to activate IGF-1R by, for example, antagonizing the binding of IGF-1 to its receptor, by reducing the level of IGF-1, or by promoting the association of IGF-1 with proteins other than IGF-1R such as IGF binding proteins (e.g., IGFBP3). IGF-1R inhibitors include but are not limited to low molecular weight inhibitors, antibodies or antibody fragments, antisense constructs, small inhibitory RNAs (e.g., RNA interference by dsRNA; RNAi), and ribozymes. In one embodiment, the IGF-1R inhibitor is a small organic molecule or a monoclonal antibody that binds specifically to human IGF-1R.

In one embodiment, an IGF-1R inhibitor is a small organic molecule. Exemplary IGF-1R inhibitors include, but are not limited to, imidazopyrazine IGF-1R kinase inhibitors, quinazoline IGF-1R kinase inhibitors, pyrido-pyrimidine IGF-1R kinase inhibitors, pyrimido-pyrimidine IGF-1R kinase inhibitors, pyrrolo-pyrimidine IGF-1R kinase inhibitors, pyrazolo-pyrimidine IGF-1R kinase inhibitors, phenylamino-pyrimidine IGF-1R kinase inhibitors, oxindole IGF-1R kinase inhibitors, indolocarbazole IGF-1R kinase inhibitors, phthalazine IGF-1R kinase inhibitors, isoflavone IGF-1R kinase inhibitors, quinalone IGF-1R kinase inhibitors, and tyrphostin IGF-1R kinase inhibitors, and all pharmaceutically acceptable salts and solvates of such IGF-1R kinase inhibitors.

Additional examples of IGF-1R inhibitors include those in International Patent Publication No. WO 05/037836, (imidazopyrazine IGF-1R kinase inhibitors), International Patent Publication Nos. WO 03/018021 and WO 03/018022, (pyrimidines and pyrimidine based compounds), International Patent Publication Nos. WO 02/102804 and WO 02/102805, (cyclolignans), International Patent Publication No. WO 02/092599, (pyrrolopyrimidines), International Patent Publication No. WO 01/72751, (pyrrolopyrimidines), and in International Patent Publication No. WO 00/71129, (pyrrolotriazine inhibitors), and in International Patent Publication No. WO 97/28161, (pyrrolo[2,3-d]pyrimidines), Parrizas, et al., (tyrphostins with in vitro and in vivo IGF-1R inhibitory activity (Endocrinology, 138:1427-1433 (1997)), International Patent Publication No. WO 00/35455, (heteroaryl-aryl ureas), International Patent Publication No. WO 03/048133, (pyrimidine derivatives), International Patent Publication No. WO 03/024967, WO 03/035614, WO 03/035615, WO 03/035616, and WO 03/035619, (chemical compounds with inhibitory effects towards kinase proteins), International Patent Publication No. WO 03/068265, (compositions for treating hyperproliferative conditions), International Patent Publication No. WO 00/17203, (pyrrolopyrimidines), Japanese Patent Publication No. JP 07/133,280, (cephem compound), and Albert, A. et al., Journal of the Chemical Society, 11: 1540-1547 (1970), (pteridines and pteridines unsubstituted in the 4-position).

Other exemplary small molecule inhibitor include, but are not limited to, OSI-906 (OSI) and XL228 (Exelixis). In one aspect, an IGF-1R inhibitor can be a small molecule inhibitor. Exemplary small molecule inhibitors include, but are not limited to, OSI-906 (OSI) and XL228 (Exelixis).

OSI-906 (OSI) can be administered in different dosing and administration schedules such as, for example: (1) once or twice daily orally at increasing doses until disease progression or unacceptable toxicity (up to 21 days); and (2) treatment opens with 51 (QD days 1-3 every 14 days), with initiation of S2 (QD days 1-5 every 14 days) occurring upon observation of clinically significant related toxicity >=grade 2 in S1. Likewise, initiation of S3 (QD days 1-7 every 14 days) occurs upon observation of clinically significant related toxicity >=grade 2 in S2. In each schedule, a single dose will be administered on each of the specified days followed by a drug-free period through day 14.

XL228 (Exelixis) can be administered in different dosing and administration schedules such as, for example: IV weekly over 1 hour.

Additional specific examples of IGF-1R inhibitors that can be used according to the present methods include h7C10 (Centre de Recherche Pierre Fabre), an IGF-1 antagonist; EM-164 (ImmunoGen Inc.), an IGF-1R modulator; CP-751871 (Pfizer Inc.), an IGF-1 antagonist; lanreotide (Ipsen), an IGF-1 antagonist; IGF-1R oligonucleotides (Lynx Therapeutics Inc.); IGF-1 oligonucleotides (National Cancer Institute); IGF-1R protein-tyrosine kinase inhibitors in development by Novartis (e.g., NVP-AEW541, Garcia-Echeverria, C. et al. (2004) Cancer Cell 5:231-239; or NVP-ADW742, Mitsiades, C. S. et al. (2004) Cancer Cell 5:221-230); IGF-1R protein-tyrosine kinase inhibitors (Ontogen Corp); AG-1024 (Camirand, A. et al. (2005) Breast Cancer Research 7:R570-R579 (DOI 10.1186/bcr1028); Camirand, A. and Pollak, M. (2004) Brit. J. Cancer 90:1825-1829; Pfizer Inc.), an IGF-1 antagonist; the tyrphostins AG-538 and 1-OMe-AG 538; BMS-536924, a small molecule inhibitor of IGF-1R; and PNU-145156E (Pharmacia & Upjohn SpA), an IGF-1 antagonist.

Antibody-based IGF-1R inhibitors include any anti-IGF-1R antibody or antigen-binding fragment thereof that can partially or completely block IGF-1R activation by its natural ligand. Antibody-based IGF-1R inhibitors also include any anti-IGF-1 antibody or antibody fragment that can partially or completely block IGF-1R activation. Non-limiting examples of antibody-based IGF-1R inhibitors include those described in Larsson, O. et al (2005) Brit. J. Cancer 92:2097-2101 and Ibrahim, Y. H. and Yee, D. (2005) Clin. Cancer Res. 11; 944s-950s; the monoclonal antibody IMC-A12 developed and tested by the National Cancer Institute; commercially developed antibodies including antibodies from Imclone (e.g., A12), Amgen (AMG479), or Schering-Plough Research Institute (e.g., 19D12); and antibodies described in US Patent Application Publication Nos. US 2005/0136063 A1 and US 2004/0018191 A1). The IGF-1R inhibitor can be a monoclonal antibody, polyclonal antibody, or an antibody or antibody fragment having the binding specificity thereof. Exemplary monoclonal antibodies include, but are not limited to, AMG-479 (Amgen), BIIB022 (Biogen), IMC-A12 (ImClone), CP-751,871 (Pfizer), SCH-717454 (Schering), R-1507 (Roche) and MK-0646 (Merck).

The terms "antigen-binding portion of an antibody," "antigen-binding fragment," "antigen-binding domain," "antibody fragment" or a "functional fragment of an antibody" are used interchangeably herein to refer to one or more fragments of an antibody that retain the ability to specifically bind to an antigen. Non-limiting examples of antibody fragments included within such terms include, but are not limited to, a Fab fragment, a F(ab')$_2$ fragment, a Fd fragment consisting of the VH and CH1 domains, a Fv fragment, a scFv, a scFv2 (a tandem linkage of two scFv molecules head to tail in a chain), a dAb fragment (Ward et al., (1989) Nature 341:544 546); an isolated CDR, an AVIMER™, a VH, a VL, and a single chain binding polypeptide (a scFv fused to an immunoglobulin Fc). Additionally included in this definition are "one-half" antibodies comprising a single heavy chain and a single light chain. Other forms of single chain antibodies, such as diabodies are also encompassed herein.

"F(ab')$_2$" and "Fab'" moieties can be produced by treating an Ig with a protease such as pepsin and papain, and include antibody fragments generated by digesting immunoglobulin near the disulfide bonds existing between the hinge regions in each of the two heavy chains. For example, papain cleaves IgG upstream of the disulfide bonds existing between the hinge regions in each of the two heavy chains to generate two homologous antibody fragments in which an light chain composed of VL and CL (light chain constant region), and a heavy chain fragment composed of VH and CHγ1 (γ1 region in the constant region of the heavy chain) are connected at their C terminal regions through a disulfide bond. Each of these two homologous antibody fragments is called Fab'. Pepsin also cleaves IgG downstream of the disulfide bonds existing between the hinge regions in each of the two heavy chains to generate an antibody fragment slightly larger than the fragment in which the two above-mentioned Fab' are connected at the hinge region. This antibody fragment is called F(ab')$_2$.

The Fab fragment also contains the constant domain of the light chain and the first constant domain ($CH_1$) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Fv" refers to an antibody fragment which contains a complete antigen-recognition and antigen-binding site. This region consists of a dimer of one heavy chain and one light chain variable domain in tight, non-covalent association. It is in this configuration that the three CDRs of each variable domain interact to define an antigen-binding site on the surface of the VH-VL dimer. Collectively, a combination of one or more of the CDRs from each of the VH and VL chains confer antigen-binding specificity to the antibody. For example, it would be understood that, for example, the CDRH3 and CDRL3 could be sufficient to confer antigen-binding specificity to an antibody when transferred to VH and VL chains of a recipient antibody or antigen-binding fragment thereof and this combination of CDRs can be tested for binding, affinity, etc. using any of the techniques described herein. Even a single variable domain (or half of an Fv comprising only three CDRs specific for an antigen) has the ability to recognize and bind antigen, although likely at a lower affinity than when combined with a second variable domain. Furthermore, although the two domains of a Fv fragment (VL and VH), are coded for by separate genes, they can be joined using recombinant methods by a synthetic linker that enables them to be made as a single protein chain in which the VL and VH regions pair to form monovalent molecules (known as single chain Fv (scFv); Bird et al. Science 242:423-426 (1988); Huston et al. Proc. Natl. Acad. Sci. USA 85:5879-5883 (1988); and Osbourn et al. Nat. Biotechnol. 16:778 (1998)). Such scFvs are also intended to be encompassed within the term "antigen-binding portion" of an antibody. Any VH and VL sequences of specific scFv can be linked to an Fc region cDNA or genomic sequences, in order to generate expression vectors encoding complete Ig (e.g., IgG) molecules or other isotypes. VH and VL can also be used in the generation of Fab, Fv or other fragments of Igs using either protein chemistry or recombinant DNA technology.

"Single-chain Fv" or "sFv" antibody fragments comprise the VH and VL domains of an antibody, wherein these domains are present in a single polypeptide chain. In some embodiments, the Fv polypeptide further comprises a polypeptide linker between the VH and VL domains which enables the sFv to form the desired structure for antigen binding. For a review of sFvs see, e.g., Pluckthun in The Pharmacology of Monoclonal Antibodies, Vol. 113, Rosenburg and Moore eds. Springer-Verlag, New York, pp. 269-315 (1994).

The term "Avimer™" refers to a class of therapeutic proteins of human origin, which are unrelated to antibodies and antibody fragments, and are composed of several modular and reusable binding domains, referred to as A-domains (also referred to as class A module, complement type repeat, or LDL-receptor class A domain). They were developed from human extracellular receptor domains by in vitro exon shuffling and phage display (Silverman et al., 2005, Nat. Biotechnol. 23:1493-1494; Silverman et al., 2006, Nat. Biotechnol. 24:220). The resulting proteins can contain multiple independent binding domains that can exhibit improved affinity (in some cases, sub-nanomolar) and specificity compared with single-epitope binding proteins. See, for example, U.S. Patent Application Publ. Nos. 2005/0221384, 2005/0164301, 2005/0053973 and 2005/0089932, 2005/0048512, and 2004/0175756, each of which is hereby incorporated by reference herein in its entirety.

Each of the known 217 human A-domains comprises ~35 amino acids (~4 kDa); and domains are separated by linkers that average five amino acids in length. Native A-domains fold quickly and efficiently to a uniform, stable structure mediated primarily by calcium binding and disulfide formation. A conserved scaffold motif of only 12 amino acids is required for this common structure. The end result is a single protein chain containing multiple domains, each of which represents a separate function. Each domain of the proteins binds independently and the energetic contributions of each domain are additive. These proteins were called "Avimers™" from avidity multimers.

The term "diabodies" refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA 90:6444 6448 (1993).

Antigen-binding polypeptides also include heavy chain dimers such as, for example, antibodies from camelids and sharks. Camelid and shark antibodies comprise a homodimeric pair of two chains of V-like and C-like domains (neither has a light chain). Since the VH region of a heavy chain dimer IgG in a camelid does not have to make hydrophobic interactions with a light chain, the region in the heavy chain that normally contacts a light chain is changed to hydrophilic amino acid residues in a camelid. VH domains of heavy-chain dimer IgGs are called VHH domains. Shark Ig-NARs comprise a homodimer of one variable domain (termed a V-NAR domain) and five C-like constant domains (C-NAR domains). In camelids, the diversity of antibody repertoire is determined by the CDRs 1, 2, and 3 in the VH or VHH regions. The CDR3 in the camel VHH region is characterized by its relatively long length, averaging 16 amino acids (Muyldermans et al., 1994, Protein Engineering 7(9): 1129). This is in contrast to CDR3 regions of antibodies of many other species. For example, the CDR3 of mouse VH has an average of 9 amino acids. Libraries of camelid-derived antibody variable regions, which maintain the in vivo diversity of the variable regions of a camelid, can be made by, for example, the methods disclosed in U.S. Patent Application Ser. No. 20050037421.

"Humanized" forms of non-human (e.g., murine) antibodies include chimeric antibodies which contain minimal sequence derived from a non-human Ig. For the most part, humanized antibodies are human Igs (recipient antibody) in which one or more of the CDRs of the recipient are replaced by CDRs from a non-human species antibody (donor antibody) such as mouse, rat, rabbit or non-human primate having the desired specificity, affinity and binding function. In some instances, one or more FR amino acid residues of the human Ig are replaced by corresponding non-human amino acid residues. Furthermore, humanized antibodies can contain residues which are not found in the recipient antibody or in the donor antibody. These modifications can be made to refine antibody performance, if needed. A humanized antibody can comprise substantially all of at least one and, in some cases two, variable domains, in which all or substantially all of the hypervariable regions correspond to those of a non-human immunoglobulin and all, or substantially all, of the FRs are those of a human immunoglobulin sequence. The humanized antibody optionally can also include at least a portion of an immunoglobulin constant region (Fc), typically that of a human immunoglobulin. For details, see Jones et al., Nature 321: 522-525 (1986); Reichmann et al., Nature 332: 323-329 (1988); and Presta, Curr. Op. Struct. Biol. 2: 593-596 (1992).

Monoclonal antibodies against IGF-1R can be prepared and isolated using any technique that provides for the production of antibody molecules by continuous cell lines in culture. Techniques for production and isolation include but are not limited to the hybridoma technique originally described by Kohler and Milstein (Nature, 1975, 256: 495-497); the human B-cell hybridoma technique (Kosbor et al., 1983, Immunology Today 4:72; Cote et al., 1983, Proc. Natl. Acad. Sci. USA 80: 2026-2030); and the EBV-hybridoma technique (Cole et al, 1985, Monoclonal Antibodies and Cancer Therapy, Alan R. Liss, Inc., pp. 77-96).

Alternatively, techniques described for the production of single chain antibodies (see, e.g., U.S. Pat. No. 4,946,778) can be adapted to produce anti-IGF-1R single chain antibodies. Antibody-based IGF-1R kinase inhibitors useful in practicing the present methods also include anti-IGF-1R antibody fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed (see, e.g., Huse et al., 1989, Science 246: 1275-1281) to allow rapid identification of fragments having the desired specificity to IGF-1R.

Techniques for the production and isolation of monoclonal antibodies and antibody fragments are well-known in the art, and are described in Harlow and Lane, 1988, Antibodies: A Laboratory Manual, Cold Spring Harbor Laboratory, and in J. W. Goding, 1986, Monoclonal Antibodies: Principles and Practice, Academic Press, London. Humanized anti-IGF-1R antibodies and antibody fragments can also be prepared according to known techniques such as those described in Vaughn, T. J. et al., 1998, Nature Biotech. 16:535-539 and references cited therein, and such antibodies or fragments thereof are also useful in practicing the present methods.

In one aspect, an IGF-1R inhibitor can be a monoclonal antibody or an antigen binding fragment thereof. Exemplary monoclonal antibodies include, but are not limited to, AMG-479 (Amgen), BIIB022 (Biogen), IMC-A12 (ImClone), CP-751,871 (Pfizer), SCH-717454 (Schering), R-1507 (Roche) and MK-0646 (Merck).

AMG-479 (Amgen) can be administered in escalating doses intravenously (IV) over 1 hour on days 1, 15, and 29. Patients are evaluated in week 8 and those who demonstrate an objective tumor response or stable disease continue treatment beginning on day 57. Treatment repeats every 2 weeks in the absence of disease progression or unacceptable toxicity.

BIIB022 (Biogen) can be administered IV once every 3 weeks until disease progression or unacceptable toxicity.

IMC-A12 (ImClone) can be administered in different dosing and administration schedules such as, for example: (1) administration of a dose of 10 mg/kg IV over 1 hour every 2 weeks. Patients will continue treatment until progress or unacceptable toxicity develops; (2) 10 mg/kg IV over 1 hour every 2 weeks; (3) 6 mg/kg IV on days 1, 8, and 15 in a 21 day cycle; (4) 3 mg/kg IV weekly over 60 minutes; (5) IV over 1 hour on days 1, 8, 15, and 22. Treatment courses can repeat every 28 days for up to 2 years in the absence of disease progression or unacceptable toxicity; (6) IV over 1 hour once weekly. Treatment continues in the absence of disease progression or unacceptable toxicity; or (7) IV over 1 hour on days 1, 8, and 15. Courses repeat every 21 days in the absence of disease progression or unacceptable toxicity.

CP-751,871 (Pfizer) can be administered in different dosing and administration schedules such as, for example: (1) in doses ranging from 6 to 20 mg/kg on day 1 of each cycle for a total number of 17 cycles (1 year); (2) 20 mg/kg IV on study days 1 and 2 in cycle 1, and every three weeks (from day 1) thereafter; (3) 20 mg/kg IV over 2.5 hours up to 17 cycles; (4) 20 mg/kg IV every 3 weeks; (5) 20 mg/kg IV on day 1 of each 21-day cycle; (6) 6, 10 or 20 mg/kg IV every three weeks; (7) 20 mg/kg IV on day 1 of each 21-day cycle; (8) IV every 21 days for up to six cycles; (9) IV on day 1 of each 28-day cycle until either progression or toxicity; (10) 20 mg/kg IV on day 1 of each 28-day cycle until progression or unacceptable toxicity; (11) 20 mg/kg every 3 weeks for 17 cycles until progression or unacceptable toxicity develops; or (12) IV over 5 hours on days 1 and 22.

SCH-717454 (Schering) can be administered in different dosing and administration schedules such as, for example: IV once every 2 weeks until disease progression R-1507 (Roche) can be administered in different dosing and administration schedules such as, for example: (1) 3 or 9 mg/kg IV weekly or a PK-derived dose, not to exceed 16 mg/kg IV weekly; (2) IV either weekly or 3 weekly, at escalating doses, starting at 1 mg/kg; and (3) 9 mg/kg IV weekly.

MK-0646 (Merck) can be administered in different dosing and administration schedules such as, for example: (1) 10 mg/kg IV weekly over 1 hour; (2) 7.5, 10 or 15 mg/kg IV over 1 hour; (3) rising dose levels of 1.25, 2.5, 5.0, 10.0, 15.0, and 20.0 mg/kg IV weekly over 1 to 2 hours. Each three patients receive rising dose levels. Then patients enter a different dosing regimen of either every other week dosing, or every three week dosing; (4) in Phase 1.5 mg/kg IV weekly escalating to 10 mg/kg weekly following the dose limiting toxicity, then the dose will be considered. In Phase II; 5 mg/kg IV weekly; (5) 5 or 10 mg/kg IV once weekly for 4 consecutive weeks; (6) rising dose levels of 1.25, 2.5, 5.0, 10.0, 15.0, and 20.0 mg/kg IV weekly over 1 to 2 hours for 4 consecutive weeks; and (7) rising dose levels consisting of a loading dose (2.5, 5.0, 10.0, 15.0, 20.0, and 30.0 mg/kg) followed by a subsequent every other week maintenance dose (of at least 2.5 mg/kg) starting two weeks after the completion of the loading dose.

IGF-1R kinase inhibitors for use in the present methods can alternatively be based on antisense oligonucleotide constructs. Anti-sense oligonucleotides, including anti-sense RNA molecules and anti-sense DNA molecules, would act to directly block the translation of IGF-1R mRNA by binding thereto and thus preventing protein translation or increasing mRNA degradation, thus decreasing the level of IGF-1R kinase protein, and thus activity, in a cell. For example, antisense oligonucleotides of at least about 15 bases and complementary to unique regions of the mRNA transcript sequence encoding IGF-1R can be synthesized, e.g., by conventional phosphodiester techniques and administered by e.g., intravenous injection or infusion. Methods for using antisense techniques for specifically inhibiting gene expression of genes whose sequence is known are well known in the art (e.g., see U.S. Pat. Nos. 6,566,135; 6,566,131; 6,365,354; 6,410,323; 6,107,091; 6,046,321; and 5,981,732).

Small inhibitory RNAs (siRNAs) can also function as IGF-1R kinase inhibitors for use in the present methods. IGF-1R gene expression can be reduced by contacting the tumor, subject or cell with a small double stranded RNA (dsRNA), or a vector or construct causing the production of a small double stranded RNA, such that expression of IGF-1R is specifically inhibited (i.e., RNA interference or RNAi). Methods for selecting an appropriate dsRNA or dsRNA-encoding vector are well known in the art for genes whose sequence is known (e.g., see Tuschi, T., et al. (1999) Genes Dev. 13(24):3191-3197; Elbashir, S. M. et al. (2001) Nature 411:494-498; Hannon, G. J. (2002) Nature 418:244-251; McManus, M. T. and Sharp, P. A. (2002) Nature Reviews Genetics 3:737-747; Bremmelkamp, T. R. et al. (2002) Science 296:550-553; U.S. Pat. Nos. 6,573,099 and 6,506,559; and International Patent Publication Nos. WO 01/36646, WO 99/32619, and WO 01/68836).

Ribozymes can also function as IGF-1R kinase inhibitors for use in the present methods. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of IGF-1R mRNA sequences are thereby useful within the scope of the present methods. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Various modifications to the oligonucleotides can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

The antisense oligonucleotide constructs, siRNA, and ribozymes suitable for use in the present methods may be synthesized by a variety of known methods or future-developed methods. For example, one may use methods of chemical synthesis such as methods that employ Dharmacon, Inc.'s proprietary ACE® technology. Alternatively, one could also use template dependant synthesis methods. Synthesis may be carried out using modified or non-modified, natural or non-natural bases as disclosed herein. Moreover, syntheses may be carried out with or without modified or non-modified nucleic acid backbone as disclosed herein.

In addition, the antisense oligonucleotide constructs, siRNA, and ribozymes may be synthesized in a host cell by a variety of known, and any future-developed method, for synthesizing antisense oligonucleotide constructs, siRNA, and ribozymes molecules in a host cell. For example, antisense oligonucleotide constructs, siRNA, and ribozymes can be expressed from recombinant circular or linear DNA vector using any suitable promoter. Suitable promoters for expressing antisense or inhibitory RNA molecules from a vector suitable include, for example, the U6 or H1 RNA pol III promoter sequences and the cytomegalovirus promoter. Selection of other suitable promoters is within the skill in the art. Suitable vectors for use with the subject embodiments include those described in U.S. Pat. No. 5,624,803, the disclosure of which is incorporated herein in its entirely. The recombinant plasmids can also comprise inducible or regulatable promoters for expression of the antisense oligonucleotide constructs, siRNA, and ribozymes in a particular tissue or in a particular intracellular environment.

The antisense oligonucleotide constructs, siRNA, and ribozymes can be expressed from a recombinant nucleic acid vector either as two separate, complementary RNA molecules, or as a single RNA molecule with two complementary regions. Selection of vectors suitable for expressing antisense oligonucleotide constructs, siRNA, and ribozymes, methods for inserting nucleic acid sequences for expressing antisense oligonucleotide constructs, siRNA, and ribozymes into the vector, and methods of delivering the recombinant vector to the cells of interest are within the skill in the art. See, for example, Tuschl, T. (2002), Nat. Biotechnol, 20: 446-448; Brummelkamp T R et al. (2002), Science 296: 550-553; Miyagishi M et al. (2002), Nat. Biotechnol. 20: 497-500; Paddison P J et al. (2002), Genes Dev. 16: 948-958; Lee N S et al. (2002), Nat. Biotechnol. 20: 500-505; and Paul C P et al. (2002), Nat. Biotechnol. 20: 505-508, the entire disclosures of which are herein incorporated by reference. Other methods for delivery and intracellular expression suitable are described in, for example, U.S. Patent Application Publication Nos. 20040005593, 20050048647, 20050060771, the entire disclosures of which are herein incorporated by reference.

In one embodiment, following contacting cells with a catecholic butane, IGF-1R inhibitors can inhibit the activity of IGF-1R by at least about 2-fold, at least about 5 fold, at least about 10 fold, at least about 20 fold, at least about 25 fold, at least about 50 fold, at least about 100 fold or more. In another embodiment, inhibitors can inhibit the activity of IGF-1R by at least about 5%, at least about 10%, at least about 15%, at least about 20%, at least about 50%, at least about 60%, at least about 70%, at least about 80%, at least about 90%, at least about 95% or at least about 100%. In another embodiment, inhibition of IGF-1R results in stasis of symptoms of a patient that has received administration of a combination of a catecholic butane and an IGF-1R inhibitor.

Dosing of EGFR Inhibitors and IGF-JR Inhibitors

While dosing for several embodiments of IGF-1R inhibitors and EGFR inhibitors is described above, it would be understood that other dosing regiments may also be used. In various embodiments, there is synergy between a catecholic butane and the IGF-1R inhibitor and/or EGFR inhibitor which allows for a lower dose of the catecholic butane, IGF-1R inhibitor and/or EGFR inhibitor to be administered. In some embodiments, the synergy between the IGF-1R inhibitor and/or EGFR inhibitor allows for a lower dose of the catecholic butane to be dosed. In some embodiments, the synergy between the IGF-1R inhibitor and/or EGFR inhibitor and the catecholic butane allows for a lower dose of both the IGF-1R inhibitor and/or EGFR inhibitor and the catecholic butane to be dosed. In some embodiments, the synergy between the IGF-1R inhibitor and/or EGFR inhibitor and the catecholic butane allows for the IGF-1R inhibitor and/or EGFR inhibitor to be dosed less frequently. In some embodiments, the synergy between the IGF-1R inhibitor and/or EGFR inhibitor and the catecholic butane allows for the catecholic butane to be dosed less frequently. In some embodiments, the synergy between the IGF-1R inhibitor and/or EGFR inhibitor and the catecholic butane allows both the IGF-1R inhibitor and/or EGFR inhibitor and the catecholic butane to be dosed less frequently.

In some embodiments, a therapeutically effective amount of the IGF-1R inhibitor and/or EGFR inhibitor is administered to the patient. In some embodiments, the administration may be repeated, e.g., on a twice daily schedule, a daily schedule, an every other day schedule, a every three day schedule, a every four day schedule, a weekly schedule, a bi-weekly schedule, a monthly schedule, etc. In some embodiments, the IGF-1R inhibitor and/or EGFR inhibitor is administered on one of the above mentioned schedules for 1, 2, 3, 4, 5, 6 or more weeks. In some embodiments, this round of dosing is then followed by a period in which no IGF-1R inhibitor and/or EGFR inhibitor is administered (wash-out period), which may be 1, 2, 3, 4 or more weeks. In some embodiments, the wash-out period is from about 1 day to about 3 weeks, or about 3 days to about 1 week, or about 1 week to about 2 weeks, or about 2 weeks to about 3 weeks. In some embodiments, the IGF-1R inhibitor and/or EGFR inhibitor is administered twice weekly for 4 weeks, followed by a 1, 2 or 3 week wash-out period. In some embodiments, the IGF-1R inhibitor and/or EGFR inhibitor is administered every 2, 3, or 4 days for 4 weeks, followed by a 1, 2 or 3 week wash-out period. In some embodiments, the IGF-1R inhibitor and/or EGFR inhibitor is administered once a week for 4 weeks followed by a 1, 2 or 3 week wash-out period. In some embodiments, the IGF-1R inhibitor and/or EGFR inhibitor is administered twice weekly for 6 weeks, followed by a 1, 2 or 3 week wash-out period. In some embodiments, the IGF-1R inhibitor and/or EGFR inhibitor is administered every 2, 3, or 4 days for 6 weeks, followed by a 1, 2 or 3 week wash-out period. In some embodiments, the IGF-1R inhibitor and/or EGFR inhibitor is administered once a week for 6 weeks followed by a 1, 2 or 3 week wash-out period. In some embodiments, the IGF-1R inhibitor and/or EGFR inhibitor is administered twice weekly for 2 weeks, followed by a 1, 2 or 3 week wash-out period. In some embodiments, the IGF-1R inhibitor and/or EGFR inhibitor is administered every 2, 3, or 4 days for 2 weeks followed by a 1, 2 or 3 week wash-out period. In some embodiments, the IGF-1R inhibitor and/or EGFR inhibitor is administered once a week for 2 weeks followed by a 1, 2 or 3 week wash-out period.

In some embodiments, flat dosing of the IGF-1R inhibitor and/or EGFR inhibitor may be employed. Suitable flat doses contemplated herein are about 0.5, 1, 2, 3, 4, 5, 6, 7, 8, 9, 10, 15, 20, 25, 30, 35, 40, 45, 50, 55, 60, 65, 70, 75 mg/m$^2$, or any integer encompassed therein, of the IGF-1R inhibitor and/or EGFR inhibitor per dose. Alternatively, flat doses contemplated herein are about 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 140, 150, 160, 170, 180, 190, 200 mg/kg, or any integer encompassed therein, of the IGF-1R inhibitor and/or EGFR inhibitor per dose. Such doses may be administered on one of dosing schedules described herein. In some embodiments, a dose of about 0.5, 1, 2, 3, 4, 5, 6, 7, 8, 9, 10, 15, 20, 25, 30, 35, 40, 45, 50, 55, 60, 65, 70, 75 mg/m$^2$ of the IGF-1R inhibitor and/or EGFR inhibitor is administered on a daily, every other day, twice-weekly, weekly (once per week) or bi-weekly (once every other week) dosing schedule, optionally with a rest period built in after a certain number of dosing cycles. In other embodiments, a dose of about 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 140, 150, 160, 170, 180, 190, 200 mg/kg, or any integer encompassed therein, is administered on a daily, every other day, twice-weekly, weekly (once per week) or bi-weekly (once every other week) dosing schedule, optionally with a rest period (hiatus) built in after a certain number of dosing cycles.

In some embodiments, the total weekly dosage range is about 14 mg/m$^2$ to about 525 mg/m$^2$. In various embodiments, the total weekly dosage range is about 12 mg/m$^2$ to about 450 mg/m$^2$, or about 10 mg/m$^2$ to about 375 mg/m$^2$, or about 8 mg/m$^2$ to about 300 mg/m$^2$. In some embodiments, the total weekly dosage range is about 6 mg/m$^2$ to about 225 mg/m$^2$. In some embodiments, the weekly dosage range is about 4 mg/m$^2$ to about 150 mg/m$^2$, or about 2 mg/m$^2$ to about 75 m g/m$^2$. In some embodiments, the weekly dosage range is about 3.5 mg/m$^2$ to about 350 mg/m$^2$, or about 3.0 mg/m$^2$ to about 300 mg/m$^2$, or about 2.5 mg/m$^2$ to about 250 mg/m$^2$, or about 2.0 mg/m$^2$ to about 200 mg/m$^2$, or about 1.5 mg/m$^2$ to about 150 mg/m$^2$, or about 1.0 mg/m$^2$ to about 100 mg/m$^2$, or about 0.5 mg/m$^2$ to about 50 mg/m$^2$.

In certain embodiments, the therapeutically effective amount of the IGF-1R inhibitor and/or EGFR inhibitor is about 0.5-50 mg/m$^2$. In some embodiments, the therapeutically effective amount of the IGF-1R inhibitor and/or EGFR inhibitor is about 2-75 mg/m$^2$. A catecholic butane can be administered at the same time as an IGF-1R inhibitor and/or EGFR inhibitor. Alternatively, a catecholic butane can be administered prior to an IGF-1R inhibitor and/or EGFR inhibitor.

In some embodiments, suitable dosages of an IGF-1R inhibitor and/or EGFR inhibitor are given intravenously over 3 hours every 8 hours for 3 days and repeated every 6 weeks. In some embodiments, the dosages range from 45 m g/m$^2$ per course to 135 mg/m$^2$ per course.

Kits

Compounds described herein can be packaged in a kit. In some embodiments, provided herein is a kit including a catecholic butane in a dosage form, especially a dosage form for oral administration or intravenous administration. In some embodiments, the kit further includes an IGF-1R inhibitor in a dosage form, especially a dosage form for oral administration or intravenous administration. Additionally or alternatively, the kit further includes an EGFR inhibitor in a dosage form, especially a dosage form for oral administration or intravenous administration.

In specific embodiments, the catecholic butane and the IGF-1R/EGFR inhibitor are in separate dosage forms. In some embodiments, the kit includes one or more doses of a catecholic butane in tablet form for oral administration. In other embodiments, however, the dose or doses a catecholic butane may be present in a variety of dosage forms, such as capsules, caplets, gel caps, powders for suspension, etc. In some embodiments, the kit includes one or more doses of an IGF-1R/EGFR inhibitor in tablets for oral administration. In other embodiments, however, the dose or doses of an IGF-1R/EGFR inhibitor may be present in a variety of dosage forms, such as capsules, caplets, gel caps, powders for suspension, etc.

The container means of the kits will generally include at least one vial, test tube, flask, bottle, syringe and/or other container means, into which the at least one polypeptide can be placed, and/or preferably, suitably aliquoted. The kits can include a means for containing at least one fusion protein, detectable moiety, reporter molecule, and/or any other reagent containers in close confinement for commercial sale. Such containers may include injection and/or blow-molded plastic containers in which the desired vials are stored. Kits can also include printed material for use of the materials in the kit.

Packages and kits can additionally include a buffering agent, a preservative and/or a stabilizing agent in a pharmaceutical formulation. Each component of the kit can be enclosed within an individual container and all of the various containers can be within a single package. Kits can be designed for cold storage or room temperature storage.

Additionally, the preparations can contain stabilizers (such as bovine serum albumin (BSA)) to increase the shelf-life of the kits. Where the compositions are lyophilized, the kit can contain further preparations of solutions to reconstitute the lyophilized preparations. Acceptable reconstitution solutions are well known in the art and include, for example, pharmaceutically acceptable phosphate buffered saline (PBS).

Additionally, the packages or kits provided herein can further include any of the other moieties provided herein such as, for example, one or more reporter molecules and/or one or more detectable moieties/agents.

Packages and kits can further include one or more components for an assay, such as, for example, an ELISA assay, cytotoxicity assay, ADP-Ribosyltransferase activity assay, etc. Samples to be tested in this application include, for example, blood, plasma, and tissue sections and secretions, urine, lymph, and products thereof. Packages and kits can further include one or more components for collection of a sample (e.g., a syringe, a cup, a swab, etc.).

Packages and kits can further include a label specifying, for example, a product description, mode of administration and/or indication of treatment. Packages provided herein can include any of the compositions as described herein for treatment of any of the indications described herein.

The term "packaging material" refers to a physical structure housing the components of the kit. The packaging material can maintain the components sterilely, and can be made of material commonly used for such purposes (e.g., paper, corrugated fiber, glass, plastic, foil, ampules, etc.). The label or packaging insert can include appropriate written instructions. Kits, therefore, can additionally include labels or instructions for using the kit components in any method described herein. A kit can include a compound in a pack, or dispenser together with instructions for administering the compound in a method described herein.

In some embodiments, a kit includes at least three dosage forms, one comprising a catecholic butane, one comprising an IGF-1R inhibitor and the other comprising an EGFR inhibitor. In some embodiments, the kit includes sufficient doses for a period of time. In some specific embodiments, the each dose is physically separated into a compartment, in which each dose is segregated from the others.

In some embodiments, the kit includes at least two dosage forms one comprising an catecholic butane and one comprising an IGF-1R inhibitor or an EGFR inhibitor. In some embodiments, the kit includes sufficient doses for a period of time. In some specific embodiments, the each dose is physically separated into a compartment, in which each dose is segregated from the others.

In particular embodiments, the kit may advantageously be a blister pack. Blister packs are known in the art, and generally include a clear side having compartments (blisters or bubbles), which separately hold the various doses, and a backing, such as a paper, foil, paper-foil or other backing, which is easily removed so that each dose may be separately extracted from the blister pack without disturbing the other doses. In some embodiments, the kit may be a blister pack in which each dose of the catecholic butane, the IGF-1R inhibitor and the EGFR inhibitor are segregated from the other doses in separate blisters or bubbles. In some such embodiments, the blister pack may have perforations, which allow each daily dose to be separated from the others by tearing it away from the rest of the blister pack. The separate dosage forms may be contained within separate blisters. Segregation of the active pharmaceutical ingredients into separate blisters can be advantageous in that it prevents separate dosage forms (e.g., tablet and capsule) from contacting and damaging one another during shipping and handling. Additionally, the separate dosage forms can be accessed and/or labeled for administration to the patient at different times.

In some embodiments, the third active pharmaceutical ingredient may be in the form of a liquid or a reconstitutable powder, which may be separately sealed (e.g., in a vial or ampoule) and then packaged along with a blister pack containing separate dosages of the catecholic butane, the IGF-1R inhibitor and the EGFR inhibitor. In some embodiments, the IGF-1R inhibitor and/or the EGFR inhibitor is in the form of a liquid or reconstitutable powder that is separately sealed (e.g., in a vial or ampoule) and then packaged along with a blister pack containing separate dosages of the catecholic butane. These embodiments would be especially useful in a clinical setting where prescribed doses of the catecholic butane, the IGF-1R inhibitor and the EGFR inhibitor would be used on a dosing schedule in which the catecholic butane is administered on certain days, the IGF-1R inhibitor is administered on the same or different days and the EGFR inhibitor is administered on the same or different days. Such a combination of blister pack could also include instructions for administering each of the active agents on a dosing schedule adapted to provide a synergistic or sequelae-treating effect.

In other embodiments, the kit may be a container having separate compartments with separate lids adapted to be opened on a particular schedule. For example, a kit may comprise a box (or similar container) having seven compartments, each for a separate day of the week, and each compartment marked to indicate which day of the week it corresponds to. In some specific embodiments, each compartment is further subdivided to permit segregation of one active pharmaceutical ingredient from another. As stated above, such segregation is advantageous in that it prevents damage to the dosage forms and permits dosing at different times and labeling to that effect. Such a container could also include instructions for administering one or more active agents on a dosing schedule adapted to provide a synergistic or sequelae-treating effect.

The kits may also include instructions teaching the use of the kit according to the various methods and approaches described herein. Such kits optionally include information, such as scientific literature references, package insert materials, clinical trial results, and/or summaries of these and the like, which indicate or establish the activities and/or advantages of the composition, and/or which describe dosing, administration, side effects, drug interactions, disease state for which the composition is to be administered, or other information useful to the health care provider. Such information may be based on the results of various studies, for example, studies using experimental animals involving in vivo models and studies based on human clinical trials. In various embodiments, the kits described herein can be provided, marketed and/or promoted to health providers, including physicians, nurses, pharmacists, formulary officials, and the like. Kits may, in some embodiments, be marketed directly to the consumer. In certain embodiments, the packaging material further comprises a container for housing the composition and optionally a label affixed to the container. The kit optionally comprises additional components, such as but not limited to syringes for administration of the composition.

Instructions can include instructions for practicing any of the methods described herein including treatment methods. Instructions can additionally include indications of a satisfactory clinical endpoint or any adverse symptoms that may occur, or additional information required by regulatory agencies such as the Food and Drug Administration for use on a human subject.

The instructions may be on "printed matter," e.g., on paper or cardboard within or affixed to the kit, or on a label affixed to the kit or packaging material, or attached to a vial or tube containing a component of the kit. Instructions may additionally be included on a computer readable medium, such as a disk (floppy diskette or hard disk), optical CD such as CD- or DVD-ROM/RAM, magnetic tape, electrical storage media such as RAM and ROM, IC tip and hybrids of these such as magnetic/optical storage media.

In some embodiments, a kit may comprise reagents for the detection of DNA, RNA or protein expression levels in a sample of tumor cells from a patient to be treated.

Kits can, in some aspects, contain reagents and materials to conduct any of the assays described herein.

EXAMPLES

The application may be better understood by reference to the following non-limiting examples, which are provided as exemplary embodiments of the application. The following examples are presented in order to more fully illustrate embodiments and should in no way be construed, however, as limiting the broad scope of the application. While certain embodiments of the present application have been shown and described herein, it will be obvious that such embodiments are provided by way of example only. Numerous variations, changes, and substitutions may occur to those skilled in the art; it should be understood that various alternatives to the embodiments described herein may be employed in practicing the methods described herein.

Example 1

Treatment of Basal Cell Epithelioma

This example describes the antineoplastic activity of compositions containing catecholic butanes in clinical studies on human patients diagnosed with basal cell epithelioma.

Catecholic butanes may be prepared for topical administration for treatment of basal cell epithelioma.

The surface of the lesions are tape stripped prior to each application. The test medication is applied directly to the lesion with a coating approximately 2 mm thick and covered with a dressing. After a minimum of seven (7) days, a second application is applied at the discretion of the investigator. The dose ranges from 20-350 mg/cm$^2$ with as much as 500 mg/cm$^2$ utilized for deep tumors. To determine the effect of the test compound on the malignant neoplasma, an excisional biopsy is obtained 30 days after the initial treatment.

Example 2

Treatment of Actinic Keratosis

Human patients diagnosed with actinic keratosis are treated with catecholic butane compositions prepared for topical application.

The test composition is applied directly to the lesion with a coating of approximately 2 mm and confined to the lesion margin. A dressing is applied to the lesion. A visual examination and measurement of the lesion is performed 7 and 14 days following the initial treatment. At the discretion of the investigator, a second treatment with the same test compound may be applied.

In order to determine whether the test compound eradicated the pre-malignant neoplasm, a punch biopsy is obtained 30-60 days after the initial treatment. If the biopsy report is negative, i.e., no tumor, the patient is examined every 6 months for a period of 12 months for recurrence.

Example 3

Treatment of Tumor Lesions

Canine patients with various tumor lesions are treated with catecholic butane containing compositions prepared for topical application.

The animals are restrained from movement for two hours physically or with sedatives (e.g. 0.03 mg oxymorphone/lb$^2$ with atropine sulfate). After clipping, washing and measuring the tumor size, the skin surface is abraded until bleeding occurred. To enhance the penetration of the test compositions for large or subdermal tumors, a 20 or 22 gauge needle is used to puncture the tumor. After blotting the skin dry of blood, the tumor site is covered with a 1-2 mm coating of the test composition extending 5 mm peripherally. After 2 hours, the compound is wiped off and the area gently cleansed. The test composition is applied up to three times within a two-week interval or until the tumor clears.

Example 4

Inhibition of HUVEC Growth and 3H-Thymidine Incorporation Assay

A number of assays are available to assess inhibition of cell growth.

In one example, HUVECs are cultured in 75-cm$^2$ flasks (Falcon, Becton-Dickinson, Franklin Lakes, N.J.) in a $CO_2$ incubator at 37° C. under sub-confluent conditions. Cells are detached by incubating with Hanks' balanced salt solution with 15 mM EDTA in 25 mM HEPES buffer, pH 7.3, at 37° C. for 15 min. After washing twice with ice-cold PBS, cells are re-suspended in endothelial cell growth medium at a concentration of 25,000 cells/ml. In additional experiments, human umbilical vein endothelial cells (HUVECs) are suspended and cultured in an endothelial cell growth medium free of FBS and bovine brain extracts. A 200 µl aliquot of cell suspension is seeded to each well of 96-well culture plates. Cells are cultured at 37° C. in a $CO_2$ incubator overnight before NDGA or sterile PBS are added in triplicate. Culture plates are kept in the incubator for 72 hr, during which fresh media and NDGA/PBS are replaced every 24 hr. $^3$H-thymidine (1 µCi) is added into each well and the plates are incubated for 20 hr. Cells are washed with PBS followed by treatment with 100 µl/well trypsin-EDTA (0.05% trypsin, 0.53 mM EDTA) at 37° C. for 15 min. Cells are harvested onto glass fiber filters (Wallac Printed FiltermatA) using Harvester 96 (TOMTEC, Hamden, Conn.) and $^3$H-radioactivity is determined in a Trilux 1540 MicroBeta Liquid Scintillation and Luminescence Counter (Wallac, Turku, Finland).

Example 5

In Vivo Treatment of Human Breast Adenocarcinoma

The in vivo antitumor effect of catecholic butanes is determined against MX-1 (human breast adenocarcinoma) cells.

Male or female athymic BALB/c mice, six to eight weeks of age and weighing 20 to 35 grams are used. MX-1 cells are cultured in the standard RPMI-1640 media and implanted subcutaneously in the flank of the nude mice in order to propagate the tumor line. Nude mice are implanted with 25 mg of the MX-1 solid tumor fragments. Tumors which reach the 25-100 mm$^2$ range are used for the experiment. Test compound (0.1 mL) is injected directly into the tumor.

The tumors are measured periodically to determine their weight calculated by using half the product of the length (L) times the width (W) times the height (H) of the tumor. The procedure is repeated at regular intervals until 60 days after the initial treatment or all mice have died. Mice which show no evidence of tumors are kept for 60 days to evaluate the potential for tumor recurrence at which time tumor characteristics, if any, are recorded.

Example 6

Anti-cancer Therapy of Preformed Human Breast Cancer Tumors

The effect of the catecholic butanes described herein can be assessed with respect to their anti-cancer effect on preformed human breast cancer tumors in human skin grafted into SCID mice.

Briefly, MCF-7 cells (8×10$^6$ cells in 0.1 ml PBS) are transplanted intradermally into human full-thickness skin grafted into SCID mice when the grafts showed no signs of inflammation, contraction or rejection. The mice are left untreated until distinct palpable tumors (3 to 6 mm in diameter in most cases) appear. Mice with distinct tumors are divided into groups for the therapeutic studies. Control animals are administered sterile PBS intravenously (i.v.) via the tail vein. Groups of test animals (4 mice per group) are administered 5 mg/kg, 10 mg/kg, 25 mg/kg, or 50 mg/kg, of catecholic butane intravenously (i.v.) via the tail vein. Administration is as follows: once per week; twice per week; three times daily for three weeks with one week hiatus; two times daily for three weeks with one week hiatus; or one time daily for three weeks with one week hiatus.

Additional groups of mice may be added to test for combination therapy of catecholic butanes with an EGFR inhibitor, an IGF-1R inhibitor, or both.

During the treatment, mice are monitored daily for tumor size and morbidity. Mice are weighed twice a week using an electronic balance (OHAUS™ Model GT210). Tumor size is measured three times a week using an electronic caliper (PRO-MAX 6 inch caliper; Fowler Co., Newton, Mass.) con-

Example 7

SCID Mouse Model for Ovarian Cancer

To determine the ability of catecholic butanes to treat ovarian cancer, an ovarian cancer cell line may be used in SCID mice.

Briefly, ovarian cancer cells are implanted into SCID mice to generate ovarian tumors. Groups of mice bearing established tumors are treated by i.v. administration of escalating doses (starting at 5 mg/kg body weight) of catecholic butane. Control animals are treated with sterile PBS. Additional groups of mice may be added to test for combination therapy of catecholic butanes with an EGFR inhibitor, an IGF-1R inhibitor, or both.

Mice are monitored and tumor growth is measured via sacrifice of animals on a weekly basis. Tumors are measured as described above.

Example 8

SCID Mouse Model for Kidney Cancer

To determine the ability of catecholic butanes to treat kidney cancer, a kidney cancer cell line is used in SCID mice.

Briefly, kidney cancer cells are implanted into SCID mice to generate kidney tumors. Groups of mice bearing established tumors are treated by i.v. administration of escalating doses (starting at 5 mg/kg body weight) of catecholic butane. Control animals are treated with sterile PBS. Additional groups of mice may be added to test for combination therapy of catecholic butanes with an EGFR inhibitor, an IGF-1R inhibitor, or both.

Mice are monitored and tumor growth is measured via sacrifice of animals on a weekly basis. Tumors are measured as described above.

Example 9

SCID Mouse Model for Myeloma

To determine the ability of catecholic butanes to treat myeloma, a myeloma cell line is used in SCID mice.

Briefly, myeloma cancer cells are implanted into SCID mice to generate myeloma tumors. Groups of mice bearing established tumors are treated by i.v. administration of escalating doses (starting at 5 mg/kg body weight) of catecholic butane. Control animals are treated with sterile PBS. Additional groups of mice may be added to test for combination therapy of catecholic butanes with an EGFR inhibitor, an IGF-1R inhibitor, or both.

Mice are monitored and tumor growth is measured via sacrifice of animals on a weekly basis. Tumors are measured as described above.

Example 10

Toxicology in Cynomolgus Monkeys

Cynomolgus monkeys are utilized in a study to address the toxicology of NDGA.

Briefly, monkeys are dosed weekly for three weeks with 5.0 mg/kg, 10.0 mg/kg, 25.0 mg/kg, 50 mg/kg or 100 mg/kg of NDGA. Placebo animals are dosed on the same schedule with an appropriate solution in the absence of NDGA. The doses are administered intravenously bolus over 30 to 60 minutes and at least six animals are dosed at each dose level. Toxicology is assessed via one or more of the following indications: body weight measurements, basic physiologic clinical measurements, serial serum chemistry, hematologic evaluations and histopathological evaluations.

Example 11

Human Clinical Trial of the Safety and Efficacy of a Catecholic Butane

Objective: To assess the safety and pharmacokinetics of administered catecholic butane (e.g., NDGA).

Study Design: This will be a Phase I, single-center, open-label, randomized dose escalation study followed by a Phase II study in cancer patients with disease that can be biopsied. Patients should not have had exposure to the catecholic butane (e.g., NDGA) prior to the study entry. Patients must not have received treatment for their cancer within 2 weeks of beginning the trial. Treatments include the use of chemotherapy, hematopoietic growth factors, and biologic therapy such as monoclonal antibodies. The exception is the use of hydroxyurea for patients with a white blood cell (WBC) count of $>30\times10^3/\mu L$. This duration of time appears adequate for wash out due to the relatively short-acting nature of most anti-leukemia agents. Patients must have recovered from all toxicities (to grade 0 or 1) associated with previous treatment. All subjects are evaluated for safety and all blood collections for pharmacokinetic analysis are collected as scheduled. All studies are performed with institutional ethics committee approval and patient consent.

Phase I: Patients receive catecholic butane (e.g., NDGA) according to a pre-determined dosing regimen. Cohorts of 3-6 patients receive escalating doses of NDGA until the maximum tolerated dose (MTD) for the combination of NDGA is determined. Test dose ranges are initially determined via the established individual dose ranges for NDGA. The MTD is defined as the dose preceding that at which 2 of 3 or 2 of 6 patients experience dose-limiting toxicity. Dose limiting toxicities are determined according to the definitions and standards set by the National Cancer Institute (NCI) Common Terminology for Adverse Events (CTCAE) Version 3.0 (Aug. 9, 2006).

NDGA can be administered in different dosing and administration schedules.

A catecholic butane (e.g., NDGA) is administered in an amount to provide a mean area under the blood plasma concentration curve of about 25 to about 700 ng·h/mL. A catecholic butane (e.g., NDGA) can also be administered to provide a mean maximum plasma concentration of between about 1 and about 50 ng/mL. Test dose ranges are initially determined via the established individual dose ranges for a patient.

For the treatment of prostate cancer, patients are orally administered NDGA twice-daily on days 1-28; treatment repeats every 28 days in the absence of disease progression or unacceptable toxicity. Alternatively, patients may be orally administered 2000 mg of NDGA once-daily. Alternatively, patients are administered NDGA IV on days 1-5; treatment repeats every 28 days in the absence of disease progression or unacceptable toxicity.

For treatment of solid tumors of epithelial origin, patients are administered NDGA intravenously weekly over 24 hours. Doses commence with 100 mg/hour (2400 mg in a 24-hour period) with escalation in 5 cohorts of 3 to 6 patients with increments of 25 mg per hour to a maximum of 200 mg/hr (4800 mg in a 24-hour period) or until MTD is defined.

For treatment of refractory solid tumors (e.g., malignant tumors of the head and neck), patients are administered NDGA intravenously once per week, initially for three weeks. Doses will be escalated on the starting schedule to a target of 20 mg/cm$^3$ tumor volume. Dose escalation will continue, assuming tolerability, so that cohorts will be treated for 6 weeks and, finally, for 8 weeks. Alternatively, patients may be administered NDGA intravenously for five consecutive days every 28 days to patients with solid tumors refractory to EGFR inhibitors or IGF-1R inhibitors.

For treatment of recurrent high-grade glioma, patients are administered NDGA intravenously. Cohorts of 3-6 patients receive escalating doses of NDGA until the MTD is determined. The MTD is the dose preceding that at which 2 or 3 of 6 patients experience dose-limiting toxicity.

For treatment of leukemia, patients are administered NDGA intravenously over 6 hours three times per week for two weeks followed by one week rest. Adverse events and toxicity are assessed prior to each cycle of treatment and at times when clinically indicated. Maximum tolerated doses (MTD) and dose limiting toxicity (DLT) are determined. Dose will be escalated from 1000, to 1500 and 2200 mg or de-escalated to 500 mg if 1000 mg exceeds the MTD.

Phase II: Patients receive NDGA as in phase I at the MTD determined in phase I. Treatment is administered as described above in phase I in the absence of disease progression or unacceptable toxicity. After completion of one or more courses of study therapy, patients who achieve a complete or partial response may receive an additional one or more courses of treatment. Patients who maintain stable disease for more than 2 months after completion of study therapy may receive an additional one or more courses of treatment at the time of disease progression, provided they meet original eligibility criteria.

Blood Sampling Serial blood is drawn by direct vein puncture before and after administration of the catecholic butane. Venous blood samples (5 mL) for determination of serum concentrations are obtained at about 10 minutes prior to dosing and at approximately the following times after dosing: days 1, 2, 3, 4, 5, 6, 7, and 14. Samples may also be taken at later time points. Each serum sample is divided into two aliquots. All serum samples are stored at −20° C. Serum samples are shipped on dry ice.

Pharmacokinetics: Patients undergo plasma/serum sample collection for pharmacokinetic evaluation before beginning treatment and at days 1, 2, 3, 4, 5, 6, 7, and 14. Samples may also be taken at later time points. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Patient Response to therapy: Patient response is assessed via imaging with X-ray, CT scans, and/or MRI, and imaging is performed prior to beginning the study and at the end of the first cycle, with additional imaging performed every four weeks or at the end of subsequent cycles. Imaging modalities are chosen based upon the cancer type and feasibility/availability, and the same imaging modality is utilized for similar cancer types as well as throughout each patient's study course. Response rates are determined using the RECIST criteria. (Therasse et al, *J. Natl. Cancer Inst.* 2000 Feb. 2; 92(3):205-16; and world wide web site: ctep.cancer.gov/forms/TherasseRECISTJNCI.pdf). Patients also undergo cancer/tumor biopsy to assess changes in progenitor cancer cell phenotype and clonogenic growth by flow cytometry, Western blotting, and IHC, and for changes in cytogenetics by FISH. After completion of study treatment, patients are followed periodically for 4 weeks. Statistical significance of results of the assays is assessed.

Example 12

Clinical Trial for Myeloma

This example describes a randomized, blinded, placebo-controlled, multicenter, Phase II study designed to provide a preliminary assessment of the safety and efficacy of NDGA in patients with myeloma. Approximately about 100—about 800 patients are enrolled, with about 50—about 400 patients being assigned to a treatment group and about 50—about 400 patients assigned to a placebo group. The trial will consist of the administration of intravenous or oral administration of NDGA as described above in Example 11. The time frame of the study is estimated at about 6 months—about 5 years, with continued therapy for responders as indicated at the end of the initial study. Additional outcome measures are as follows:

Primary outcome measure: overall response rate. One goal of the study is to demonstrate an increase overall response rate from about 40% with placebo to about 60% (or more) with NDGA.

Secondary outcome measures that can be assessed include duration of response, time to tumor progression, overall survival, serious and non-serious adverse events. For example, a treatment may prevent progression of the disease (i.e., stasis) or may result in an improvement. Alternately, or in addition, other goals can be measured with respect to one or more of the following: decreased tumor burden, decreased neovascularization, reduced side effects, decreased adverse reactions, and/or increased patient compliance.

Example 13

Clinical Trial of Kidney Cancer

This example describes a randomized, blinded, placebo-controlled, multicenter, Phase II study designed to provide a preliminary assessment of the safety and efficacy of NDGA in patients with renal cell cancer (kidney cancer). Approximately about 100—about 800 patients are enrolled, with about 50—about 400 patients being assigned to a treatment group and about 50—about 400 patients assigned to a placebo group. The trial will consist of the administration of intravenous or oral administration of NDGA as described above in Example 11. The time frame of the study is estimated at about 6 months—about 5 years, with continued therapy for responders as indicated at the end of the initial study. Additional outcome measures are as follows:

Primary outcome measure: progression-free survival. One goal of the study is to demonstrate an increase in progression free survival from about 9-13 months in the placebo arm to about 14-18 months (or more) in the NDGA arm.

Secondary outcome measures that can be assessed include duration of response, time to tumor progression, overall survival, serious and non-serious adverse events. For example, a treatment may prevent progression of the disease (i.e., stasis) or may result in an improvement. Alternately, or in addition, other goals can be measured with respect to one or more of the following: decreased tumor burden, decreased neovascularization, reduced side effects, decreased adverse reactions, and/or increased patient compliance.

Example 14

Clinical Trial for Hepatocellular Cancer

This example describes a randomized, blinded, placebo-controlled, multicenter, Phase II study designed to provide a preliminary assessment of the safety and efficacy of NDGA in patients with renal cell cancer (kidney cancer). Approximately about 100—about 800 patients are enrolled, with about 50—about 400 patients being assigned to a treatment group and about 50—about 400 patients assigned to a placebo group. The trial will consist of the administration of intravenous or oral administration of NDGA as described above in Example 11. The time frame of the study is estimated at about 6 months—about 5 years, with continued therapy for responders as indicated at the end of the initial study. Additional outcome measures are as follows:

Primary Outcome Measures: Progression-free survival. One goal of the study is to demonstrate an increase in progression free survival from about 3-9 months in the placebo arm to about 6-12 months (or more) in the NDGA arm.

Secondary outcome measures that can be assessed include duration of response, time to tumor progression, overall survival, serious and non-serious adverse events. For example, a treatment may prevent progression of the disease (i.e., stasis) or may result in an improvement. Alternately, or in addition, other goals can be measured with respect to one or more of the following: decreased tumor burden, decreased neovascularization, reduced side effects, decreased adverse reactions, and/or increased patient compliance.

Example 15

Clinical Trial for Ovarian Cancer

This example describes a randomized, blinded, placebo-controlled, multicenter, Phase II study designed to provide a preliminary assessment of the safety and efficacy of NDGA in patients with ovarian cancer. Approximately about 100—about 800 patients are enrolled, with about 50—about 400 patients being assigned to a treatment group and about 50—about 400 patients assigned to a placebo group. The trial will consist of the administration of intravenous or oral administration of NDGA as described above in Example 11. The time frame of the study is estimated at 6 months—about 5 years, with continued therapy for responders as indicated at the end of the initial study. Additional outcome measures are as follows:

Primary Outcome Measure: Progression-free survival. One goal of the study is to demonstrate an increase in progression free survival from about 3-6 months in the placebo arm to about 4-12 months (or more) in the NDGA arm.

Secondary outcome measures that can be assessed include duration of response, time to tumor progression, overall survival, serious and non-serious adverse events. For example, a treatment may prevent progression of the disease (i.e., stasis) or may result in an improvement. Alternately, or in addition, other goals can be measured with respect to one or more of the following: decreased tumor burden, decreased neovascularization, reduced side effects, decreased adverse reactions, and/or increased patient compliance.

Example 16

Clinical Trial for Combination Therapy for Ovarian Cancer

This example describes a randomized, blinded, placebo-controlled, multicenter, Phase II study designed to provide a preliminary assessment of the safety and efficacy of combining NDGA with topotecan in patients with ovarian cancer. Approximately about 100—about 800 patients are enrolled, with about 50—about 400 patients being assigned to a treatment group and about 50—about 400 patients assigned to a placebo group. The trial will consist of the administration of intravenous repeating doses of NDGA as described above in Example 11 combined with topotecan at about 1.5 mg/m$^2$ by intravenous infusion on days 1-5 of a 21-day course, with courses repeating throughout the study. Control patients are administered topotecan with placebo. The time frame of the study is estimated at about 6 months—about 5 years, with continued therapy for responders as indicated at the end of the initial study. Additional outcome measures are as follows:

Primary outcome measure: progression-free survival. One goal of the study is to demonstrate an increase in progression free survival from about 3-6 months in the topotecan plus placebo arm to about 6-12 months (or more) in the topotecan plus NDGA arm.

Secondary outcome measures that can be assessed include duration of response, time to tumor progression, overall survival, serious and non-serious adverse events. For example, a treatment may prevent progression of the disease (i.e., stasis) or may result in an improvement. Alternately, or in addition, other goals can be measured with respect to one or more of the following: decreased tumor burden, decreased neovascularization, reduced side effects, decreased adverse reactions, and/or increased patient compliance.

Example 17

In Vitro Inhibition of Multiple Anti-Cancer Targets by NDGA (TT-100)

Inhibition of lipoxygenase activity was determined by use of a lipoxygenase inhibitor screening assay kit (Cayman Chemicals, Ann Arbor, Mich.). Purified 15-LOX (soybean) was incubated with varying concentrations of TT-100 prior to the addition of the substrates arachidonic or linoleic acid. LOX activity was determined by the amount of hydroperoxides produced, as quantified by colorimetric readout. Inhibition of RTK activity was determined by ELISA as follows. TT-100 was incubated with recombinant proteins representing the kinase domain of the IGF-1R or EGFR (Cell Signaling Technology, Danvers, Mass.) for 5 minutes prior to the addition of ATP (10 μM) and biotin-conjugated substrate peptides (IRS-1 sequence or PTP1B, respectively) (0.2 μM) for a 45 minute reaction. The reaction was stopped with 50 mM EDTA, and biotin-conjugated substrate was captured on a 96-well streptavidin-coated plate. Tyrosine phosphorylation of captured substrate was determined by incubation with anti-phosphotyrosine antibody conjugated to HRP (Santa Cruz Biotechnology, Santa Cruz, Calif.) and colorimetric readout on a 96 well plate reader.

NDGA (TT-100) directly inhibits the tyrosine kinase activity of purified IGF-1R and EGFR with greater affinity than its actions against purified lipoxygenase (LOX).

Example 18

In Vitro Inhibition of Iressa-Resistant NSCLC Cells by NDGA (TT-100)

Figure 2:
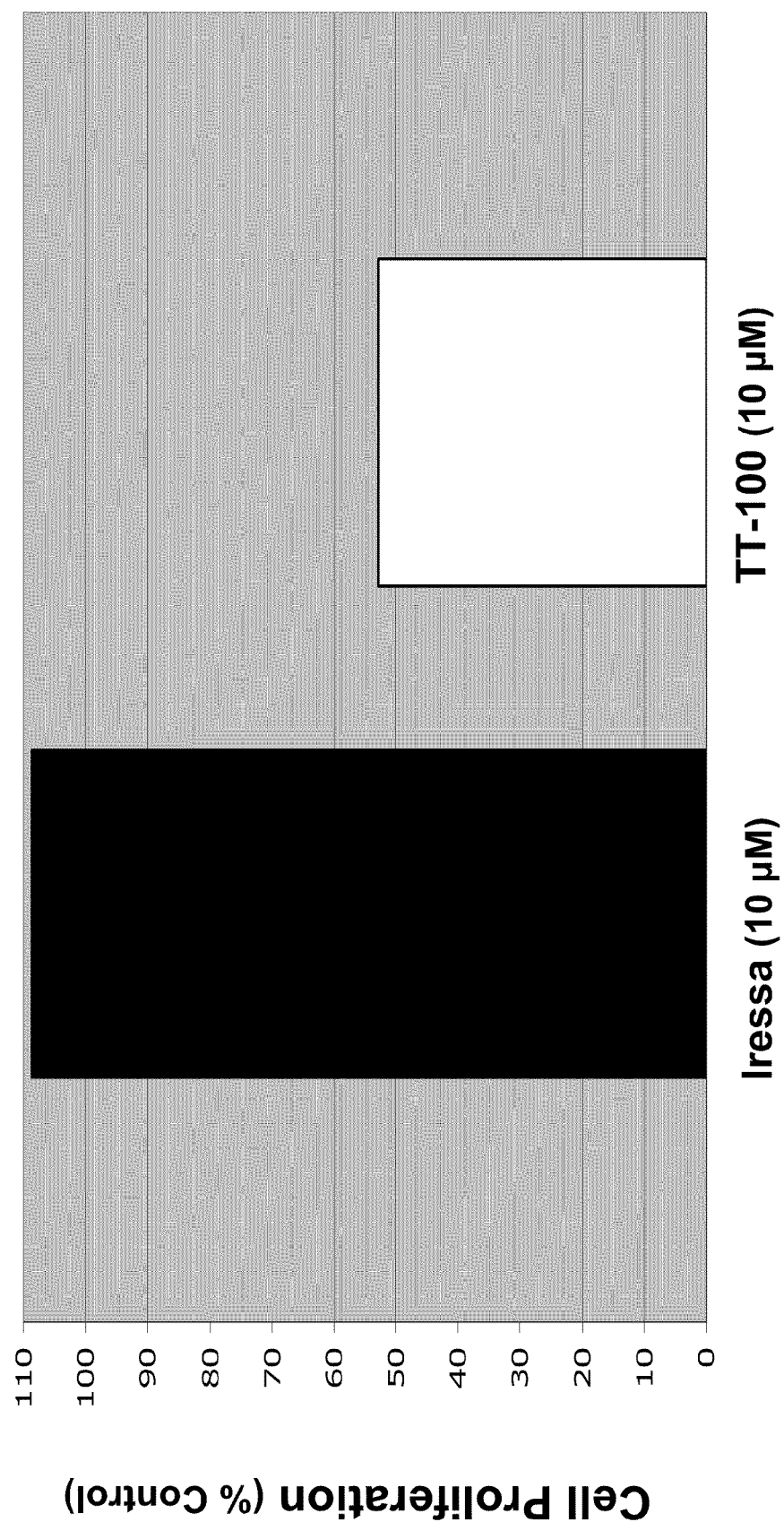
FIG. 2 demonstrates that TT-100 inhibits Iressa-resistant NSCLC cells expressing EGFR T790M mutation.

H1975 NSCLC cells expressing EGFR T790M mutation were incubated in the presence of 10 μM Iressa or 10 μM TT-100 for 3 days. Cell content was measured and shown as the percent growth of the control cells incubated in the absence of Iressa and TT-100. As shown in FIG. 2, TT-100 inhibited proliferation of Iressa-resistant NSCLC cells expressing EGFR T790M mutation. Proliferation of H1975 NSCLC cells was reduced by approximately 50% in the presence of TT-100.

Figure 3:
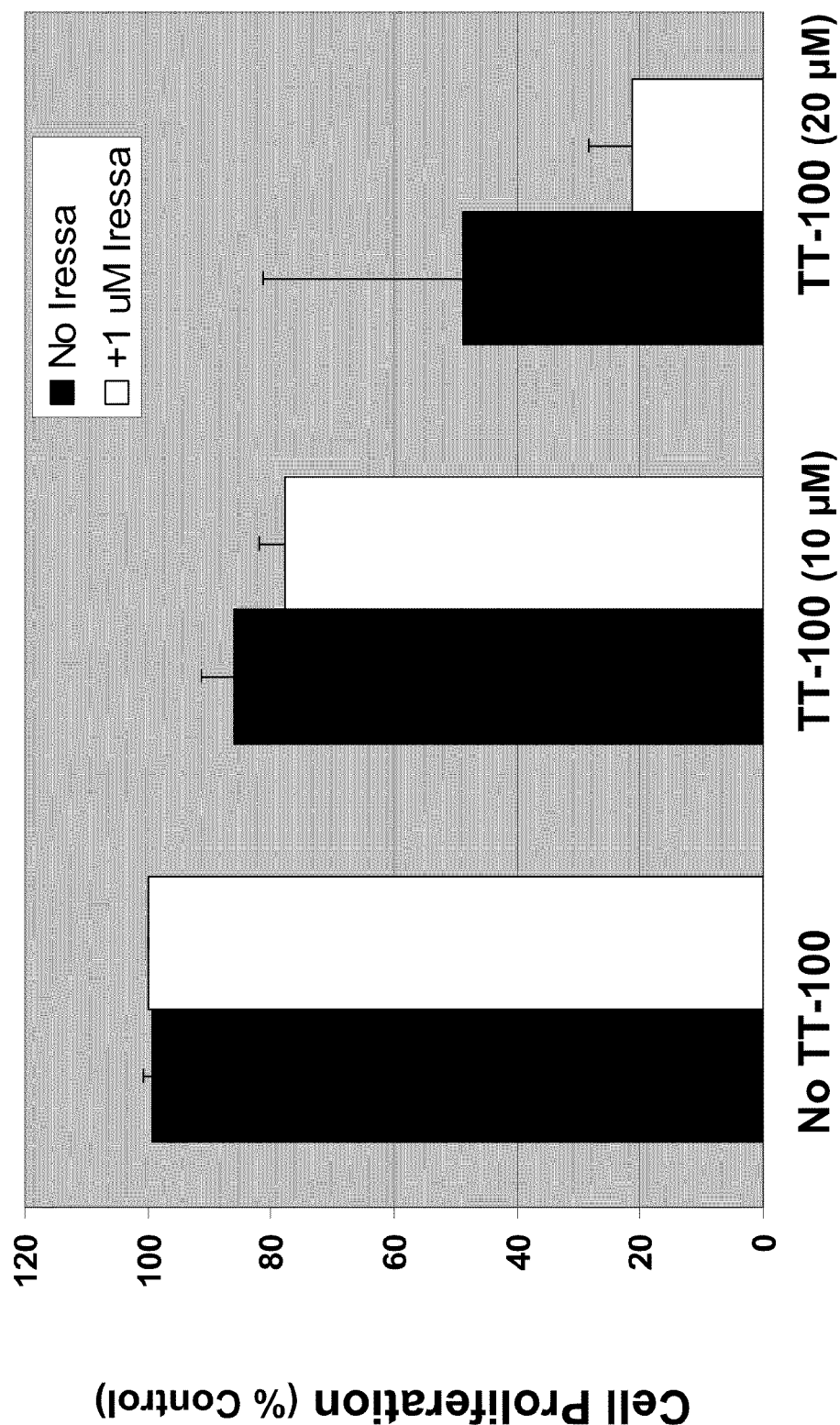
FIG. 3 demonstrates that TT-100 synergizes with clinical concentrations of Iressa in drug-resistant NSCLC cells.

H1299 NSCLC cells were incubated in the absence or presence of 1 μM Iressa with or without either 10 μM or 20 μM TT-100 for 3 days. Cell content was measured and shown as the percent growth of the control cells incubated in the absence of Iressa and TT-100. As shown in FIG. 3, H1299 NSCLC cells were resistant to clinically deliverable concentrations of Iressa. TT-100 alone inhibited the proliferation of H1299 NSCLC cells, especially when used at 20 μM. Furthermore, TT-100 synergized with clinical concentrations of Iressa in these drug-resistant NSCLC cells as cell proliferation was further reduced in the presence of both Iressa and TT-100.

Figure 4:
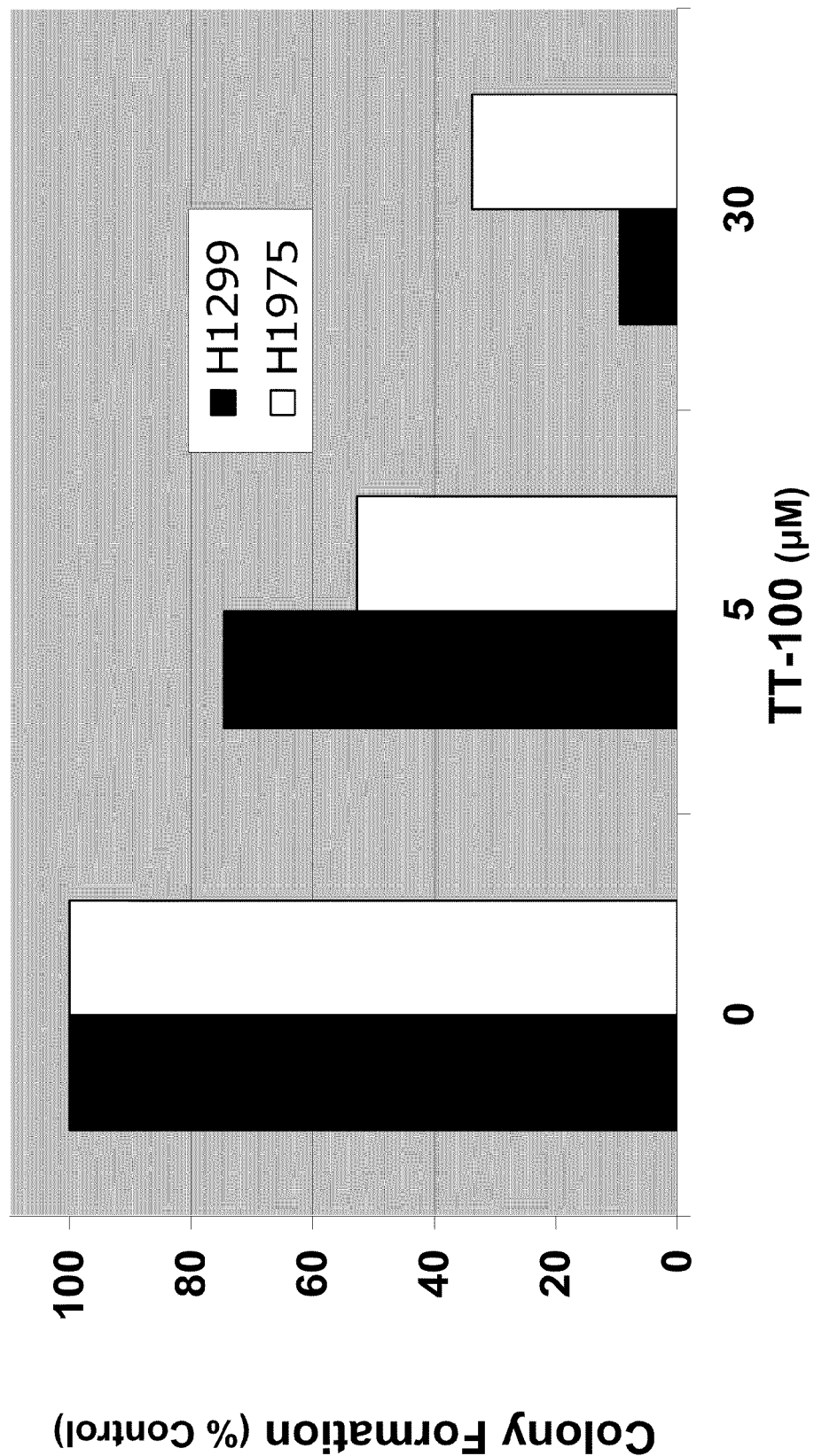
FIG. 4 demonstrates that TT-100 inhibits colony formation of Iressa-resistant NSCLC cells.

Iressa-resistant cells H1975 or H1299 NSCLC cells were also grown in soft agar in the absence or presence of 5 μM or 30 μM TT-100 for 8 days. Colony formation was assessed and compared with the control cells grown in the absence of TT-100. As shown in FIG. 4, TT-100 inhibited colony formation of Iressa-resistant H1975 and H1299 NSCLC cells. Cell proliferation was reduced more significantly when TT-100 was used at a higher dose.

In conclusion, these experiments demonstrate inhibition of Iressa-resistant NSCLC cells by TT-100.

Example 19

In Vivo TT-100 Therapy Inhibits Growth and Activation of IGF-1R and HER2 in Breast Tumors MCNeuA syngeneic breast cancer model was used to assess the effect of TT-100 in vivo. MCNeuA cells were implanted in MMTVneu transgenic mice to induce tumor growth. TT-100 was administered at 100 mg/kg by gavage (oral) or 37.5 mg/kg i.p., thrice weekly. Tumor growth was monitored and tumor size was measured at various time points. Tumor was excised on day 28, 24 hrs after the final TT-100 treatment. IGF-1R and HER2 phosphorylation were measured by ELISA.

Figure 5:
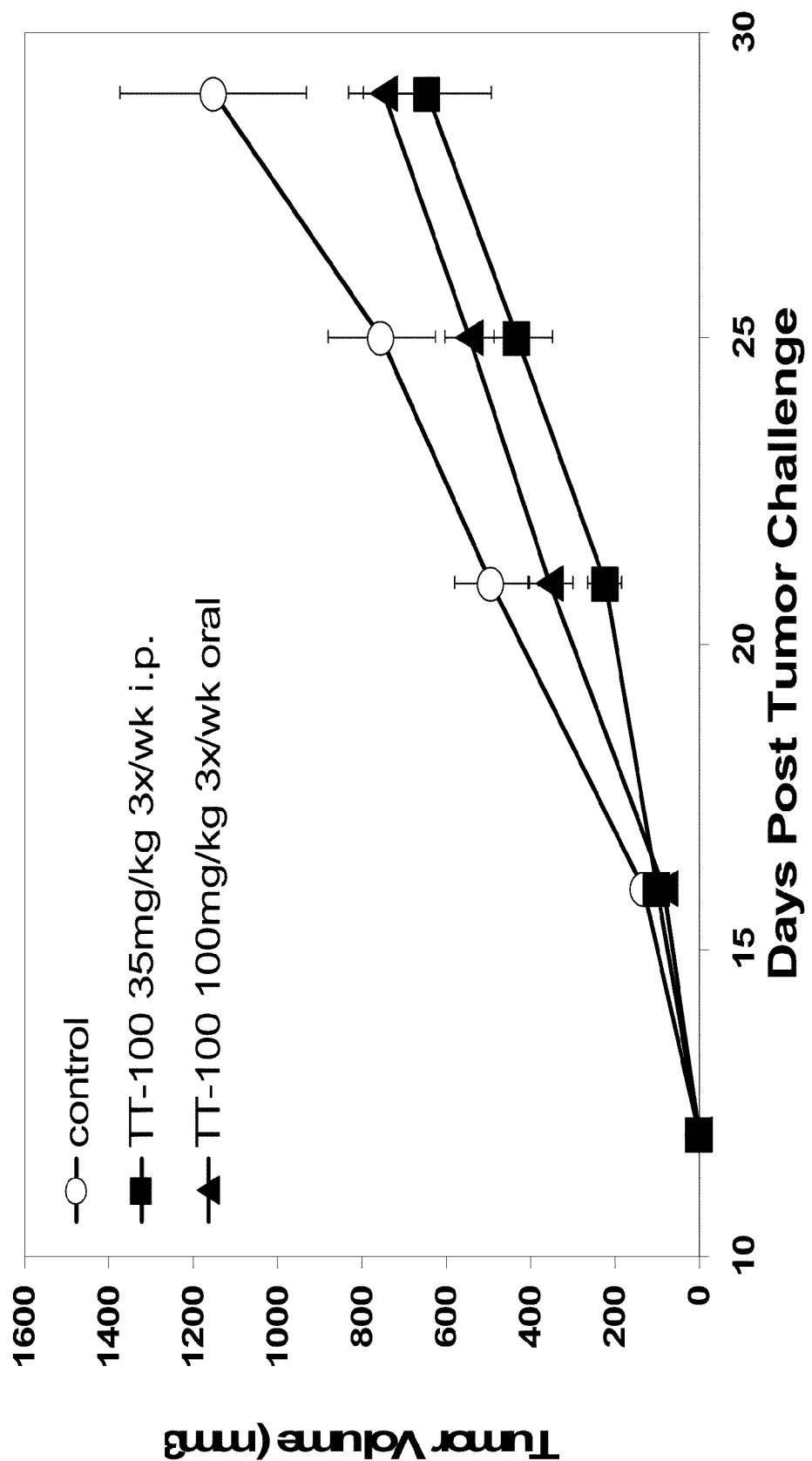
FIG. 5 demonstrates that TT-100 therapy inhibits growth of subcutaneous HER2 breast tumors in vivo.
Figure 6:
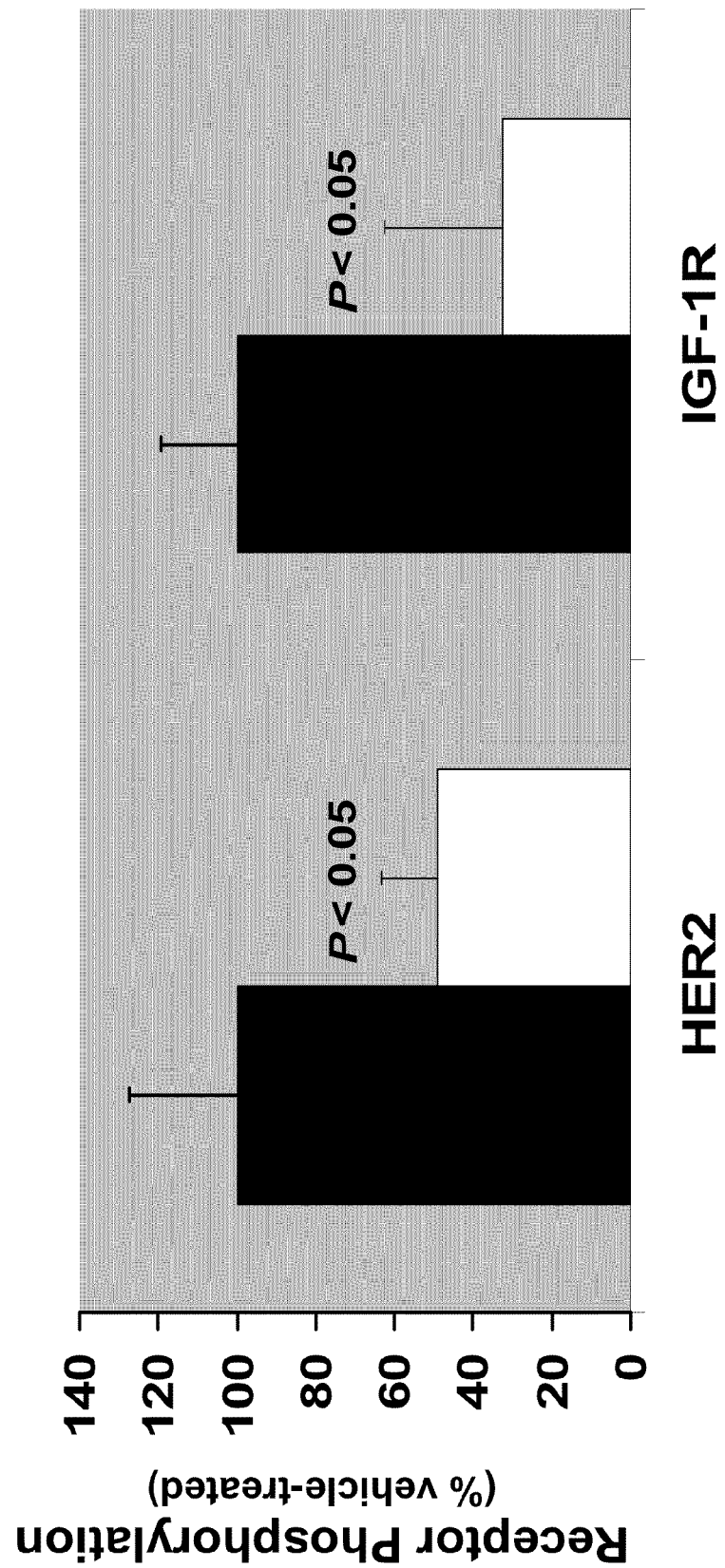
FIG. 6 demonstrates that TT-100 therapy inhibits EGR and IGF-1R activation in breast tumors in vivo.

FIG. 5 shows that TT-100 therapy, via both oral and i.p administration, inhibited the growth of subcutaneous HER2 breast tumors in vivo. FIG. 6 shows IGF-1R and HER2 receptor phosphorylation as compared to the vehicle-treated control. TT-100 therapy significantly inhibited HER2 and IGF-1R phosphorylation and therefore HER2 and IGF-1R activation in breast tumors in vivo.

These experiments demonstrate in vivo efficacy of TT-100 in inhibiting growth and activation of IGF-1R and HER2 in breast tumors.

Aspects of this application may be embodied in other forms or carried out in other ways without departing from the spirit or essential characteristics thereof. The present disclosure is therefore to be considered as in all aspects illustrated and not restrictive, and all changes which come within the meaning and range of equivalency are intended to be embraced therein.

What is claimed is:

1. A method for treating non-small cell lung cancer (NSCLC) in a subject, wherein said subject has developed resistance to treatment with an epidermal growth factor receptor (EGF-R) inhibitor, comprising administering an effective amount of a pharmaceutical composition capable of inhibiting the tyrosine kinase activity of both IGF-1R and EGF-R, wherein the pharmaceutical composition comprises nordihydroguaiaretic acid (NDGA), pharmaceutically acceptable salts thereof or a tautomer thereof.

2. The method of claim 1, wherein NDGA is administered in an amount selected from the group consisting of about 5 mg/kg to about 375 mg/kg per dose; about 5 mg/kg to about 250 mg/kg per dose; about 5 mg/kg to about 200 mg/kg per dose; about 5mg/kg to about 150 mg/kg per dose; about 5 mg/kg to about 100 mg/kg per dose; about 5mg/kg to about 75mg/kg per dose; and about 5 mg/kg to about 50 mg/kg per dose.

3. The method of claim 1, wherein NDGA is administered in an amount selected from the group consisting of from about 1,500 mg per day to about 2,500 mg per day; from about 1,800 mg per day to about 2,300 mg per day; and about 2,000 mg per day.

4. The method of claim 1, further comprising administering one or more additional anti cancer agents.

5. The method of claim 4, wherein said one or more additional anti-cancer agents is selected from the group consisting of EGFR inhibitors, IGF-1R inhibitors, DNA damaging agents, Topoisomerase inhibitors and Mitotic inhibitors.

6. The method of claim 1, wherein the pharmaceutical composition is administered more frequently than once every 6 days for a period of time, or more frequently than once every 2 days for a period of time.

* * * * *